US011972568B2

(12) United States Patent
Abramoff et al.

(10) Patent No.: US 11,972,568 B2
(45) Date of Patent: *Apr. 30, 2024

(54) AUTOMATED ASSESSMENT OF GLAUCOMA LOSS FROM OPTICAL COHERENCE TOMOGRAPHY

(71) Applicant: UNIVERSITY OF IOWA RESEARCH FOUNDATION, Iowa City, IA (US)

(72) Inventors: Michael Abramoff, University Heights, IA (US); Milan Sonka, Coralville, IA (US)

(73) Assignee: UNIVERSITY OF IOWA RESEARCH FOUNDATION, Iowa City, IA (US)

( * ) Notice: Subject to any disclaimer, the term of this patent is extended or adjusted under 35 U.S.C. 154(b) by 798 days.

This patent is subject to a terminal disclaimer.

(21) Appl. No.: 16/440,480

(22) Filed: Jun. 13, 2019

(65) Prior Publication Data
US 2019/0295257 A1   Sep. 26, 2019

Related U.S. Application Data

(63) Continuation of application No. 15/371,925, filed on Dec. 7, 2016, now Pat. No. 10,354,384, which is a
(Continued)

(51) Int. Cl.
*A61B 3/00* (2006.01)
*A61B 3/10* (2006.01)
(Continued)

(52) U.S. Cl.
CPC .......... *G06T 7/0016* (2013.01); *A61B 3/0025* (2013.01); *A61B 3/102* (2013.01);
(Continued)

(58) Field of Classification Search
CPC ......... G06T 7/0016; G06T 2207/10101; G06T 2207/30041; A61B 3/0025; A61B 3/102; A61B 3/1225
See application file for complete search history.

(56) References Cited

U.S. PATENT DOCUMENTS 4,883,061 A   11/1989   Zeimer
4,998,533 A    3/1991   Winkelman
(Continued)

FOREIGN PATENT DOCUMENTS

AU   2012207076   7/2012
CA      2610345   12/2006
(Continued)

OTHER PUBLICATIONS

Abramoff, M. et al., Image Processing with Image. J Biophotonics Int. 2004; 11(7):36-42.
(Continued)

*Primary Examiner* — Jack Dinh

(57) ABSTRACT

Systems and methods for assessing glaucoma loss using optical coherence topography. One method according to an aspect comprises receiving optical coherence image data and assessing functional glaucoma damage from retinal optical coherence image data. In an aspect, the systems and methods can map regions and layers of the eye to determine structural characteristics to compare to functional characteristics.

20 Claims, 28 Drawing Sheets

Related U.S. Application Data continuation of application No. 14/397,756, filed as application No. PCT/US2013/032477 on Mar. 15, 2013, now Pat. No. 9,545,196.

(60) Provisional application No. 61/642,945, filed on May 4, 2012.

(51) Int. Cl.
  *A61B 3/12* (2006.01)
  *G06T 7/00* (2017.01)

(52) U.S. Cl.
  CPC .. *A61B 3/1225* (2013.01); *G06T 2207/10101* (2013.01); *G06T 2207/30041* (2013.01)

(56) References Cited

U.S. PATENT DOCUMENTS

| | | | |
|---|---|---|---|
| 5,233,517 | A | 8/1993 | Jindra |
| 5,270,924 | A | 12/1993 | Hideshima |
| 5,303,709 | A | 4/1994 | Dreher et al. |
| 5,857,030 | A | 1/1999 | Gaborski et al. |
| 5,868,134 | A | 2/1999 | Sugiyama et al. |
| 6,000,799 | A | 12/1999 | Van de Velde |
| 6,003,993 | A | 12/1999 | Webb |
| 6,044,181 | A | 3/2000 | Szeliski et al. |
| 6,053,865 | A | 4/2000 | Sugiyama et al. |
| 6,104,828 | A | 8/2000 | Shioiri |
| 6,179,421 | B1 | 1/2001 | Pang |
| 6,276,798 | B1 | 8/2001 | Gil et al. |
| 6,453,057 | B1 | 9/2002 | Marshall et al. |
| 6,556,853 | B1 | 4/2003 | Cabib et al. |
| 6,567,682 | B1 | 5/2003 | Osterweil et al. |
| 6,674,894 | B1 | 1/2004 | Parker et al. |
| 6,712,469 | B2 | 3/2004 | Ando |
| 6,714,672 | B1 | 3/2004 | Berestov et al. |
| 6,728,561 | B2 | 4/2004 | Smith et al. |
| 6,731,782 | B2 | 5/2004 | Ashton |
| 6,757,409 | B2 | 6/2004 | Marshall et al. |
| 6,830,336 | B2 | 12/2004 | Fransen |
| 6,845,260 | B2 | 1/2005 | Liu et al. |
| 6,996,260 | B1 | 2/2006 | Skands et al. |
| 7,104,958 | B2 | 9/2006 | Crutchfield et al. |
| 7,206,435 | B2 | 4/2007 | Fujimura et al. |
| 7,232,240 | B2 | 6/2007 | Kosnik et al. |
| 7,242,810 | B2 | 7/2007 | Chang |
| 7,343,032 | B2 | 3/2008 | Oakley et al. |
| 7,474,775 | B2 | 1/2009 | Abramoff et al. |
| 7,524,061 | B2 | 4/2009 | Yan et al. |
| 7,574,028 | B2 | 8/2009 | Luo et al. |
| 7,578,028 | B2 | 8/2009 | Sellars |
| 7,620,501 | B2 | 11/2009 | Tek et al. |
| 7,712,898 | B2 | 5/2010 | Abramoff et al. |
| 7,715,597 | B2 | 5/2010 | Costache et al. |
| 8,140,329 | B2 | 3/2012 | Zhang et al. |
| 8,180,134 | B2 | 5/2012 | Wang |
| 8,194,936 | B2 | 6/2012 | Abramoff et al. |
| 8,340,437 | B2 | 12/2012 | Abramoff et al. |
| 8,463,065 | B2 | 6/2013 | Sun et al. |
| 8,611,623 | B2 | 12/2013 | Kurihara et al. |
| 8,616,702 | B2 | 12/2013 | Abramoff |
| 8,634,628 | B2 | 1/2014 | Inoue |
| 8,639,002 | B2 | 1/2014 | Tanaka et al. |
| 8,761,473 | B2 | 6/2014 | Ihara |
| 8,842,894 | B2 | 9/2014 | Ihara |
| 9,307,926 | B2 | 4/2016 | Begin et al. |
| 9,355,458 | B2 | 5/2016 | Ihara |
| 9,679,389 | B2 | 6/2017 | Ostrovsky-Berman et al. |
| 10,354,384 | B2 * | 7/2019 | Abramoff ............ A61B 3/0025 |
| 2002/0024516 | A1 | 2/2002 | Chen et al. |
| 2002/0126915 | A1 | 9/2002 | Lai et al. |
| 2002/0165837 | A1 | 11/2002 | Zhang et al. |
| 2003/0071970 | A1 | 4/2003 | Donnerhacke et al. |
| 2003/0166999 | A1 | 9/2003 | Liu et al. |
| 2003/0215119 | A1 | 11/2003 | Uppaluri et al. |
| 2004/0032488 | A1 | 2/2004 | Harman |
| 2004/0037453 | A1 | 2/2004 | Marshall et al. |
| 2004/0064057 | A1 | 4/2004 | Siegel |
| 2004/0085542 | A1 | 5/2004 | Soliz et al. |
| 2004/0105074 | A1 | 6/2004 | Soliz et al. |
| 2006/0023990 | A1 | 2/2006 | Shih et al. |
| 2006/0056727 | A1 | 3/2006 | Jones et al. |
| 2006/0119858 | A1 * | 6/2006 | Knighton ........... G01B 9/02091 356/479 |
| 2006/0140446 | A1 | 6/2006 | Luo et al. |
| 2007/0002275 | A1 | 1/2007 | Yan et al. |
| 2007/0020795 | A1 | 1/2007 | Mori et al. |
| 2007/0058865 | A1 | 3/2007 | Li et al. |
| 2007/0083492 | A1 | 4/2007 | Hohimer et al. |
| 2007/0092864 | A1 | 4/2007 | Reinhardt et al. |
| 2007/0110298 | A1 | 5/2007 | Graepel et al. |
| 2007/0122007 | A1 | 5/2007 | Austin et al. |
| 2007/0183661 | A1 | 8/2007 | El-Maleh et al. |
| 2007/0230795 | A1 | 10/2007 | Abramoff et al. |
| 2007/0244396 | A1 | 10/2007 | Vilser et al. |
| 2007/0253171 | A1 | 11/2007 | Cheng et al. |
| 2008/0205717 | A1 | 8/2008 | Reeves et al. |
| 2008/0240547 | A1 | 10/2008 | Cho et al. |
| 2008/0309881 | A1 * | 12/2008 | Huang ................ A61B 3/024 351/246 |
| 2009/0148024 | A1 | 6/2009 | Park |
| 2009/0257024 | A1 | 10/2009 | Luther et al. |
| 2010/0002929 | A1 | 1/2010 | Sammak et al. |
| 2010/0034457 | A1 | 2/2010 | Berliner et al. |
| 2010/0061601 | A1 | 3/2010 | Abramoff et al. |
| 2010/0074532 | A1 | 3/2010 | Gordon et al. |
| 2010/0082692 | A1 | 4/2010 | Akinyemi et al. |
| 2010/0103249 | A1 | 4/2010 | Lipton et al. |
| 2010/0104150 | A1 | 4/2010 | Saint Felix et al. |
| 2010/0118161 | A1 | 5/2010 | Tsurumi |
| 2010/0142824 | A1 | 6/2010 | Lu |
| 2010/0177943 | A1 | 7/2010 | Zhao et al. |
| 2010/0182406 | A1 | 7/2010 | Benitez |
| 2010/0271511 | A1 | 10/2010 | Ma et al. |
| 2010/0284180 | A1 | 11/2010 | Popovich et al. |
| 2011/0026794 | A1 | 2/2011 | Sundar et al. |
| 2011/0134221 | A1 | 6/2011 | Lee et al. |
| 2011/0135172 | A1 | 6/2011 | Kitamura |
| 2012/0236259 | A1 | 9/2012 | Abramoff et al. |
| 2012/0237094 | A1 | 9/2012 | Kurihara et al. |
| 2013/0208960 | A1 | 8/2013 | Reisman |
| 2014/0035901 | A1 | 2/2014 | Chen et al. |
| 2015/0379708 | A1 | 12/2015 | Abramoff et al. |

FOREIGN PATENT DOCUMENTS

| | | |
|---|---|---|
| CA | 2825169 | 7/2012 |
| EP | 0905509 A1 | 3/1999 |
| EP | 2665406 | 7/2012 |
| JP | 2007-097634 A | 4/2007 |
| JP | 2010-500081 A | 1/2010 |
| JP | 60-05663 B2 | 10/2016 |
| WO | WO-89/05493 | 6/1989 |
| WO | WO-2005/076198 | 8/2005 |
| WO | WO-2006/023990 A2 | 3/2006 |
| WO | WO-2006/105473 | 10/2006 |
| WO | WO-2007/031818 | 3/2007 |
| WO | WO-2007/118079 | 10/2007 |
| WO | WO-2008/150840 | 12/2008 |
| WO | WO-2010/099289 A1 | 9/2010 |
| WO | WO-2012/078636 | 6/2012 |
| WO | WO-2012/100221 | 7/2012 |
| WO | WO-2012/100225 A1 | 7/2012 |
| WO | WO-2012/106677 A2 | 8/2012 |
| WO | WO-2013/110668 A1 | 8/2013 |
| WO | WO-2014/143891 A1 | 9/2014 |

OTHER PUBLICATIONS

Adelson, E. et al., Pyramid Methods in Image Processing. RCA Engineer. 1984; 29(6):33-41.

(56) References Cited

OTHER PUBLICATIONS

Agurto et al., Detection and phenotyping of retinal disease using AM-FM processing for feature extraction. Signals, Systems and Computers, 2008 42nd Asilomar Conference on. IEEE, 2008 (5 pages).
Agurto et al., Multiscale AM-FM Methods for Diabetic Retinopathy Lesion Detection. Feb. 2010, Medical Imaging, IEEE Trans. 29(2):502-12.
Barriga et al., Automatic system for diabetic retinopathy screening based on AM-FM, partial least squares, and support vector machines. Apr. 2010, Biomedical Imaging: From Nano to Macro, 2010 IEEE International Symposium. pp. 1349-1352.
Barriga et al., Multi-scale AM-FM for lesion phenotyping on age-related macular degeneration. Computer-Based Medical Systems, 2009. CBMS 2009. 22nd IEEE International Symposium on. IEEE, 2009 (5 pages).
Boroujeni et al., Coronary Artery Center-line Extraction Using Second Order Local Features. Comput Math Methods Med. 2012 (21 pages).
Can, A. et al., A Feature-based Robust, Hierarchical, Algorithm for Registering Pairs of Images of the Curved Human Retina. IEEE Trans on Pattern analysis and Machine Intelligence. 2002; 24:347-64.
Can, A. et al., A Feature-based Technique for Joint, Linear Estimation of High-Order Image-to-Mosaic Transformations: Mosaicing the Curved Human Retina. IEEE Trans on Pattern Analysis and Machine Intelligence. 2002; 24(3):412-9.
Can, A. et al., Rapid Automated Tracing and Feature Extraction from Retinal Fundus Images Using Direct Exploratory Algorithms. IEEE Trans on Information Technology in Biomedicine. 1999; 3:125-38.
Chanwimaluang, T., Hybrid Retinal Image Registration. IEEE Trans on Information Technology in Biomedicine. 2006; 10:129-42.
Choe, T. et al., Optimal Global Mosaic Generation from Retinal Images. Int Conf on Pattern Recognition. 2006; 3:681-4.
Chrástek et al., Automated Calculation of Retinal Arteriovenous Ratio for Detection and Monitoring of Cerebrovascular Disease Based on Assessment of Morphological Changes of Retinal Vascular System. MVA 2002 Proc IAPR Workshop Machine Vision App. 2002; pp. 240-243.
Chrástek et al., Automated Segmentation of the Optic Nerve Head for Diagnosis of Glaucoma. Med Image Anal. 2005; pp. 297-314.
Eye Conditions Encyclopedia; "Optic Nerve Imaging"; EyeMDLink. com; Dec. 3, 2005; pp. 1-2.
Frangi et al., Multiscale Vessel Enhancement Filtering. Medical Image Computing and Computer-Assisted Intervention—MICCAI'98 Lecture Notes in Computer Sci. 1998; 1496:130-7.
Ginneken et al., IOP Image Processing Project Proposal: Computer-aided Diagnosis for Diabetic Retinopathy Detection in Fundus Images. Apr. 5, 2002; pp. 1-23.
Goatman, K., Automated Detection of Microaneurysms. Abstracts Reports. Biomed Phys Bioeng, University of Aberdeen. Retrieved from: <www.biomed.abdn.ac.uk/Abstracts/A07890/>. Jul. 10, 1997 (8 pages).
Ter Haar Romeny, B.M., Front-End Vision and Multi-Scale Image Analysis. Springer: 2003, pp. xiii-xviii.
Hackel, R. and Saine, P., Creating Retinal Fundus Maps. J Ophthalmic Photography. 2005; 27(1):10-8.
Huang et al., Development and Comparison of Automated Classifiers for Glaucoma Diagnosis Using Stratus Optical Coherence Tomography. Invest Ophthalmol Visual Sci. 2005; 46(11):4121-9.
Hyvärinen, A. and Oja, E., Independent Component Analysis: Algorithms and Applications. Neural Netw. 2000; 13(4-5):411.30.
Johnson et al., Structure and Function Evaluation (SAFE): II. Comparison of Optic Disk and Visual Field Characteristics. Am J Ophthalmol. 2003; 135(2):148-54.
Klein, B.E. et al., Cardiovascular Disease, Mortality, and Retinal Microvascular Characteristics in Type 1 Diabetes. Arch Intern Med. 2004; 164(17):1917-24.

Kondermann et al., Blood Vessel Classification into Arteries and Veins in Retinal Images. Proc SPIE. 2007; 6512:651247-1 to 651247-9.
Lee et al., Retinal atlas statistics from color fundus images. Med Imaging: Image Processing. 2010 (10 pages).
Light Shaping Diffusers Including a Rear Projection System. Physical Optics Corp. 2003. Reprinted from the Aug. 1996 issue of Photonics Spectra ©Laurin Publishing Co., Inc. [Retrieved on Apr. 15, 2010]. Retrieved from the Internet: <URL: http://www.poc.com/isd/default.asp?page=applications&sub=dst> p. 1. paragraph 7 (3 pages).
Lliev et al., Morphometric Assessment of Normal, Suspect and Glaucomatous Optic Discs with Stratus OCT and HRT II. Eye. 2005; pp. 1-12.
Maintz, J. and Viergever, M., A Survey of Medical Image Registration. Medical Image Analysis. 1998; 2(1):1-36.
Martus et al., Multivariate Approach for Quantification of Morphologic and Functional Damage in Glaucoma. Invest Ophthalmol Visual Sci. 41(5):1099-110, Apr. 2000.
Muramatsu et al., Automated selection of major arteries and veins for measurement of arteriolar-to-venular diameter ratio on retinal fundus images. Comp Med Imaging Graphics. 2011; 35(6):472-80.
Niemeijer, M. et al., Automatic determination of the artery-vein ratio in retinal images. Proc SPIE—The Int Soc Optic Eng. 2010; 7624: 762401-1 to 762401-10.
Quellec et al., Optimal Filter Framework for Automated, Instantaneous Detection of Lesions in Retinal Images. Oct. 21, 2010.
Quellec et al., Optimal wavelet transform for the detection of microaneurysms in retina photographs. IEEE Trans Med Imaging 27.9. 2008; 1230-41.
Ritter, N. et al., Registration of Stereo and Temporal Images of the Retina. IEEE Trans on Medical Imaging. 1999; 18:404-18.
"Segmentation"; Image Processing Fundamentals—Segmentation; Website: www.ph.tn.tudelft.nl/Courses/FIP/frames/fip-Segmenta. html; pp. 1-9, Jul. 2007.
Sharrett, A.R. et al., Retinal Arteriolar Diameters and Elevated Blood Pressure. Am J Epidemiol. 1999; 150(3):263-70.
Staal, J. et al., Ridge-based Vessel Segmentation in Color Images of the Retina. IEEE Trans on Medical Imaging. 2004; 23(4):501-9.
Swindale et al., Automated Analysis of Normal and Glaucomatous Optic Nerve Head Topography Images. Invest Ophthalmol Visual Sci. 2000; 41(7):1730-42.
Szymczak et al., Coronary Vessel Trees from 3D Imagery: a Topographical Approach. Med Image Anal. 2006; 10(4):548-59.
Toderici, G. et al., Evaluation of Variability and Significance of Fundus Camera Lens Distortion. Proc 26th Annual Int Conf of the IEEE Eng in Med and Bo Soc. pp. 1-5 (San Francisco, CA; Sep. 2004).
Tuytelaars et al., Matching widely separated views based on affine invariant regions. Int J Comp Vision 59.1. 2004; pp. 61-85.
Vincent, L., Morphological Grayscale Reconstruction in Image Analysis: Applications and Efficient Algorithms. IEEE Trans on Image Processing. 1993; 2:176-201.
Weng, J. et al., Camera Calibration with Distortion Models and Accuracy Evaluation. IEEE Trans on Pattern Analysis and Machine Intelligence. 1992; 14(10):965-80.
Wong et al., Computer-Assisted Measurement of Retinal Vessel Diameters in the Beaver Dam Eye Study Methodology: Correlation Between Eyes and Effect of Refractive Errors. Ophthalmology. 2004; 111(6):1183-90.
Xu, J. and Chutatape, O., Comparative Study of Two Calibration Methods on Fundus Camera. Proc 26th Annual Int Conf of the IEEE Eng in Med and Bio Soc. pp. 576-9 (Cancun, Mexico; 2003).
Yale Medicine Winter/Spring 1998, Imaging the Eye. Medicine's New Eyes. pp. 1-3.
Zomet, A., Seamless Image Stitching by Minimizing False Edges. IEEE Trans on Image Processing. 2006; 15:969-77.
International Search Report and Written Opinion dated Jan. 3, 2008 by the International Searching Authority for Patent Application No. PCT/US2006/012191, which was filed on Mar. 31, 2006 and published as WO 2006/105473 on Oct. 5, 2006 (Inventor—Abramoff et al.; Applicant—University of Iowa Research Foundation et al.) (7 pages).

(56) References Cited

OTHER PUBLICATIONS

International Preliminary Report on Patentability dated Mar. 10, 2009 by the International Searching Authority for Patent Application No. PCT/US2006/012191, which was filed on Mar. 31, 2006 and published as WO 2006/105473 on Oct. 5, 2006 (Inventor—Abramoff et al.; Applicant—University of Iowa Research Foundation et al.) (6 pages).
International Search Report and Written Opinion dated Sep. 17, 2008 by the International Searching Authority for Patent Application No. PCT/US2007/065862, which was filed on Apr. 3, 2007 and published as WO 2007/118079 on Oct. 18, 2007 (Inventor—Abramoff et al.; University of Iowa Research Foundation et al.) (4 pages).
International Preliminary Report on Patentability dated Nov. 4, 2008 by the International Searching Authority for Patent Application No. PCT/US2007/065862, which was filed on Apr. 3, 2007 and published as WO 2007/118079 on Oct. 18, 2007 (Inventor—Abramoff et al.; University of Iowa Research Foundation et al.) (4 pages).
International Search Report and Written Opinion dated Oct. 15, 2008 by the International Searching Authority for Patent Application No. PCT/US2008/065043, which was filed on May 29, 2008 and published as WO 2008/150840 on Dec. 11, 2008 (Inventor—Abramoff et al.; Applicant—University of Iowa Research Foundation) (6 pages).
International Preliminary Report on Patentability dated Dec. 1, 2009 by the International Searching Authority for Patent Application No. PCT/US2008/065043, which was filed on May 29, 2008 and published as WO 2008/150840 on Dec. 11, 2008 (Inventor—Inventor—Abramoff et al.; Applicant—University of Iowa Research Foundation) (5 pages).
International Search Report and Written Opinion dated May 3, 2010 by the International Searching Authority for Patent Application No. PCT/US2010/025369, which was filed on Feb. 25, 2010 and published as WO 2010/099289 on Sep. 2, 2010 (Inventor—Abramoff et al.; Applicant—University of Iowa Research foundation) (9 pages).
International Preliminary Report on Patentability dated Aug. 30, 2011 by the International Searching Authority for Patent Application No. PCT/US2010/025369, which was filed on Feb. 25, 2010 and published as WO 2010/099289 on Sep. 2, 2010 (Inventor—Abramoff et al.; Applicant—University of Iowa Research foundation) (8 pages).
International Search Report and Written Opinion was dated Apr. 3, 2012 by the International Searching Authority for Application No. PCT/US2011/63537 , which was filed on Dec. 6, 2011 and published as WO 2012/078636 on Jun. 14, 2012 (Inventor—Abramoff et al.; Applicant—University of Iowa Research Foundation) (11 Pages).
International Preliminary Report on Patentability was dated Jun. 12, 2013 by the International Searching Authority for Application No. PCT/US2011/63537 , which was filed on Dec. 6, 2011 and published as WO 2012/078636 on Jun. 14, 2012 (Inventor—Abramoff et al.; Applicant—University of Iowa Research Foundation) (10 Pages).
Preliminary Amendment was dated Jun. 7, 2013 to the U.S. Patent and Trademark Office for U.S. Appl. No. 13/992,552, filed Jul. 25, 2013 and published as US 2013/0301889 on Nov. 4, 2013 (Inventor—Abramoff et al.; Applicant—University of Iowa Research Foundation) (8 Pages).
Non Final Rejection was dated May 11, 2015 by the U.S. Patent and Trademark Office for U.S. Appl. No. 13/992,552, filed Jul. 25, 2013 and published as US 2013/0301889 on Nov. 4, 2013 (Applicant—University of Iowa Research Foundation; Inventor—Abramoff et al.) (31 Pages).
Response to Non Final Rejection was dated Oct. 12, 2015 to the U.S. Patent and Trademark Office for U.S. Appl. No. 13/992,552, filed Jul. 25, 2013 and published as US 2013/0301889 on Nov. 4, 2013 (Applicant—University of Iowa Research Foundation; Inventor—Abramoff, et al.) (12 Pages).

Final Rejection was dated Nov. 13, 2015 by the U.S. Patent and Trademark Office for U.S. Appl. No. 13/992,552, filed Jul. 25, 2013 and published as US 2013/0301889 on Nov. 4, 2013 (Applicant—University of Iowa Research Foundation; Inventor—Abramoff et al.) (32 Pages).
Non Final Rejection was dated Jul. 11, 2016 by the U.S. Patent and Trademark Office for U.S. Appl. No. 13/992,552, filed Jul. 25, 2013 and published as US 2013/0301889 on Nov. 4, 2013 (Applicant—University of Iowa Research Foundation; Inventor—Abramoff et al.) (37 Pages).
Final Rejection was dated Mar. 28, 2017 by the U.S. Patent and Trademark Office for U.S. Appl. No. 13/992,552, filed Jul. 25, 2013 and published as US 2015/0379708 on Dec. 31, 2015 (Inventor—Abramoff et al.; Applicant—University of Iowa Research Foundation) (39 pages).
Non-Final Office Action dated Dec. 11, 2017 by the U.S. Patent and Trademark Office for U.S. Appl. No. 13/992,552, filed Jul. 25, 2013 and published as US 2015/0379708 on Dec. 31, 2015 (Inventor—Abramoff et al.; Applicant—University of Iowa Research Foundation) (33 pages).
Notice of Allowance dated Jul. 11, 2018 by the U.S. Patent and Trademark Office for U.S. Appl. No. 13/992,552, filed Jul. 25, 2013 and published as US 2015/0379708 on Dec. 31, 2015 (Inventor—Abramoff et al.; Applicant—University of Iowa Research Foundation) (8 pages).
International Search Report and Written Opinion dated May 8, 2012 by the International Searching Authority for Patent Application No. PCT/US2012/022115, which was filed on Jan. 20, 2012 and published as WO 2012/100225 on Jul. 26, 2012 (Inventor—Abramoff et al.; Applicant—University of Iowa Research Foundation) (6 pages).
International Preliminary Report on Patentability dated Jul. 23, 2013 by the International Searching Authority for Patent Application No. PCT/US2012/022115, which was filed on Jan. 20, 2012 and published as WO 2012/100225 on Jul. 26, 2012 (Inventor—Abramoff et al.; Applicant—University of Iowa Research Foundation) (5 pages).
European Search Report dated Mar. 16, 2016 by the European Patent Office for Application No. 12736290.3, which was filed on Jan. 20, 2011, and published as 2665406, on Nov. 27, 2013 (Inventor—Abramoff et al.; Applicant—University of Iowa Research Foundation) (8 Pages).
International Search Report and Written Opinion was dated May 25, 2012 by the International Searching Authority for Application No. PCT/US2012/022111, which was filed on Jan. 20, 2012 and published as WO 2012/100221 on Jul. 26, 2012 (Inventor—Abramoff et al.; Applicant—University of Iowa Research Foundation) (7 Pages).
International Preliminary Report on Patentability was dated Jul. 23, 2013 by the International Searching Authority for Application No. PCT/US2012/022111, which was filed on Jan. 20, 2012 and published as WO 2012/100221 on Jul. 26, 2012 (Inventor—Abramoff et al.; Applicant—University of Iowa Research Foundation) (6 Pages).
Preliminary Amendment was dated Jun. 19, 2012 to the U.S. Patent and Trademark Office for U.S. Appl. No. 13/355,386, filed Jan. 20, 2012 and published as US 2012/0236259 on Sep. 20, 2012 (Applicant—University of Iowa Research Foundation; Inventor—Abramoff et al.) (3 Pages).
Non Final Rejection was dated Sep. 19, 2013 by the U.S. Patent and Trademark Office for U.S. Appl. No. 13/355,386, filed Jan. 20, 2012 and published as US 2012/0236259 on Sep. 20, 2012 (Applicant—University of Iowa Research Foundation; Inventor—Abramoff et al.) (16 Pages).
Response to Non Final Rejection was dated Dec. 19, 2013 to the U.S. Patent and Trademark Office for U.S. Appl. No. 13/355,386, filed Jan. 20, 2012 and published as US 2012/0236259 on Sep. 20, 2012 (Applicant—University of Iowa Research Foundation; Inventor—Abramoff f et al.) (10 Pages).
Final Rejection was dated Mar. 11, 2014 by the U.S. Patent and Trademark Office for U.S. Appl. No. 13/355,386, filed Jan. 20, 2012

(56) References Cited

OTHER PUBLICATIONS and published as US 2012/0236259 on Sep. 20, 2012 (Applicant—University of Iowa Research Foundation; Inventor—Abramoff et al.) (17 Pages).
Non Final Rejection was dated Feb. 6, 2015 by the U.S. Patent and Trademark Office for U.S. Appl. No. 13/355,386, filed Jan. 20, /2012 and published as US 2012/0236259 on Sep. 20, 2012 (Applicant—University of Iowa Research Foundation; Inventor—Abramoff et al.) (13 Pages).
Response to Non Final Rejection was dated May 6, 2015 to the U.S. Patent and Trademark Office for U.S. Appl. No. 13/355,386, filed Jan. 20, 2012 and published as US 2012/0236259 on Sep. 20, 2012 (Applicant—University of Iowa Research Foundation; Inventor—Abramoff et al.) (11 Pages).
Final Rejection dated Jun. 23, 2015 by the U.S. Patent and Trademark Office for U.S. Appl. No. 13/355,386, filed Jan. 20, 2012 and published as US 2012/0236259 on Sep. 20, 2012 (Applicant—University of Iowa Research Foundation; Inventor—Abramoff et al.) (14 Pages).
Response to Final Rejection dated Aug. 24, 2015 to the U.S. Patent and Trademark Office for U.S. Appl. No. 13/355,386, filed Jan. 20, 2012 and published as US 2012/0236259 on Sep. 20, 2012 (Applicant—University of Iowa Research Foundation; Inventor—Abramoff et al.) (11 Pages).
Non Final Rejection dated Mar. 30, 2016 by the U.S. Patent and Trademark Office for U.S. Appl. No. 13/355,386, filed Jan. 20, 2012 and published as US 2012/0236259 on Sep. 20, 2012 (Applicant—University of Iowa Research Foundation; Inventor—Abramoff et al.) (12 Pages).
Response to Non Final Rejection dated Sep. 30, 2016 to the U.S. Patent and Trademark Office for U.S. Appl. No. 13/355,386, filed Jan. 20, 2012 and published as US 2012/0236259 on Sep. 20, 2012 (Applicant—University of Iowa Research Foundation; Inventor—Abramoff f et al.) (9 Pages).
Final Rejection dated Nov. 9, 2016 by the U.S. Patent and Trademark Office for U.S. Appl. No. 13/355,386, filed Jan. 20, 2012 and published as US 2012/0236259 on Sep. 20, 2012 (Applicant—University of Iowa Research Foundation; Inventor—Abramoff et al.) (14 Pages).
Notice of Allowance dated Nov. 8, 2017 by the U.S. Patent and Trademark Office for U.S. Appl. No. 13/355,386, filed Jan. 20, 2012 and published as US 2012/0236259 on Sep. 20, 2012 (Applicant—University of Iowa Research Foundation; Inventor—Abramoff et al.)(8 Pages).
Issue Notification dated Mar. 7, 2018 by the U.S. Patent and Trademark Office for U.S. Appl. No. 13/355,386, filed Jan. 20, 2012 and published as US 2012/0236259 on Sep. 20, 2012 (Applicant—University of Iowa Research Foundation; Inventor—Abramoff et al.) (1 Page).
International Search Report and Written Opinion was dated Sep. 4, 2014 by the International Searching Authority for Application No. PCT/US2014/014298, which was filed on Jan. 31, 2014 and published as WO/2014/158345 on Oct. 2, 2014 (Applicant—University of Iowa Research Foundation) (7 Pages).
International Preliminary Report on Patentability was dated Aug. 4, 2015 by the International Searching Authority for Application No. PCT/US2014/014298, which was filed on Jan. 31, 2014 and published as WO/2014/158345 on Oct. 2, 2014 (Inventor—Abramoff et al.; Applicant—University of Iowa Research Foundation) (6 Pages).
Preliminary Amendment was dated Jul. 30, 2015 to the U.S. Patent and Trademark Office for U.S. Appl. No. 14/764,926, filed Jul. 30, 2015 and published as US 2015/0379708 on Dec. 31, 2015 (Applicant—University of Iowa Research Foundation; Inventor—Abramoff et al.) (4 Pages).
Non Final Rejection was dated Jan. 27, 2017 by the U.S. Patent and Trademark Office for U.S. Appl. No. 14/764,926, filed Jul. 30, 2015 and published as US 2015/0379708 on Dec. 31, 2015 (Applicant—University of Iowa Research Foundation; Inventor—Abramoff et al.) (9 Pages).

International Search Report and Written Opinion was dated Aug. 15, 2014 by the International Searching Authority for Application No. PCT/US2014/28055, which was filed on Mar. 14, 2014 and published as WO 2014/143891 on Sep. 18, 2014 (Inventor—Abramoff et al.; Applicant—University of Iowa Research Foundation) (6 Pages).
International Preliminary Report on Patentability was dated Sep. 15, 2015 by the International Searching Authority for Application No. PCT/US2014/28055, which was filed on Mar. 14, 2014 and published as WO 2014/143891 on Sep. 18, 2014 (Inventor—Abramoff et al.; Applicant—University of Iowa Research Foundation) (5 Pages).
Non Final Rejection was dated Nov. 4, 2016 by the U.S. Patent and Trademark Office for U.S. Appl. No. 14/774,801, filed Sep. 11, 2015 and published as US 2016/0035088 on Feb. 4, 2016 (Applicant—University of Iowa Research Foundation; Inventor—Abramoff et al.) (6 Pages).
Preliminary Amendment was dated Sep. 11, 2015 to the U.S. Patent and Trademark Office for U.S. Appl. No. 14/774,801, filed Sep. 11, 2015 and published as US 2016/0035088 on Feb. 4, 2016 (Applicant—University of Iowa Research Foundation; Inventor—Abramoff et al.) (4 Pages).
Final Office Action dated May 12, 2017 by the U.S. Patent and Trademark Office for U.S. Appl. No. 14/774,801, filed Sep. 21, 2015 and published as US 2016/0035088 on Feb. 4, 2016 (Applicant—University of Iowa Research Foundation; Inventor—Abramoff et al.) (7 Pages).
Non-Final Office Action dated Nov. 17, 2017 by the U.S. Patent and Trademark Office for U.S. Appl. No. 14/774,801, filed Sep. 21, 2015 and published as US 2016/0035088 on Feb. 4, 2016 (Applicant—University of Iowa Research Foundation; Inventor—Abramoff et al.) (8 Pages).
Final Office Action dated Jul. 23, 2018 by the U.S. Patent and Trademark Office for U.S. Appl. No. 14/774,801, filed Sep. 21, 2015 and published as US 2016/0035088 on Feb. 4, 2016 (Applicant—University of Iowa Research Foundation; Inventor—Abramoff et al.) (8 Pages).
International Search Report and Written Opinion was dated Aug. 5, 2015 by the International Searching Authority for Application No. PCT/US2015/022021, which was filed on Mar. 23, 2015 and published as WO 2015/143435 on Sep. 24, 2015 (Inventor—Abramoff et al.; Applicant—University of Iowa Research Foundation) (9 Pages).
International Preliminary Report on Patentability was dated Sep. 21, 2016 by the International Searching Authority for Application No. PCT/US2015/022021, which was filed on Mar. 23, 2015 and published as WO 2015/143435 on Sep. 24, 2015 (Inventor—Abramoff et al.; Applicant—University of Iowa Research Foundation) (6 Pages).
Non Final Rejection dated Dec. 22, 2017 by the U.S. Patent and Trademark Office for U.S. Appl. No. 15/128,035, filed Sep. 21, 2016 and published as US 2017/0098311 on Apr. 6, 2017 (Inventor—Abramoff et al.; Applicant—University of Iowa Research Foundation et al.) (16 pages).
Final Office Action dated Aug. 28, 2018 by the U.S. Patent and Trademark Office for U.S. Appl. No. 15/128,035, filed Sep. 21, 2016 and published as US 2017/0098311 on Apr. 6, 2017 (Inventor—Abramoff et al.; Applicant—University of Iowa Research Foundation et al.) (19 pages).
Non-Final Office Action dated Dec. 18, 2015 by the U.S. Patent and Trademark Office for U.S. Appl. No. 14/397,756, filed Oct. 29, 2014 and issued as U.S. Pat. No. 9,545,196 on Jan. 17, 2017 (Inventor—Abramoff et al.; Applicant—University of Iowa Research Foundation et al.) (5 pages).
Notice of Allowance issued on Aug. 29, 2016 by the U.S. Patent and Trademark Office for U.S. Appl. No. 14/397,756, filed Oct. 29, 2014 and issued as U.S. Pat. No. 9,545,196 on Jan. 17, 2017 (Inventor—Abramoff et al.; Applicant—University of Iowa Research Foundation et al.) (7 pages).

(56) References Cited

OTHER PUBLICATIONS

Kexin Deng, Jie Tian, Jian Zheng, Xing Zhang, Xiaoqian Dai, Min Xu, "Retinal Fundus Image Registration via Vascular Structure Graph Matching", International Journal of Biomedical Imaging, vol. 2010, Article ID 906067, 13 pages, 2010.

* cited by examiner

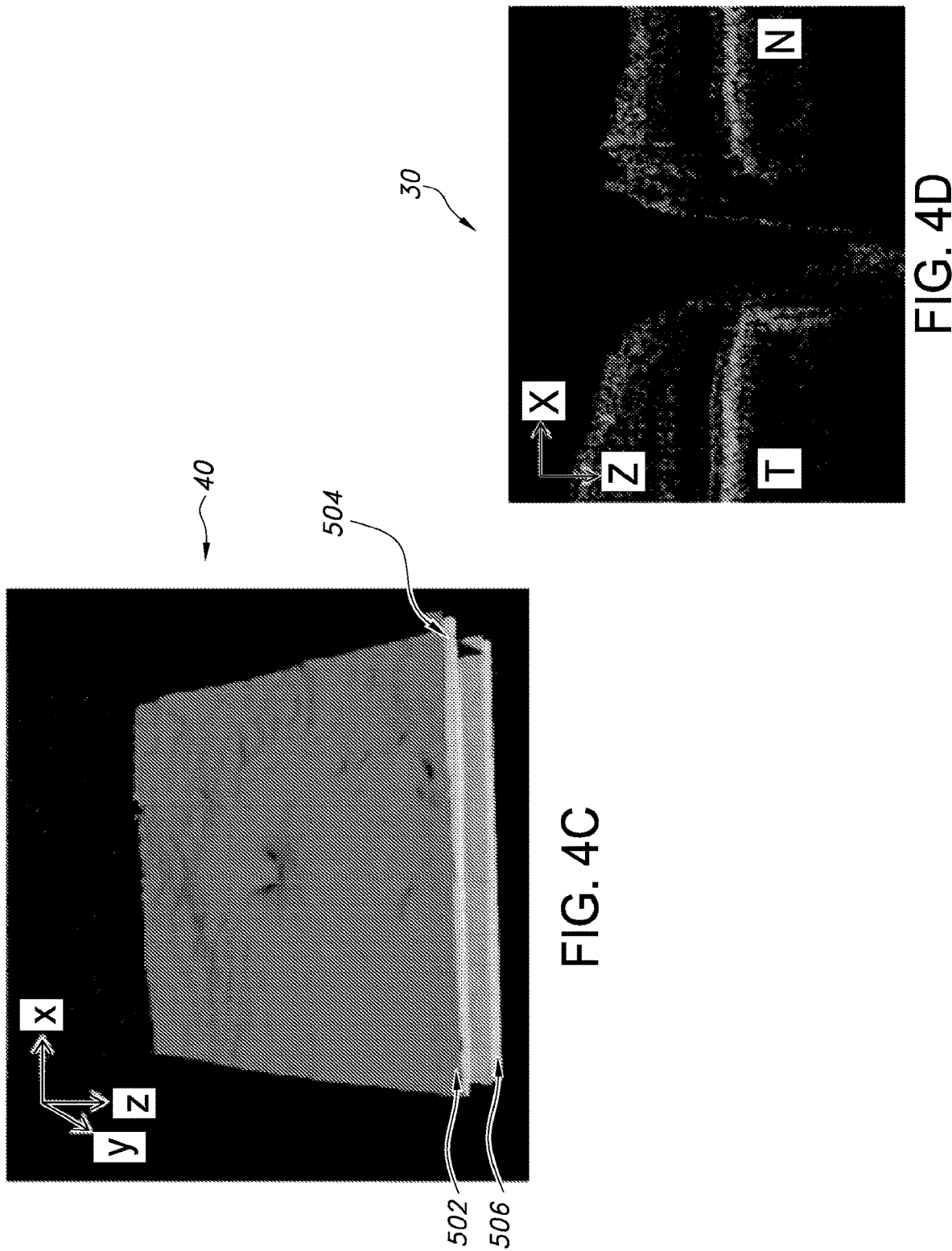

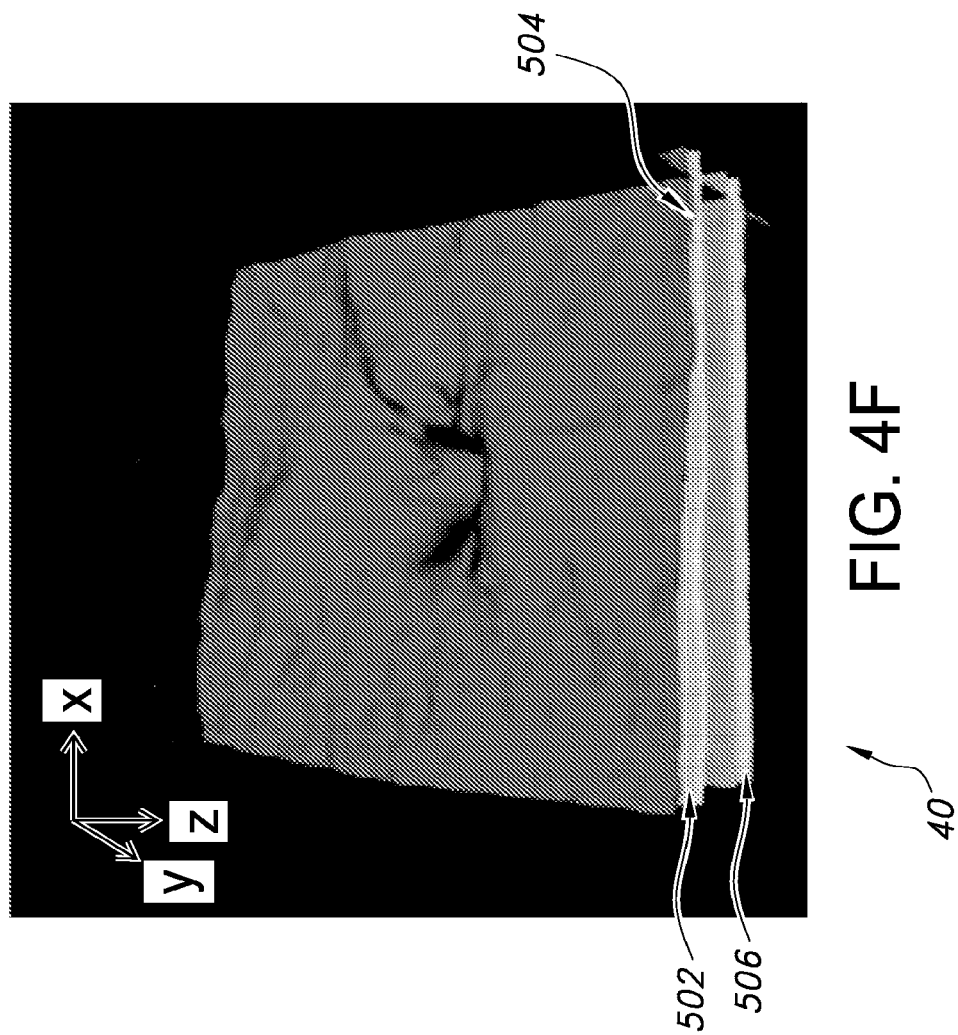
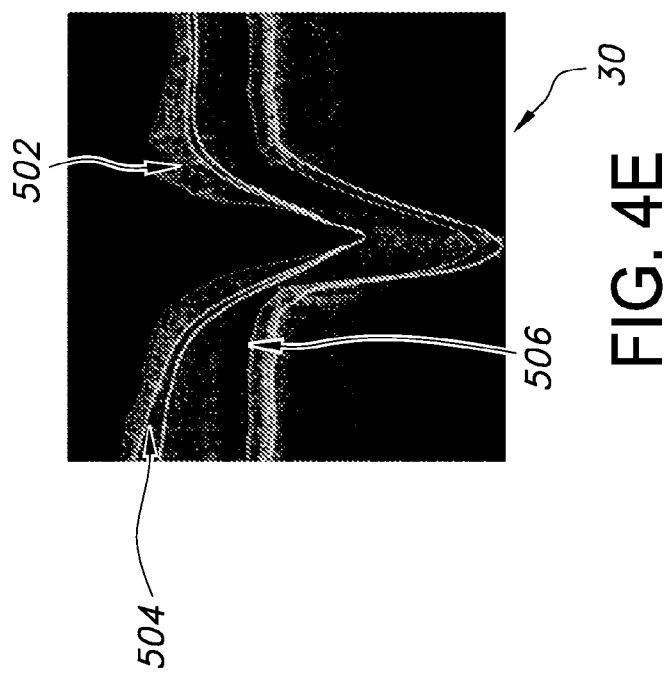
FIG. 4F
FIG. 4E

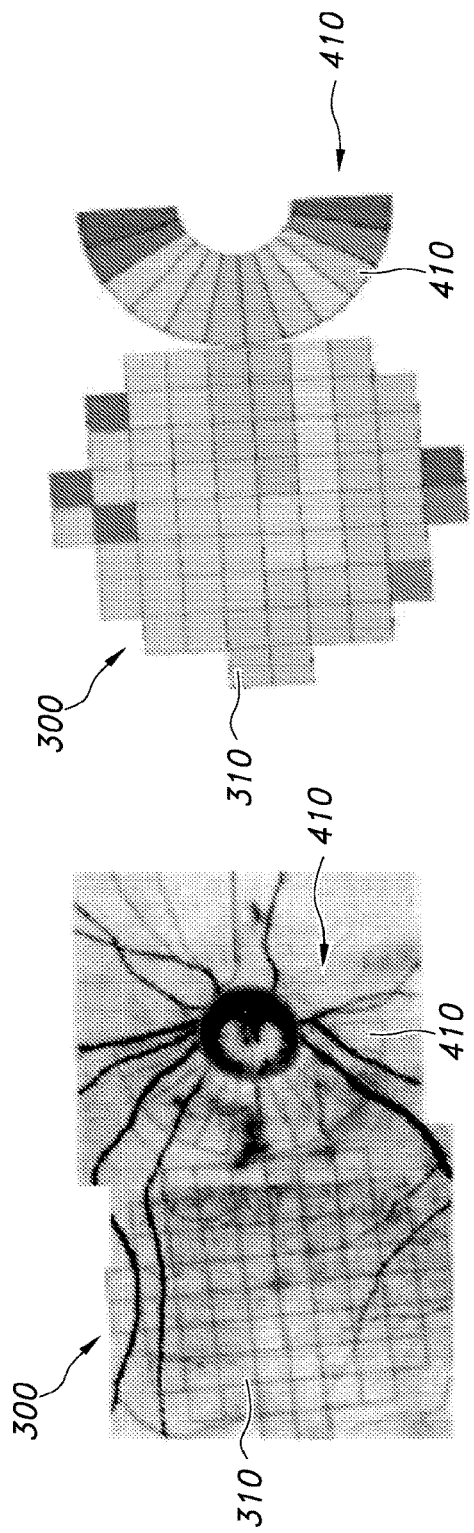
FIG. 9A
FIG. 9B
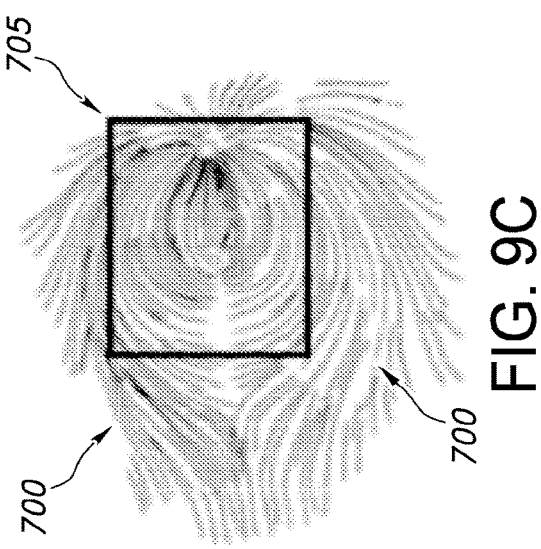
FIG. 9C
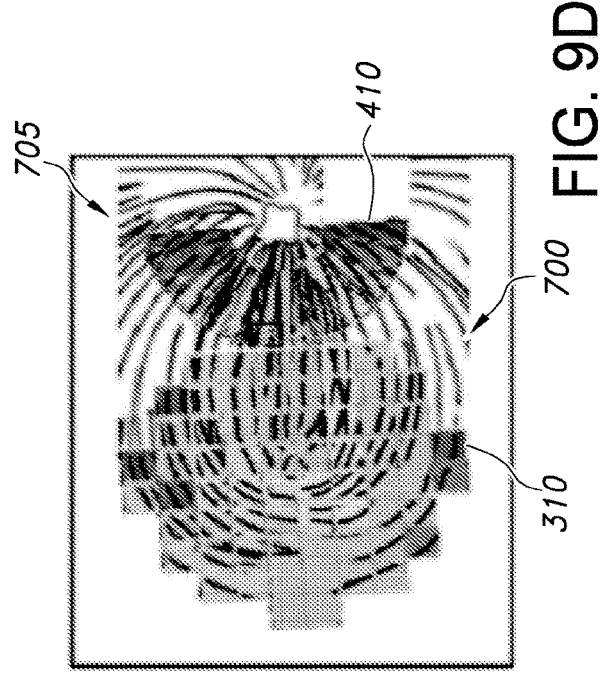
FIG. 9D

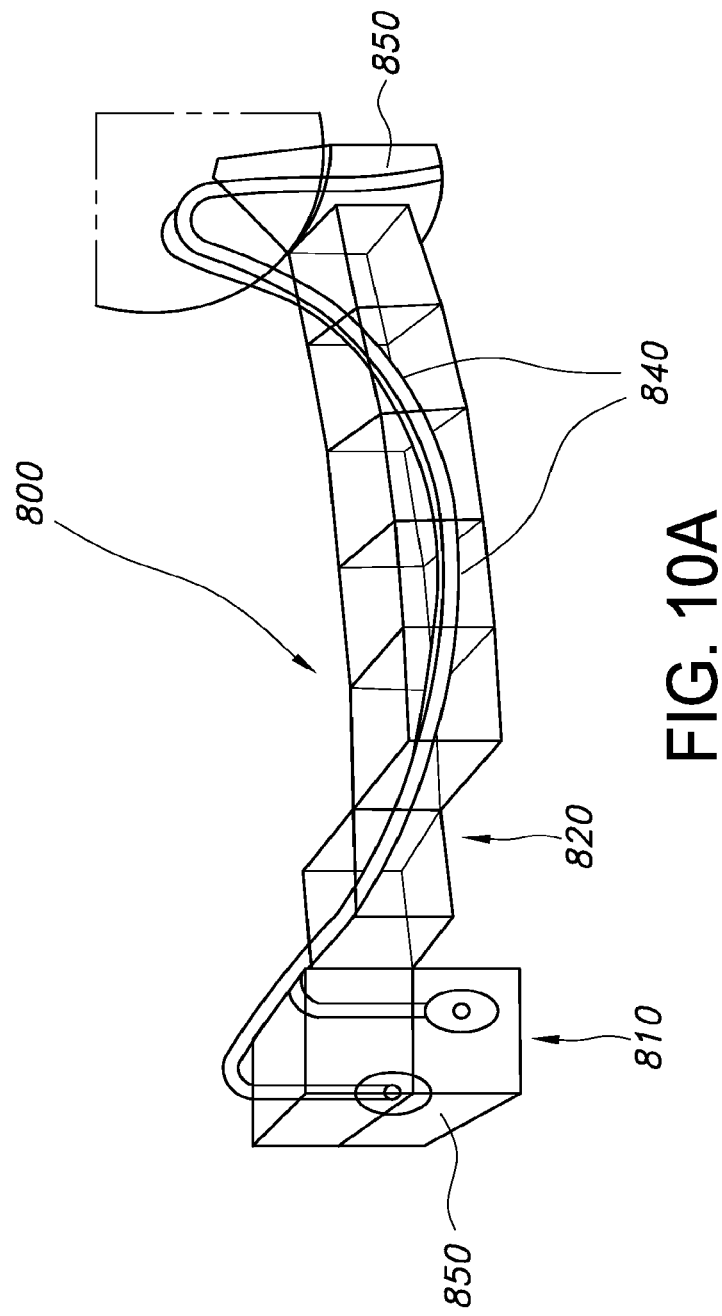

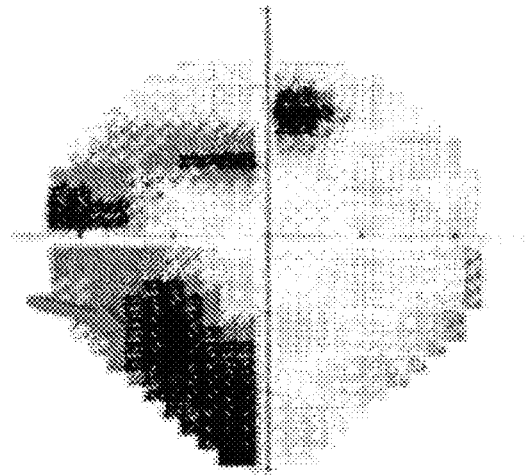
FIG. 12B
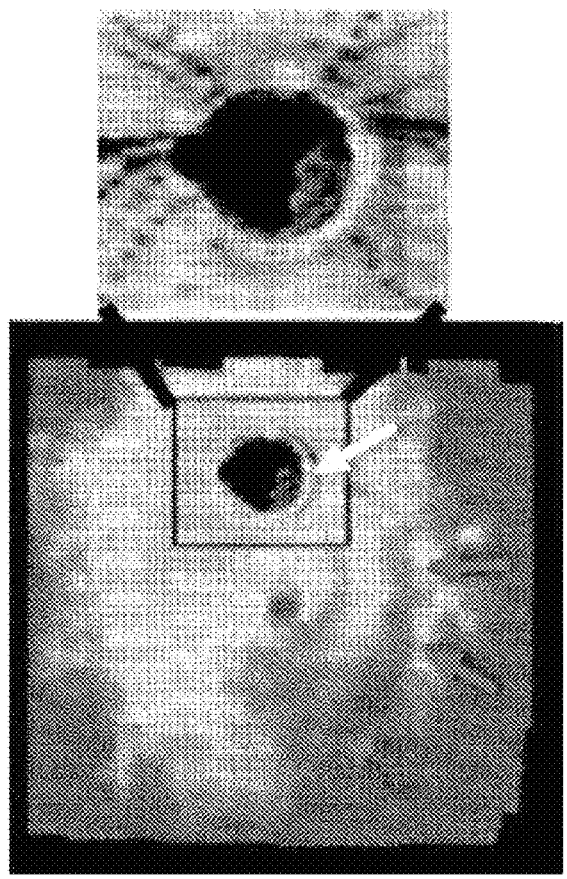
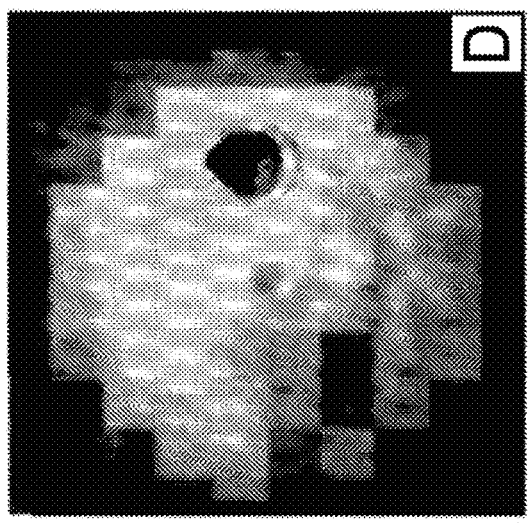
FIG. 12D
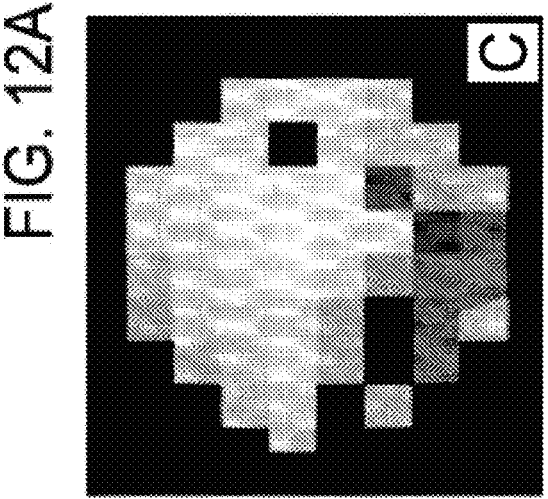
FIG. 12C
FIG. 12A

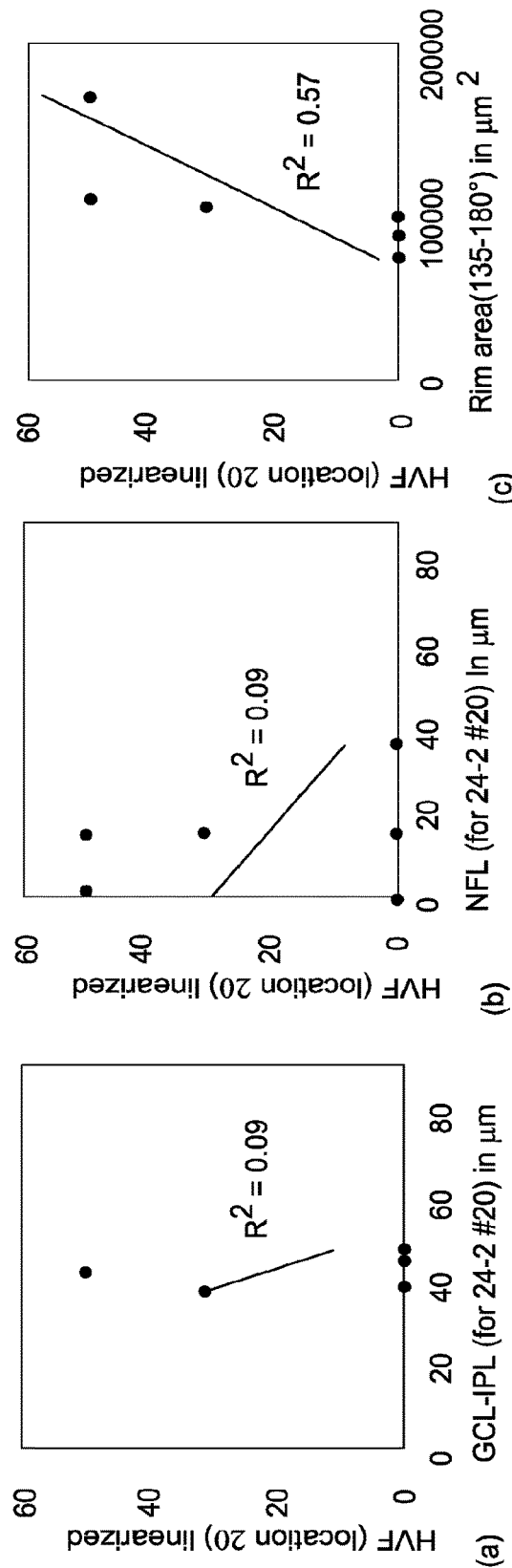
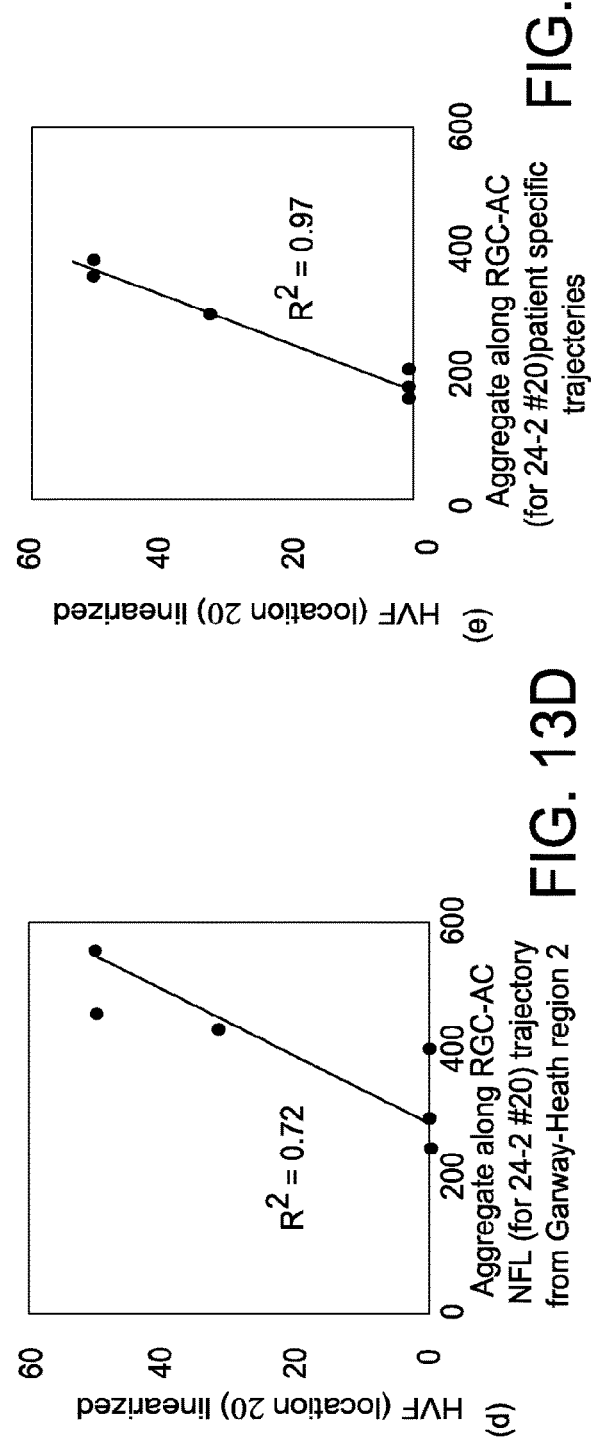
FIG. 13A FIG. 13B FIG. 13C FIG. 13D FIG. 13E

AUTOMATED ASSESSMENT OF GLAUCOMA LOSS FROM OPTICAL COHERENCE TOMOGRAPHY

CLAIM OF PRIORITY

This application is a continuation of U.S. application Ser. No. 15/371,925, filed on Dec. 7, 2016, which is a continuation of U.S. application Ser. No. 14/397,756, filed on Oct. 29, 2014, and issued as U.S. Pat. No. 9,545,196, which is a U.S. National Phase Application of International Application Number PCT/US2013/032477, filed on Mar. 15, 2013, which claims priority to U.S. Provisional Application No. 61/642,945, filed on May 4, 2012, each of which are herein incorporated by reference in their entireties.

STATEMENT REGARDING FEDERALLY SPONSORED RESEARCH

This invention was made with government support under Grant EY018853. Awarded by the National Institutes of Health. The government has certain rights in the invention.

BACKGROUND

Glaucoma is a progressive disease of the optic nerve that left untreated can lead to irreversible loss of vision. Glaucoma results in apoptosis of the retinal ganglion cells (RGCs), including their axon and cell body. The loss of the RGC axonal bundle within the optic nerve head (ONH) leads to characteristic cupping and corresponding visual field (VF) loss. It is important to detect the disease early, as well as to monitor changes in glaucomatous damage. The clinical standard for detection of disease and its progression has been the automated perimetry and clinical assessment of the optic nerve cup. However, once moderate visual field loss occurs (in the range of −15 dB mean deviation (MD) loss or more), retest variability rises substantially and limits a reliable determination of visual field change. The population 95% confidence limits extend to nearly the entire operating range of the Humphrey Field Analyzer perimetric device.

Much effort has been devoted to studying the structural-functional (S-F) correlation in glaucoma with the hope that a good S-F correlation can help diagnose and monitor disease progression by providing complementary information. For example, a good S-F correlation would allow the objective structural assessment by optical coherence tomography (OCT) to predict the level of subjective functional damage in glaucoma. However, increased dynamic range and tighter S-F correlation is desired.

Increased dynamic range and tighter (less variable) S-F correlation can lead to the following clinical benefits: 1) Improved ability to stage the disease over the entire spectrum, not only by function, but also by structure; 2) Improved ability to confirm functional changes with corresponding structural changes, leading to improved ability to detect change; 3) Increased ease and patient tolerance of frequent testing for glaucoma progression to detect those who are progressing faster. If within individual variability (WIV) of OCT is reduced, improved clinical care can be achieved with frequent structural testing, which would be much easier for the average glaucoma patient, rather than frequent functional testing; and 4) Objective assessment of glaucoma damage becoming feasible for those patients who cannot perform VF tests (very young children, elderly with mental or physical limitations, etc.).

SUMMARY

It is to be understood that both the following general description and the following detailed description are exemplary and explanatory only and are not restrictive, as claimed.

In an aspect, FIG. 2A illustrates a curvilinear relationship between the thickness of the peripapillary retinal nerve fiber layer (PP-NFL)(shown as RNFL on the Y-axis, measured in μm) and VF (shown as field loss on the X-axis, measured in dB). The data show that below approximately −10 dB loss, the PP-NFL thickness reaches a "floor," thus limiting its dynamic range. In another aspect, as illustrated in FIG. 2B, a curvilinear relationship can be found between the thickness of the macular ganglion cell layer (GCL)(shown as RCG+IPL on the Y-axis, measured in μm) and VF (shown as Relative Field Sensitivity on the X-axis, measured in dB), with a dynamic range limited to VF better than −10 dB. These results imply the OCT PP-NFL and GCL global thickness measurements are not clinically useful when the VF deficit is below −10 dB loss.

If one were to use OCT to predict visual function, it would be desirable to increase the dynamic range of the OCT structural measures to match that of the VF. A more sophisticated set of structural indices based on RGC anatomy rather than a single layer thickness is likely to have increased dynamic range to match functional range. The second problem consists of a substantial variability in the S-F relationship. As shown in FIGS. 2A and 2C linear model has been proposed with variability to describe both within-individual variability (WIV)(shown in blue) and between-individual variability (BIV)(shown in red) of both PP-NFL (shown as RNFL on the Y-axis measured in μm) and VF (shown as Field Loss on the X-axis, measured in dB). The BIV was large for PP-NFL for early glaucoma, while being large for VF in moderate glaucoma (VF loss −10 to −20 dB, FIG. 2c).

In general, WIV is better than BIV for both measures regardless of glaucoma stage. Reducing BIV and WIV of OCT measures through improved hardware (e.g., spectral-domain OCT (SD-OCT), compared to the use of time-domain Zeiss Stratus OCT in earlier studies) and software can lead to "tighter" S-F correlation, improving structural prediction of function.

The limitations of reliability and reproducibility for visual field measurement as the main parameter in the assessment of glaucoma damage inhibits optimal patient care and research into improved treatments. Though currently available SD-OCT derived measurements of glaucomatous damage such as OCT-derived nerve fiber layer thickness and cup-to-disc ratio are highly patient friendly, reproducible and robust, they do not correlate well with visual function as expressed by threshold visual field sensitivity.

In an aspect, analysis of SD-OCT images of patients with glaucoma can be used to measure damage to the retinal ganglion cell-axonal complex, as it traverses the retina from ganglion cell body to optic nerve head. As an example, metrics can be used assessing structure and morphology of ganglion cell-axonal layers and optic nerve head and demonstrated that these topological relationships can be mapped along nerve fiber bundles.

In an aspect, analysis of SD-OCT images can result in new damage metrics that correspond better with visual field threshold sensitivity than current approaches allow. In an aspect, the systems and methods of the present disclosure determine/predict glaucoma visual function from objective structure measurements by OCT. Accordingly, the systems and methods minimize the testing burden for glaucoma patients and potentially decrease the need for frequent visual field (VF) testing resulting from long-term fluctuation of visual response.

In another aspect, the systems and methods can establish a baseline for the focal structural-functional correlation in the retina covered by the Humphrey 24-2 perimetry test (24 degree radius visual field) by comparing 24-2 thresholds with their corresponding structural indices derived from registered multi-field SD-OCT scans in glaucoma patients and normal subjects. As an example, the system and methods can be used to derive a baseline predictive model of function from structural properties of the inner retinal layers, comprised of retinal ganglion cell and nerve fiber layers.

In another aspect, by incorporating structural parameters along SD-OCT atlas-based retinal ganglion cell-axonal complex (RGC-AC) trajectories, the performance of the predictive structure-function model can be improved over the art.

In yet another aspect, the systems and methods can be used to evaluate whether prediction of 24-2 thresholds is improved by deriving individual-based RGC-AC trajectories instead of from an RGC-AC atlas.

In an aspect, the systems and methods can use 9-field or 7-field per eye 3D SD OCT images accompanied by 24-2 visual field test data on the same day from 100 patients with glaucoma and 40 normal subjects. However, other optics, images, and testing can be used. In another aspect, glaucoma patients and normal subjects can be age frequency matched, based on the age distribution of the glaucoma group (approximate ten-year intervals) to minimize any possible bias in OCT image characteristics.

Additional advantages will be set forth in part in the description which follows or may be learned by practice. The advantages will be realized and attained by means of the elements and combinations particularly pointed out in the appended claims. It is to be understood that both the foregoing general description and the following detailed description are exemplary and explanatory only and are not restrictive, as claimed.

BRIEF DESCRIPTION OF THE DRAWINGS

The accompanying drawings, which are incorporated in and constitute a part of this specification, illustrate embodiments and together with the description, serve to explain the principles of the methods and systems:

FIGS. 4A-F illustrates segmentation of the NFL, GCL and combined layer of the OS and RPE from macular and peripapillary OCT volumes according to an aspect.

FIGS. 9A-D illustrates emergent two-dimensional patterns of nerve fiber bundle distribution in glaucoma according to an aspect.

FIGS. 10 and 10A illustrate a representation of an exemplary RGC-AC.

FIGS. 12A-D illustrates structural-functional correlations in advance glaucoma according to an aspect.

FIGS. 13A-E shows scatterplots of structure-VF correlation according to an aspect.

Figure 1:
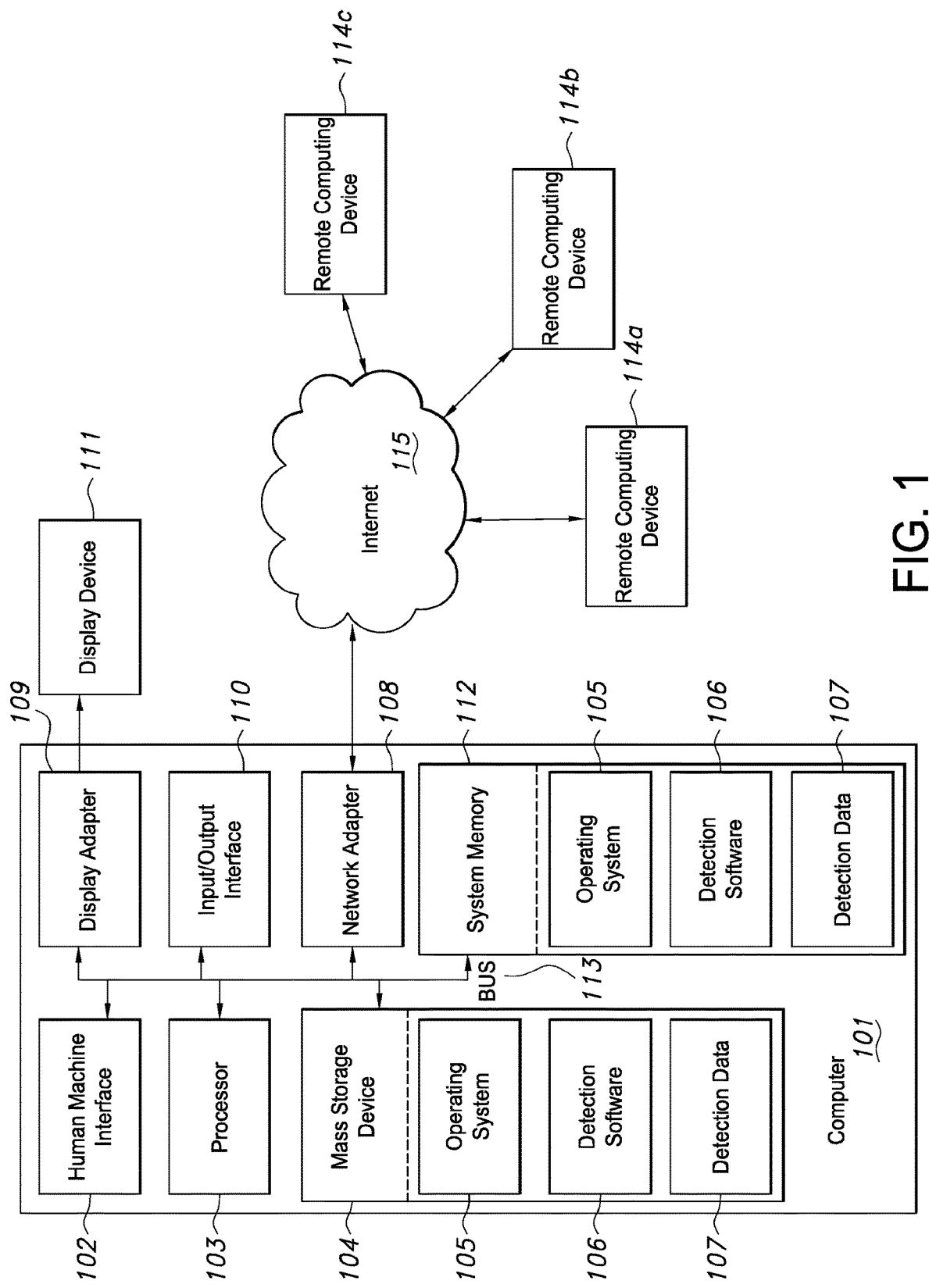
FIG. 1 is a block diagram of an exemplary computing system.
Figure 2B:
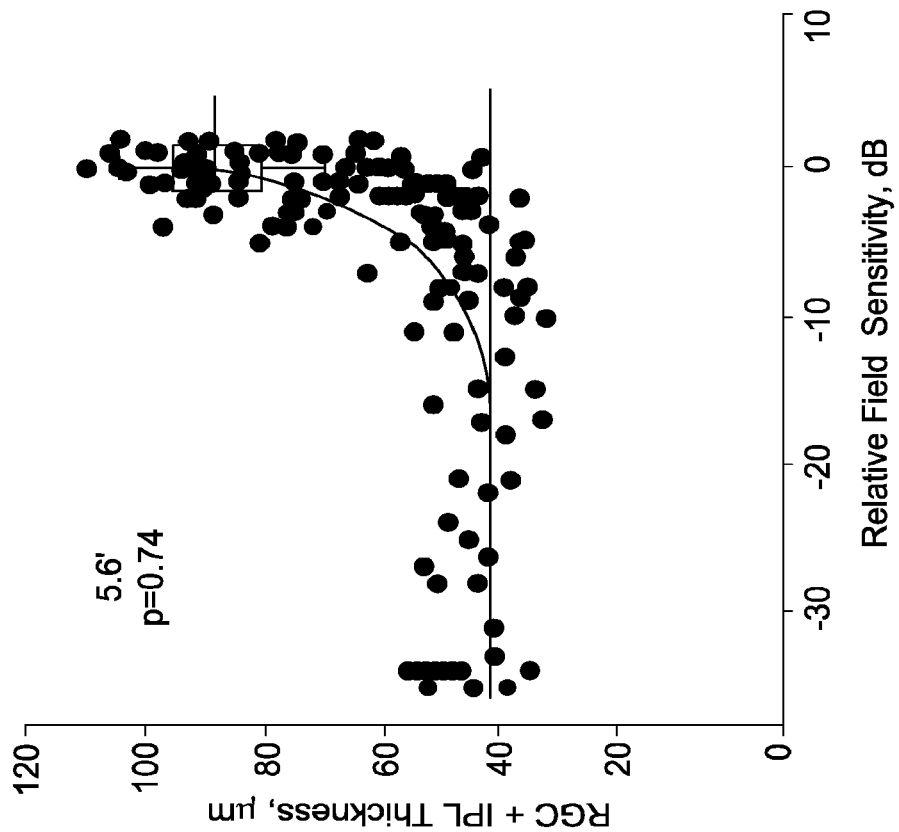
FIGS. 2a-c are exemplary graphs of VF-structural relationships.
Figure 2A:
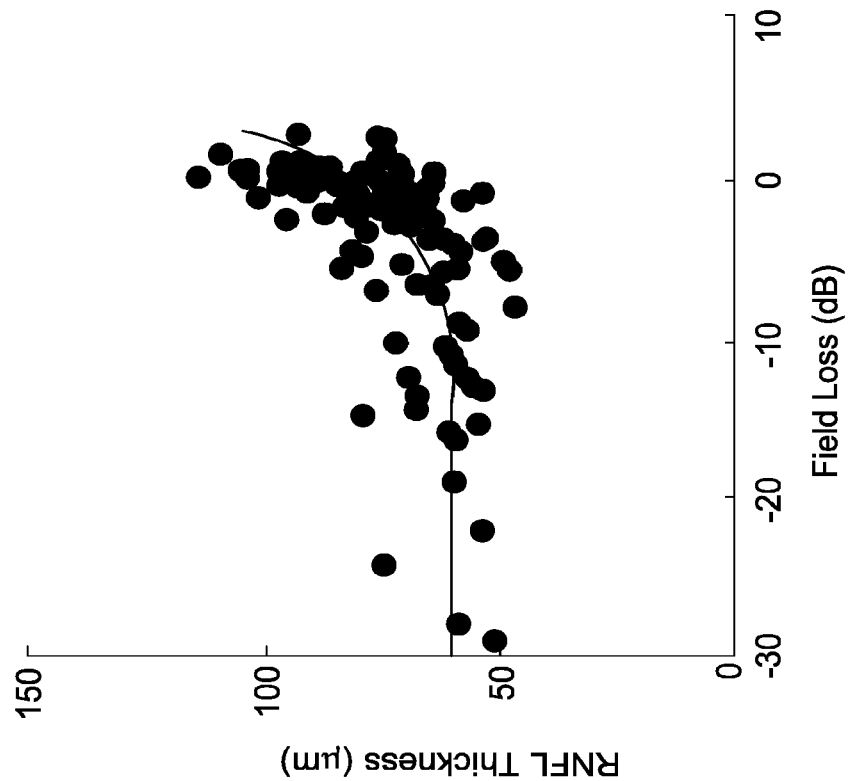
Figure 2C:
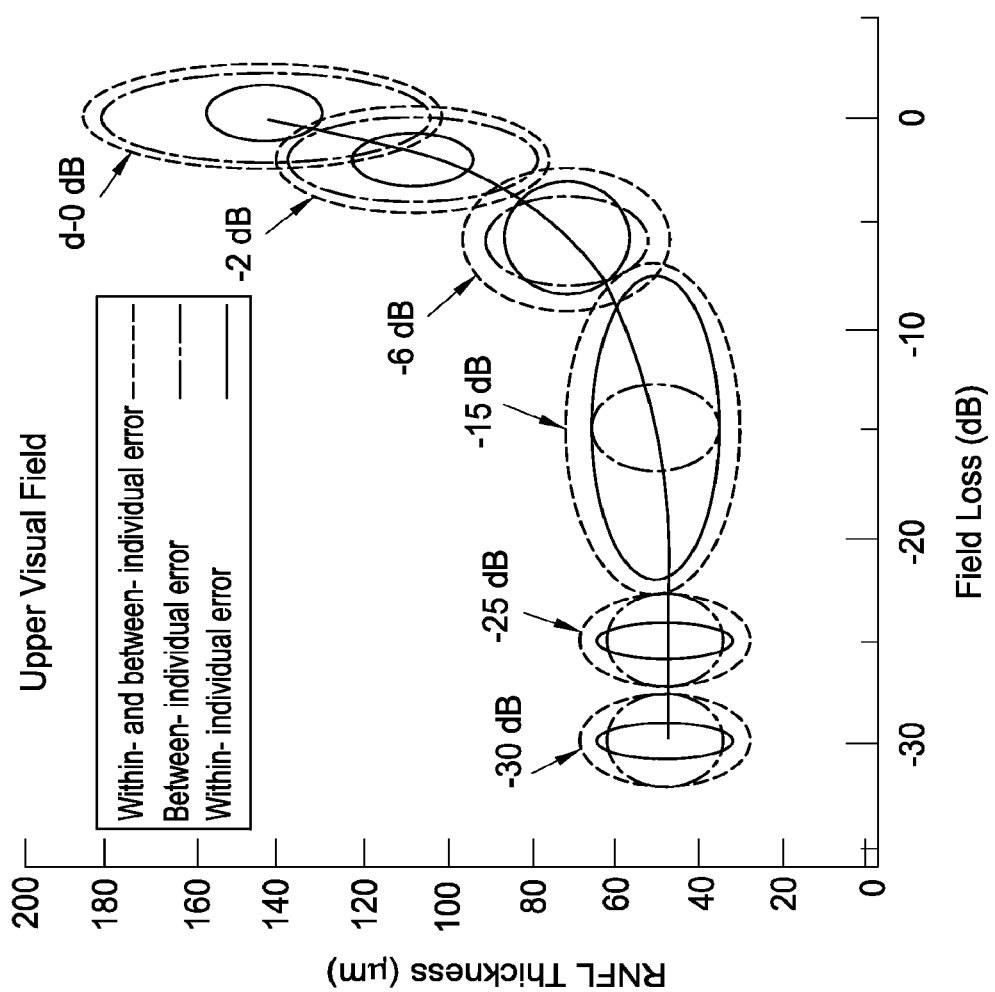

Additionally, Attachment A (9 pages), Attachment B (17 pages), and Attachment C (3 pages) each incorporated herein by reference in its entirety, include a multitude of drawings, tables, equations, raw data, and experimentation results which provide details and further understanding of various embodiments of the present invention.

DETAILED DESCRIPTION

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

Attachment A (9 pages) entitled "Distribution of Damage to the Entire Retinal Ganglion Cell Pathway" forms a portion of the Specification of the present application, and is hereby incorporated by reference herein in its entirety.

Attachment B (17 pages) forms a portion of the Specification of the present application, and is hereby incorporated by reference herein in its entirety.

Attachment C (3 pages) forms a portion of the Specification of the present application, and is hereby incorporated by reference herein in its entirety.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the examples included therein and to the Figures and their previous and following description.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

The methods and systems that have been introduced above, and discussed in further detail below, have been and will be described as comprised of units. One skilled in the art will appreciate that this is a functional description and that the respective functions can be performed by software, hardware, or a combination of software and hardware. A unit can be software, hardware, or a combination of software and hardware. The units can comprise the detection software 106 as illustrated in FIG. 1 and described below. In one exemplary aspect, the units can comprise a computer 101 as illustrated in FIG. 1 and described below.

FIG. 1 is a block diagram illustrating an exemplary operating environment for performing the disclosed methods. This exemplary operating environment is only an example of an operating environment and is not intended to suggest any limitation as to the scope of use or functionality of operating environment architecture. Neither should the operating environment be interpreted as having any dependency or requirement relating to any one or combination of components illustrated in the exemplary operating environment.

The present methods and systems can be operational with numerous other general purpose or special purpose computing system environments or configurations. Examples of well known computing systems, environments, and/or configurations that can be suitable for use with the systems and methods comprise, but are not limited to, personal computers, server computers, laptop devices, and multiprocessor systems. Additional examples comprise set top boxes, programmable consumer electronics, network PCs, minicomputers, mainframe computers, distributed computing environments that comprise any of the above systems or devices, and the like.

The processing of the disclosed methods and systems can be performed by software components. The disclosed systems and methods can be described in the general context of computer-executable instructions, such as program modules, being executed by one or more computers or other devices. Generally, program modules comprise computer code, routines, programs, objects, components, data structures, etc. that perform particular tasks or implement particular abstract data types. The disclosed methods can also be practiced in grid-based and distributed computing environments where tasks are performed by remote processing devices that are linked through a communications network. In a distributed computing environment, program modules can be located in both local and remote computer storage media including memory storage devices.

Further, one skilled in the art will appreciate that the systems and methods disclosed herein can be implemented via a general-purpose computing device in the form of a computer 101. The components of the computer 101 can comprise, but are not limited to, one or more processors or processing units 103, a system memory 112, and a system bus 113 that couples various system components including the processor 103 to the system memory 112. In the case of multiple processing units 103, the system can utilize parallel computing.

The system bus 113 represents one or more of several possible types of bus structures, including a memory bus or memory controller, a peripheral bus, an accelerated graphics port, and a processor or local bus using any of a variety of bus architectures. By way of example, such architectures can comprise an Industry Standard Architecture (ISA) bus, a Micro Channel Architecture (MCA) bus, an Enhanced ISA (EISA) bus, a Video Electronics Standards Association (VESA) local bus, an Accelerated Graphics Port (AGP) bus, and a Peripheral Component Interconnects (PCI), a PCI-Express bus, a Personal Computer Memory Card Industry Association (PCMCIA), Universal Serial Bus (USB) and the like. The bus 113, and all buses specified in this description can also be implemented over a wired or wireless network connection and each of the subsystems, including the processor 103, a mass storage device 104, an operating system 105, detection software 106, detection data 107, a network adapter 108, system memory 112, an Input/Output Interface 110, a display adapter 109, a display device 111, and a human machine interface 102, can be contained within one or more remote computing devices 114a,b,c at physically separate locations, connected through buses of this form, in effect implementing a fully distributed system.

The computer 101 typically comprises a variety of computer readable media. Exemplary readable media can be any available media that is accessible by the computer 101 and comprises, for example and not meant to be limiting, both volatile and non-volatile media, removable and non-removable media. The system memory 112 comprises computer readable media in the form of volatile memory, such as random access memory (RAM), and/or non-volatile memory, such as read only memory (ROM). The system memory 112 typically contains data such as detection data 107 and/or program modules such as operating system 105 and detection software 106 that are immediately accessible to and/or are presently operated on by the processing unit 103.

In another aspect, the computer 101 can also comprise other removable/non-removable, volatile/non-volatile computer storage media. By way of example, FIG. 1 illustrates a mass storage device 104 which can provide non-volatile storage of computer code, computer readable instructions, data structures, program modules, and other data for the computer 101. For example and not meant to be limiting, a mass storage device 104 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Optionally, any number of program modules can be stored on the mass storage device 104, including by way of example, an operating system 105 and detection software 106. Each of the operating system 105 and detection software 106 (or some combination thereof) can comprise elements of the programming and the detection software 106. Detection data 107 can also be stored on the mass storage device 104. Detection data 107 can be stored in any of one or more databases known in the art. Examples of such databases comprise, DB2®, Microsoft® Access, Microsoft® SQL Server, Oracle®, mySQL, PostgreSQL, and the like. The databases can be centralized or distributed across multiple systems.

In another aspect, the user can enter commands and information into the computer 101 via an input device (not shown). Examples of such input devices comprise, but are not limited to, a keyboard, pointing device (e.g., a "mouse"), a microphone, a joystick, a scanner, tactile input devices such as gloves, and other body coverings, and the like. Further examples can include image capturing devices, such as, but not limited to, optical coherence tomography capturing devices, fundus cameras, scanning laser ophthalmoscope, and other devices used to capture images and other information related to the monitoring and examination of eyes. These and other input devices can be connected to the processing unit 103 via a human machine interface 102 that is coupled to the system bus 113, but can be connected by other interface and bus structures, such as a parallel port, game port, an IEEE 1394 Port (also known as a Firewire port), a serial port, or a universal serial bus (USB), or network connection.

In yet another aspect, a display device 111 can also be connected to the system bus 113 via an interface, such as a display adapter 109. It is contemplated that the computer 101 can have more than one display adapter 109 and the computer 101 can have more than one display device 111. For example, a display device can be a monitor, an LCD (Liquid Crystal Display), or a projector. In addition to the display device 111, other output peripheral devices can comprise components such as speakers (not shown) and a printer (not shown) which can be connected to the computer 101 via Input/Output Interface 110. Any step and/or result of the methods can be output in any form to an output device. Such output can be any form of visual representation, including, but not limited to, textual, graphical, animation, audio, tactile, and the like.

The computer 101 can operate in a networked environment using logical connections to one or more remote computing devices 114a,b,c. By way of example, a remote computing device can be a personal computer, portable computer, a server, a router, a network computer, a wireless connected tablet or mobile device, a peer device or other common network node, and so on. Logical connections between the computer 101 and a remote computing device 114a,b,c can be made via a local area network (LAN) and a general wide area network (WAN). Such network connections can be through a network adapter 108. A network adapter 108 can be implemented in both wired and wireless environments. Such networking environments are conventional and commonplace in offices, enterprise-wide computer networks, intranets, cellular networks and the Internet 115.

For purposes of illustration, application programs and other executable program components such as the operating system 105 are illustrated herein as discrete blocks, although it is recognized that such programs and components reside at various times in different storage components of the computing device 101, and are executed by the data processor(s) of the computer. An implementation of detection software 106 can be stored on or transmitted across some form of computer readable media. Any of the disclosed methods can be performed by computer readable instructions embodied on computer readable media. Computer readable media can be any available media that can be accessed by a computer. By way of example and not meant to be limiting, computer readable media can comprise "computer storage media" and "communications media." "Computer storage media" comprise volatile and non-volatile, removable and non-removable media implemented in any methods or technology for storage of information such as computer readable instructions, data structures, program modules, or other data. Exemplary computer storage media comprises, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

The methods and systems can employ Big Data Analytics techniques such as statistical analysis, data mining, machine learning and iterative learning. Examples of such techniques include, but are not limited to, expert systems, case based reasoning, Bayesian networks, behavior based AI, neural networks, fuzzy systems, evolutionary computation (e.g. genetic algorithms), swarm intelligence (e.g. ant algorithms), and hybrid intelligent systems (e.g. Expert inference rules generated through a neural network or production rules from statistical learning).

In an aspect, systems and methods can provide segmentation of retinal layers from 3D SD-OCT images 10 and calculation of structural indices like thickness and texture in the peripapillary and the macular retinal regions. Accordingly, the system and methods can determine how GCL structural indices correlate with the NFL thickness. As an example, Macula- and ONH-centered SD-OCT volumes (Cirrus, Carl Zeiss Meditec, Inc., Dublin, Calif.) can be acquired (e.g., 2×2 volumes per subject), as illustrated in FIGS. 3-9. As illustrated, each SD-OCT volume can comprise 200×200×1024 voxels, corresponding to physical dimensions of 6×6×2 mm3. In other aspects, the SD-OCT volume can be comprised of voxels across a different range of dimension. As a further example, a mean NFL thickness on a circle with diameter 3.46 mm centered at the optic disc from the analysis provided by the manufacturer can be 77.3 (±13.9) μm. The mean NFL thickness can be determined over a wide range of areas in other aspects. The mean rim area and average cup-to-disc ratio, as provided by Cirrus, can be 0.97 (±0.30) mm2 and 0.65 (±0.14), respectively. In other aspects, other mean rim areas and cup-to-disc ratios can be utilized.

Figure 3:
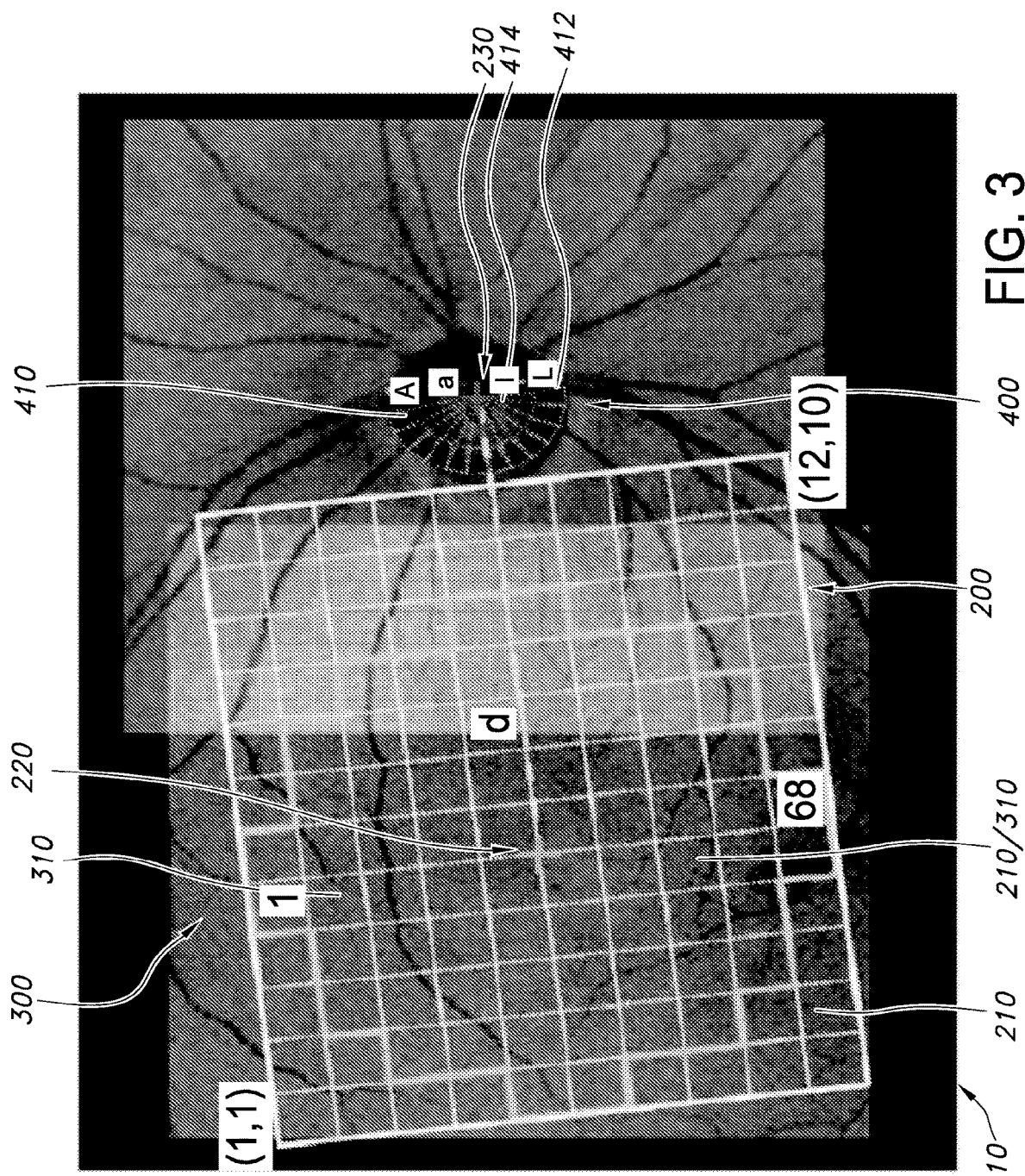
FIG. 3 illustrates an exemplary grid overlaying macular and ONH scans according to an aspect.

In an aspect, a plurality of grids 200, 300, 400 can be used to divide the macular 10 and ONH volume scans 20 into regions that are functionally and structurally relevant and suitable for analysis: the Nerve Fiber Bundle (NFB) grid 200, the Macular grid 300, and the ONH grid 400, shown in FIG. 3. As an example, the NFB grid 200, with one hundred twenty square NFB regions 210, is shown in white. A segment of NFB can be associated with one NFB region 210. To compensate for the individual differences in distance of fovea to optic disc, the size of the regions differs slightly between subjects, based on a scaling factor (d), wherein d (shown in yellow in FIG. 3) is defined as the distance between the location of the fovea 220 (shown at the green cross) and the center of the neural canal opening (NCO) 230 (shown at the red cross), for each individual subject. In this aspect, d is used as a parameter because it can be optimized. However, in other aspects, the scaling factor can be based upon other distances between different locations, or other criteria.

The width and height of the NFB grid 200 is defined in terms of d, 7.2 mm×(⅔)d mm/3.0 mm and 6.0 mm×(⅔)d mm/3.0 mm, where (⅔)d mm/3.0 mm is a ratio, respectively. Other ratios can be used based upon the specific visual field is used for the correlation. The macular grid 300 can comprise a subset of 68 regions 310 of the NFB grid 200 and resembles the 10-2 Humphrey visual field grid; it is shown in cyan. Since the NFB and GCL structures reside in some of the same portions of the eye, the NFB grid 200 and the macular grid 300 overlap, with all of the macular grid regions 310 corresponding to some of the NFB grid regions 210. The ONH grid 400, centered on the NCO center 230, can comprise 12 wedge-like regions 410, each subtending 15° rim regions are shown in green. In an aspect, the ONH grid regions 410 can be subdivided further into outer ONH grid regions 412 shown in green (parts of rim), and inner ONH grid regions 414, shown in orange (parts of cup). Grids 200, 300, 400 can be slightly rotated based on the axis between fovea 220 and NCO center 230, which decreased thickness variability in preliminary studies.

In an aspect, segmentation of intraretinal layers through the use of macular volumes 20 and peripapillary OCT volumes 30 can be automated. For example, a graph search segmentation application can be used to segment the layers of the volumes. In other aspects, the methods and systems discussed in U.S. Pat. Nos. 7,995,810 and 8,358,819, both entitled "System and Methods for Image Segmentation in N-Dimensional Space", and both of which are incorporated in their entirety by this reference herein, can be used to carry out the segmentation. As an example, within each of the macular volumes 20, eleven surfaces can be segmented in three dimensions using a graph-theoretic approach. As an example, a plurality (e.g. five) of the surfaces, as labeled in FIGS. 4(A-F), can be used to identify the intraretinal layers 500, and more specifically the NFL 502 (between surface 1 shown in red and surface 2 shown in green), the GCL 504 (between surface 2 and surface 3 shown in yellow), and the combined layer 506 of the outer segment (OS) and retinal pigment epithelium complex (RPE) (between surface 7 shown in orange and surface 11 shown in cyan). In other aspects, various segmentations (i.e., identifying a layer between the identified surfaces) can be used to identify other layers.

Figure 4B:
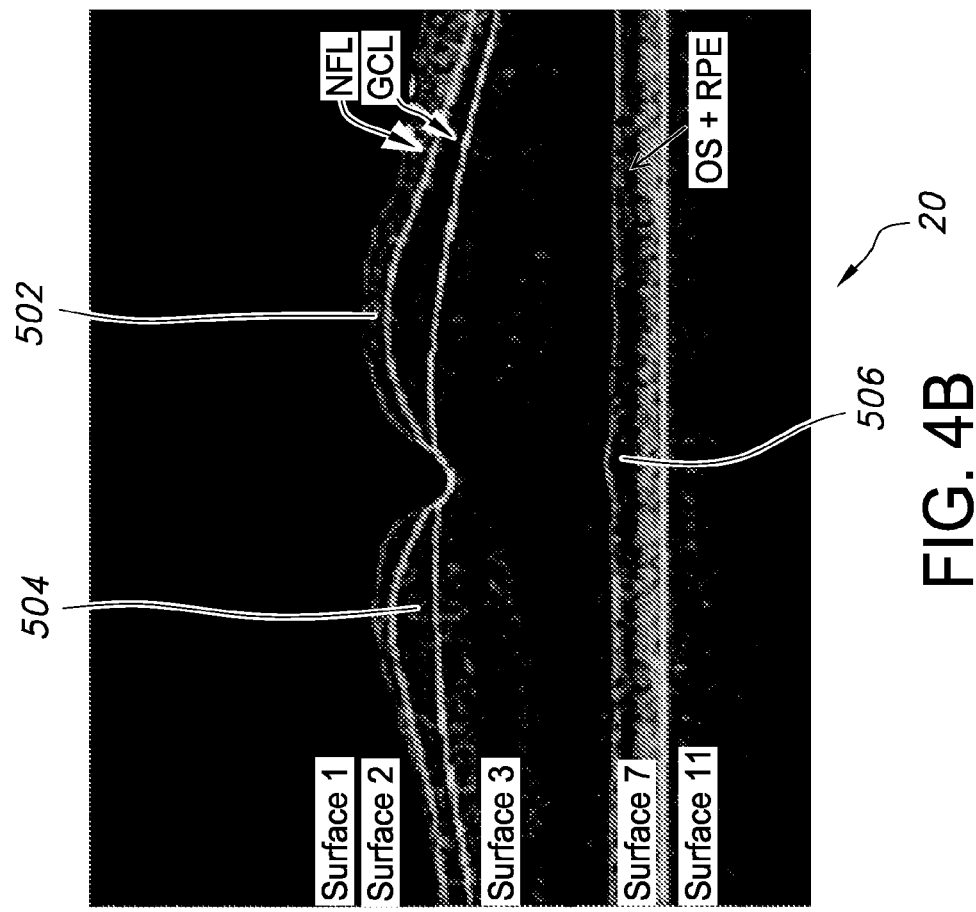
Figure 4A:
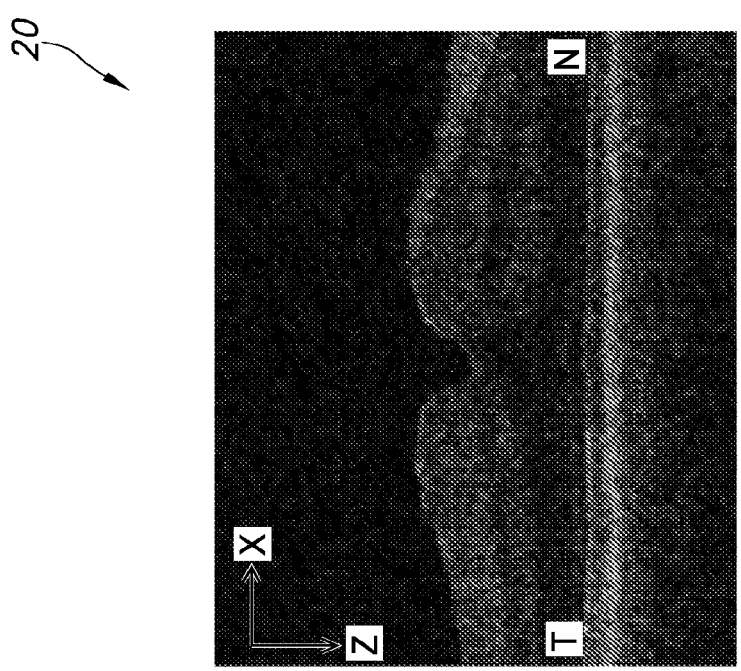

FIGS. 4(A-F) illustrate segmentation of the NFL 502, the GCL 504 and the combined layer 506 of the OS and RPE from macular OCT volumes 20 and peripapillary OCT volumes 30. FIG. 4(A) illustrates a flattened and cropped B-scan image of the macular OCT volume 20. T represents the temporal side of the macular OCT volume 20, whereas N represents the nasal side of the macular OCT volume. FIG. 4(B) illustrates the cropped B-scan image of FIG. 4(A) overlapped with the layer segmentation results that illustrate the NFL 502 between surfaces 1 (shown in red) and 2 (shown in green), the GCL 504 between surfaces 2 (green) and 3 (shown in yellow), and the combined layer 506 of the OS and RPE between surfaces 7 (shown in orange) and 11 (shown in cyan). FIG. 4(C) illustrates a 3-D rendering 40 of the surfaces segmented in image FIG. 4(B). The NFL 502 can be found between surfaces 1 (red) and 2 (green), the GCL 504 can be found between surfaces 2 (green) and 3 (yellow) and the combined layer 506 of the OS and RPE between surfaces 7 (orange) and 11 (cyan) of the macular OCT volume 20.

FIGS. 4(D-F) illustrate peripapillary OCT volumes 30. As discussed above, a plurality (e.g. five) of the surfaces can be used to identify the intraretinal layers 500, and more specifically the NFL 502 (between surface 1 shown in red and surface 2 shown in green), the GCL 504 (between surface 2 and surface 3 shown in yellow), and the combined layer 506 of the outer segment (OS) and retinal pigment epithelium complex (RPE) (between surface 7 shown in orange and surface 11 shown in cyan). FIG. 4(D) illustrates a flattened and cropped B-scan image of a peripapillary OCT volume 30. T represents the temporal side of the peripapillary OCT volume 30, whereas N represents the nasal side of the peripapillary OCT volume 30. FIG. 4(E) illustrates the cropped B-scan image (D) of FIG. 4(D) overlapped with the layer segmentation results of the peripapillary OCT volume 30, with the NFL 502 between surfaces 1 and 2, the GCL 504 between surfaces 2 and 3, and the combined layer 506 of the OS and RPE between surfaces 7 and 11. FIG. 4(F) illustrates a 3-D rendering 40 of the surfaces segmented in image FIG. 4(E). The NFL 502 can be found between surfaces 1 (red) and 2 (green), the GCL 504 can be found between surfaces 2 (green) and 3 (yellow) and the combined layer 506 of the OS and RPE between surfaces 7 (orange) and 11 (cyan) in the peripapillary OCT volume 30.

Figure 5B:
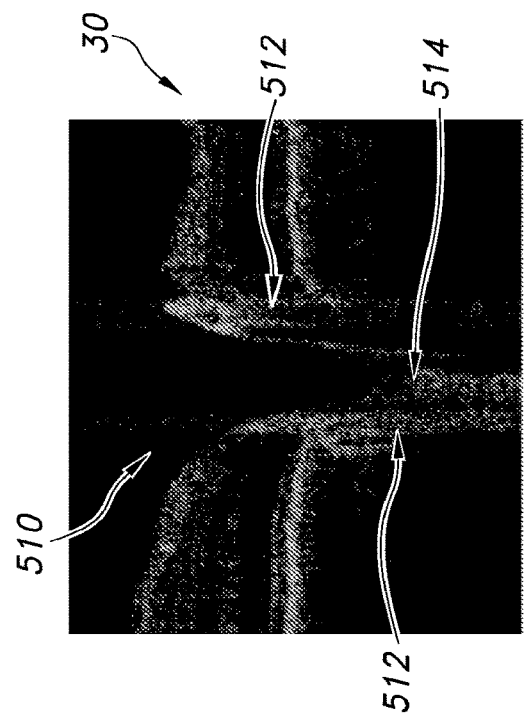
FIGS. 5A-C illustrate segmentation results of the optic cup, neuroretinal rim, and NCO from the peripapillary OCT volume in the B-scan and projection images.
Figure 5C:
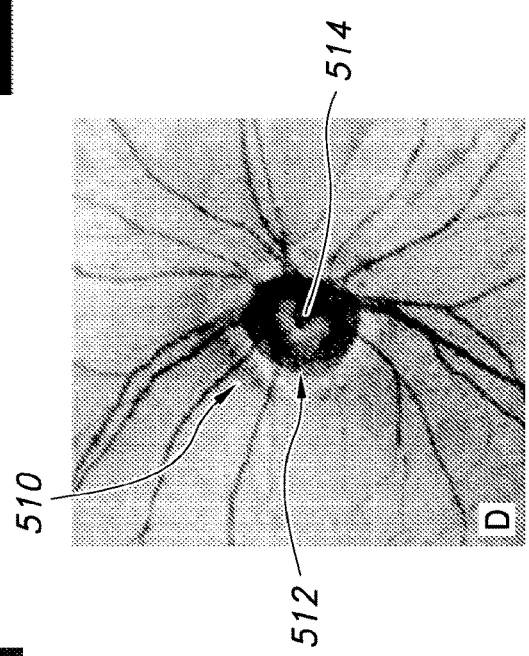
Figure 5A:
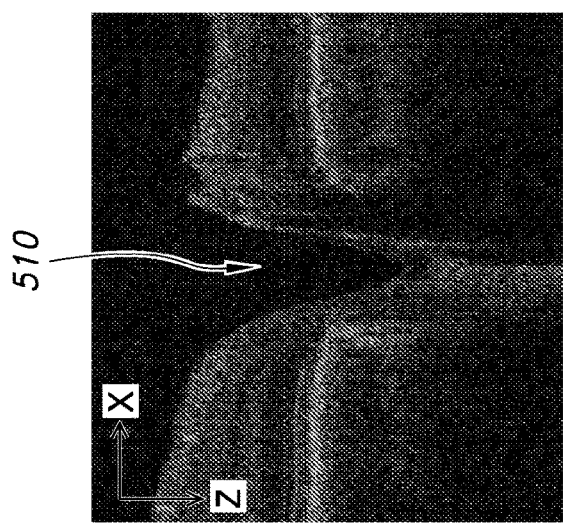

In an aspect, one or more ONH grid parameters can be quantified. As an example, within each ONH-centered OCT volume 10, the NCO 510 can be segmented by finding the boundary at the level of retinal pigment epithelium (RPE)/Bruch's membrane (BM) complex using a 2-D graph search method. FIGS. 5A-D illustrates an aspect of the segmentation of the NCO 510 using the peripapillary OCT volume 30. The ONH rim tissue surface projection 512 and the optic disc cup 514 can be detected by a voxel column classification algorithm using features of retinal morphology and OCT voxel intensities. The final neuroretinal rim 512 was estimated by excluding the cup area 514 from the NCO area 510. An OCT projection image was created by averaging in the z-direction (A-scan) the combined layer 506 of the OS and RPE subvolume between surfaces 7 and 11, as shown in FIGS. 5C-D.

FIGS. 5A-D shows segmentation results of the optic disk cup 514, neuroretinal rim 512, and NCO 510 from the peripapillary OCT volumetric region 30 in the B-scan. The fovea location 220 (shown in FIG. 3) was estimated as the A-scan with the smallest distance between surfaces 1 and 7, in the z-direction; the center of the NCO 510 was estimated as its centroid. The regional mean rim width was calculated by averaging the distances between the inner and outer rim boundaries in the ONH or in a subset of ONH grid regions 410. The regional rim area is the area of the rim in each ONH grid region 410. The regional rim volume was the OCT subvolume in the neuroretinal rim segmentation between surface 1 (internal limiting membrane, ILM) and the reference surface fitted to surface 11 (the outer boundary of the RPE) (including the NFL 502, the GCL 504, and the combined OS and RPE layer 506) excluding the NCO region 510. The regional cup-to-NCO ratio, another regional property that can be used to identify the structural-functional relationship, was calculated by dividing the regional optic cup area by the sum of the regional optic cup and neuroretinal rim areas.

In an aspect, one or more of the GCL and NFB grid parameters can be quantified. As an example, the mean macular GCL thickness and NFL thickness for each macular respectively NFB grid region 110 can be estimated from registered macular and peripapillary OCT volumes 10, 20, 30 using the macular grid 300 and NFB grid 200 respectively. The regional mean GCL thickness can be measured by averaging the GCL 504 thickness for all A-scans in a grid region 310 and similarly for the NFL 502. The regional mean thickness of the GCL 504 and NFL 502 in regions that overlap, in both macula OCT volumes 10 and ONH OCT volumes 20, can define the average of the regions in both volumes after registration.

In an aspect, the connectivity of the ganglion cell layer 504 to ONH neural rim 512 can be mapped. In an example of the mapping, the GCL 504 is assumed to be connected to the RGC-AC within the ONH 510, with ONH RGC-AC making up the neural rim 512. For each macular grid region 310, the correlation of the thickness of the GCL 504 with the rim area 412 of each of the 12 ONH wedge-shaped regions 410 can be determined. The ONH grid region 410 that has the highest correlation can be selected: formally, for each of the 68 local macular regions 310 on the grid 300, the squared Pearson's correlation coefficients (r2) of thickness of GCL 504 with each of the 12 ONH wedge shaped regions 410 are calculated. The Pearson's correlation coefficient is done for the rim width, rim area, rim volume, and cup to NCO ratio of each ONH wedge shaped regions 410. Each wedge shaped region 410 of the ONH grid 400 that measures the highest r2 can be selected as the ONH wedge region 410 most closely associated with the damage to the GCL 504 of a macular region grid 310 under study. The connectivity map can be created by displaying each of the 12 ONH wedge regions 410 with a separate color, and coloring each of the 68 macular regions 310 with the color of the ONH wedge region that corresponds.

In an aspect, the connectivity of GCL to initial NFB segment and final NFB segment to ONH neural rim can be mapped. As an example, an RGC-AC cell body segment in the GCL 504 is assumed to be connected to at least one 'nearby' initial RGC-AC segment of NFB in the NFB grid 200, the NFB being located in the NFL 502. Since the macula grid 300 and the NFB grid 200 overlap, the initial RGC-AC segment of NFB may be located in either the macula grid 300 or the NFB grid regions 210 not shared with the macular grid regions 310. A single RGC-AC segment of NFB may be connected to multiple GCL regions. Further, it is assumed that the final RGC-AC NFB segment found in the macula grid 300 is connected to a RGC-AC segment within the ONH (which makes up the neural rim 512). For each GCL region 210/310, the correlation of the thickness of the NFL 502 in the neighboring NFB regions 210/310 can be determined. The NFB region 210/310 with the maximal correlation can be selected. In other words, for each region 310 in the macular grid 300, its association with the 25 closest NFB regions 210 can be tested, determining the maximum r2 between each regional mean GCL thickness and its 5×5 neighbor regional mean NFL thicknesses; formally, the region at path of neighboring NFB regions (i.e., RGC-AC segments) that had the highest cumulative correlation out of all possible RGC-AC paths. In the exemplary aspect, the most nasal regions were excluded from this computation due to the difficulty in verifying VF for such areas. In other aspects, the most nasal areas can be included in the computation. As an example, an A-graph search method can be used (e.g., which is capable of finding an optimal path with the minimum 'cost' (highest r2) from a starting node to one of ending nodes). Each region 210 of the NFB grid 200 can represent a 'node' in the graph, starting nodes were node and 0.160 (±0.075) respectively.

Figure 6A:
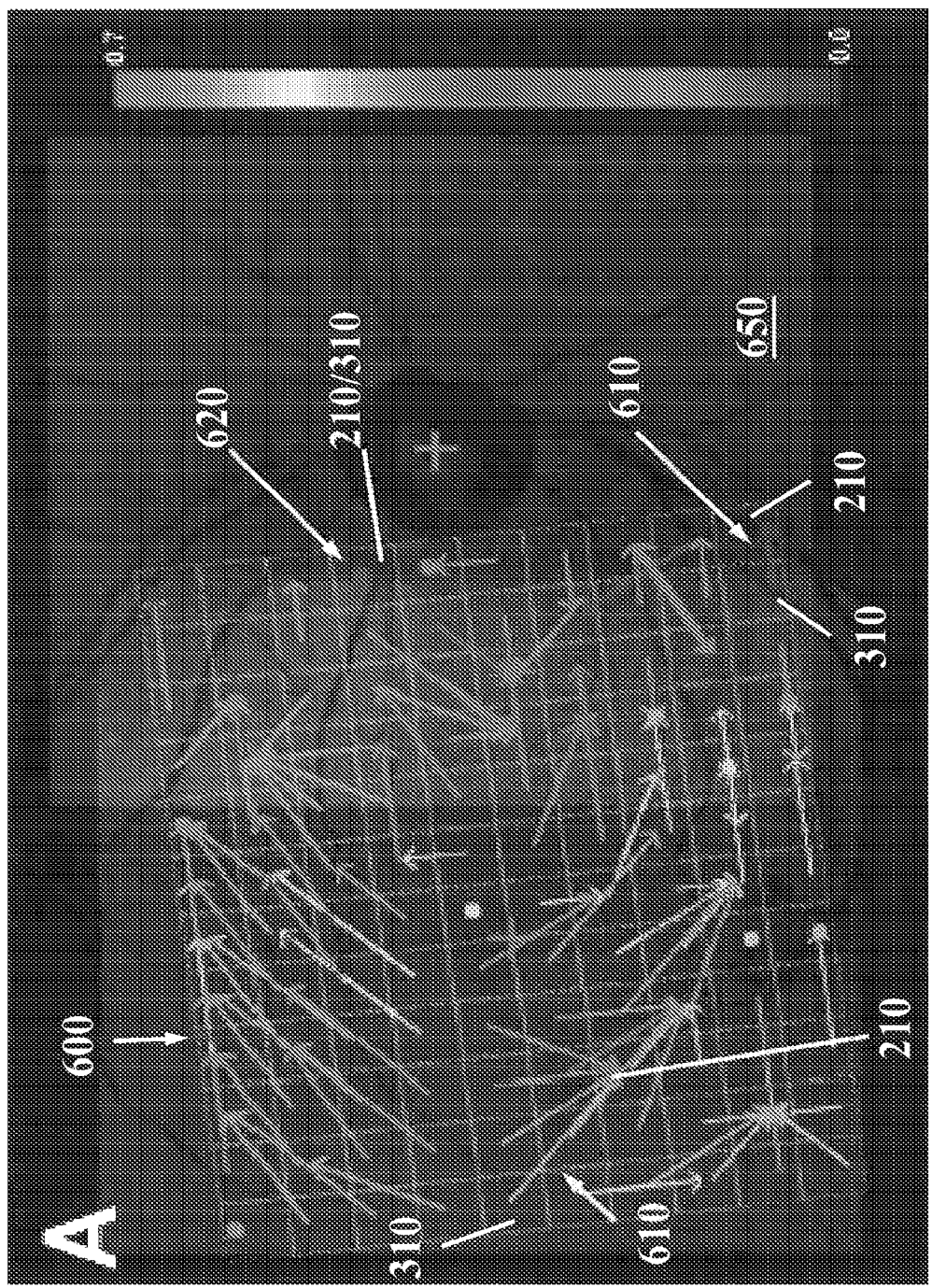
FIGS. 6A-6E illustrate exemplary emergent connectivity RGC-AC maps overlaid on a registered projection image from a single subject according to an aspect.

As an example, FIGS. 6A-6E illustrate emergent connectivity RGC-AC maps 600 overlaid on a registered projection image 650 from a single subject. FIG. 6A illustrates connectivity from macular GCL regions 310 to 'close' initial NFB regions 210. The arrow 610 starting in each macular grid region 310 ends at that one of 5×5 neighboring NFB grid regions 210 that exhibits the maximum Pearson's r2 correlation coefficient as indicated by the color of the arrow 610. Therefore, the beginning of the arrow 610 is associated with a macular region 310 of the macular grid 300, and terminates in an NFB region 210 of the NFB grid 200. A dot 620 located in a specific grid square 210/310 denotes that the highest correlation was between the macular and NFB regions 210/310 in the same location.

Figure 6B:
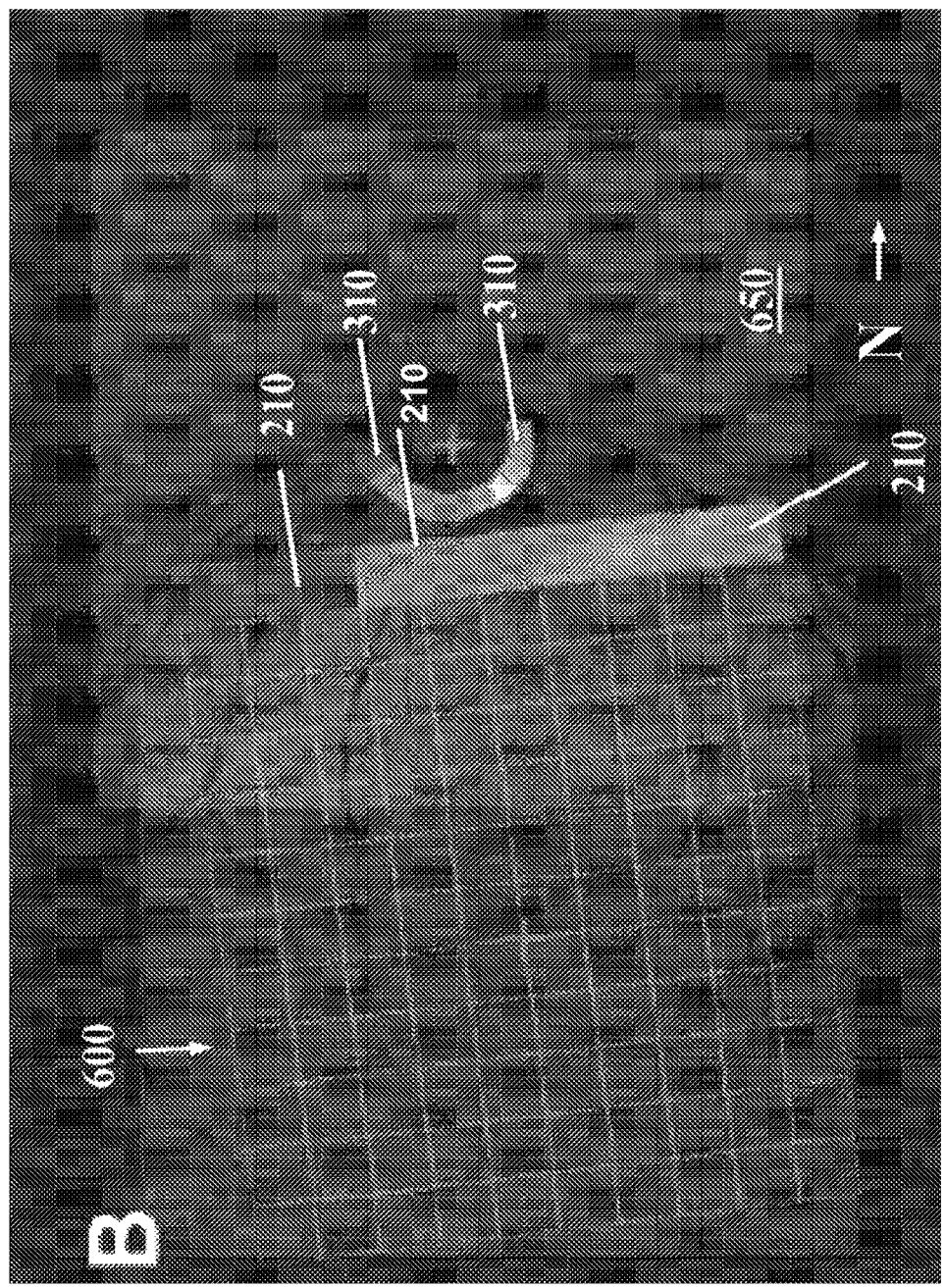
Figure 6C:
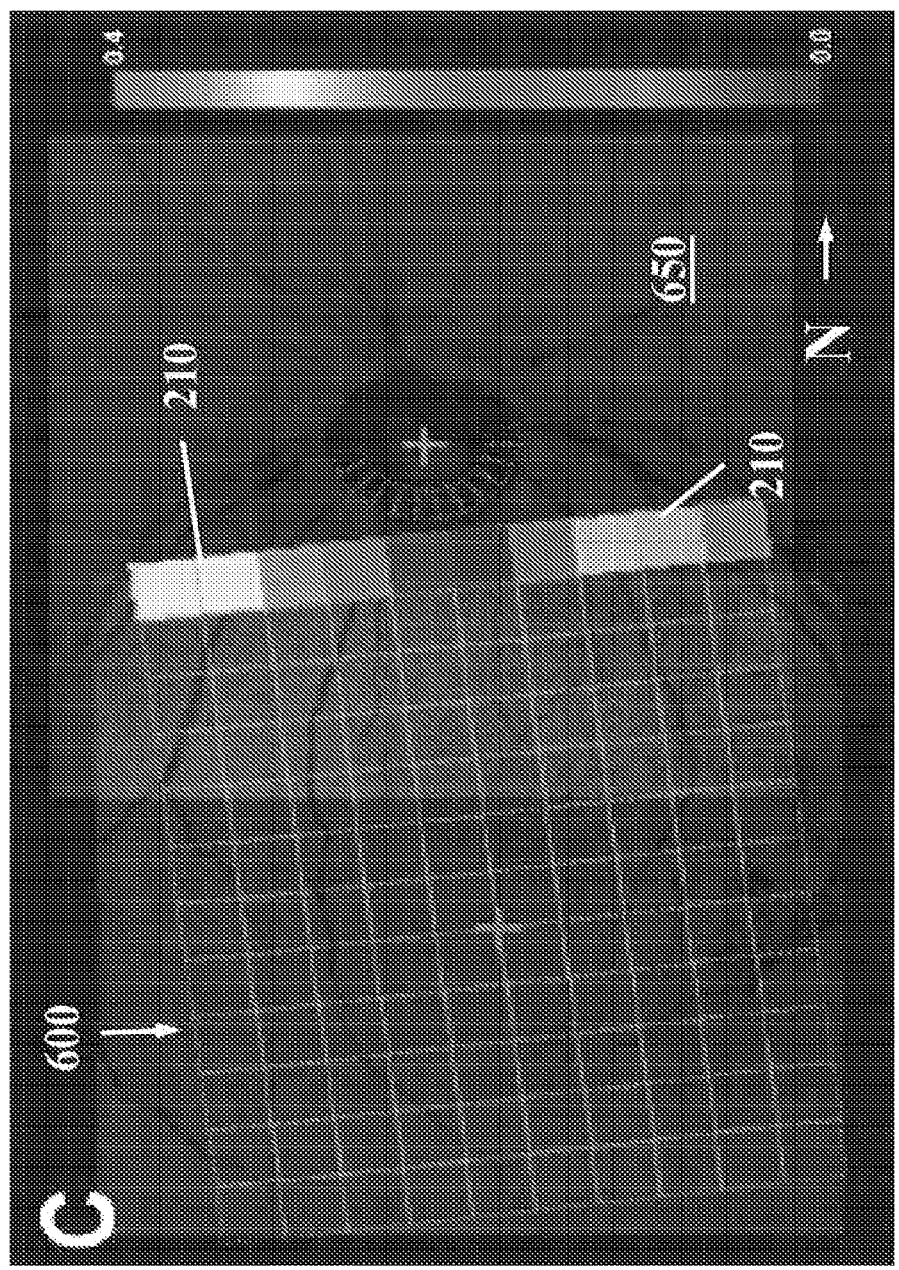

FIG. 6B illustrates connectivity from the most nasal NFB regions 210 to ONH wedge regions 410. The NFB region 210 and ONH wedge region 410 exhibiting the maximum r2 are coded with the same color. FIG. 6C is similar to FIG. 6B. However, instead of representing the connection, the pseudo-colors display their maximum r2 correlation coefficient likely reflecting connectivity paths between the most nasal NFB regions 210 and specific locations of the ONH rim regions. The correlation strength reflects the color displayed, with red representing the strongest and blue representing the lowest correlation thus reflecting the strength of connectivity between the NFB regions 210 and rim subregions.

Figure 6D:
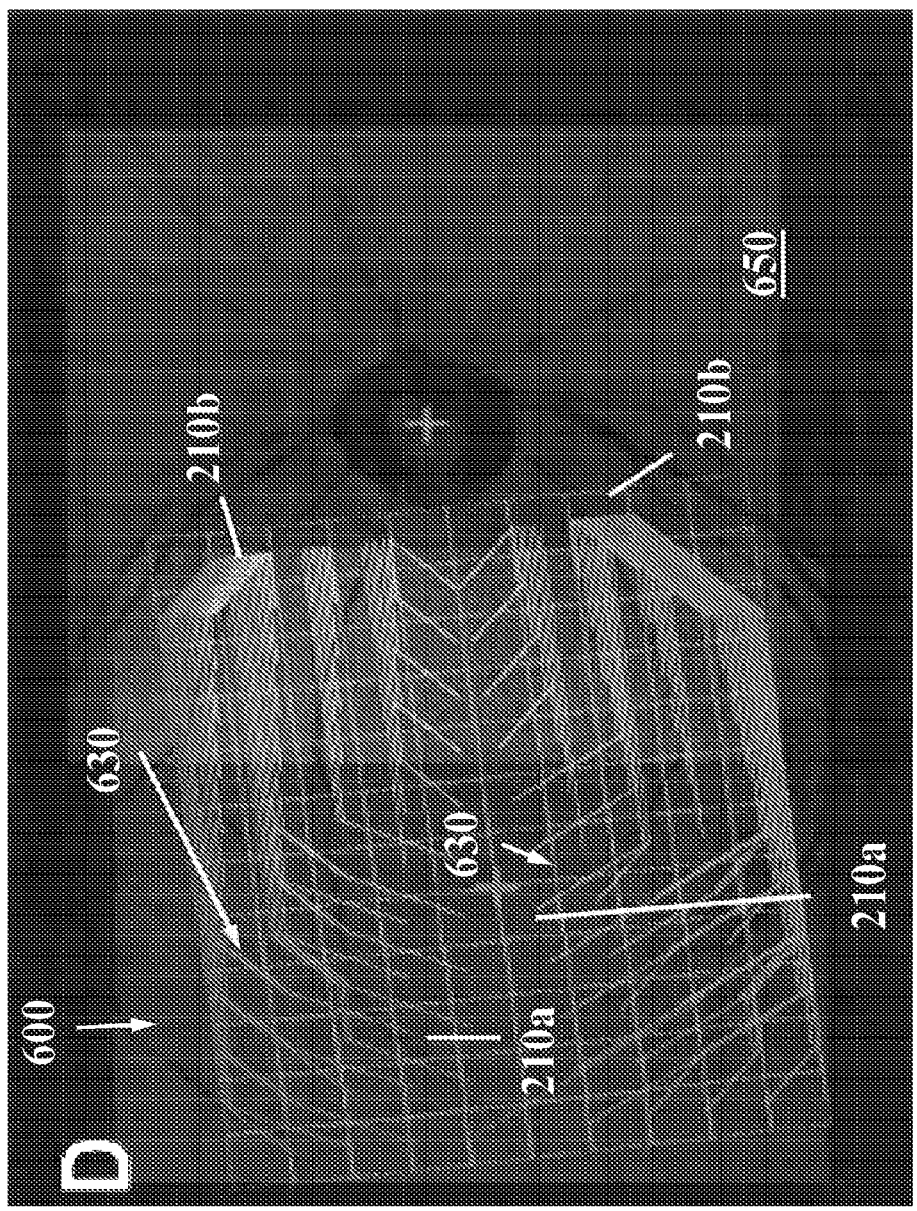
Figure 6E:
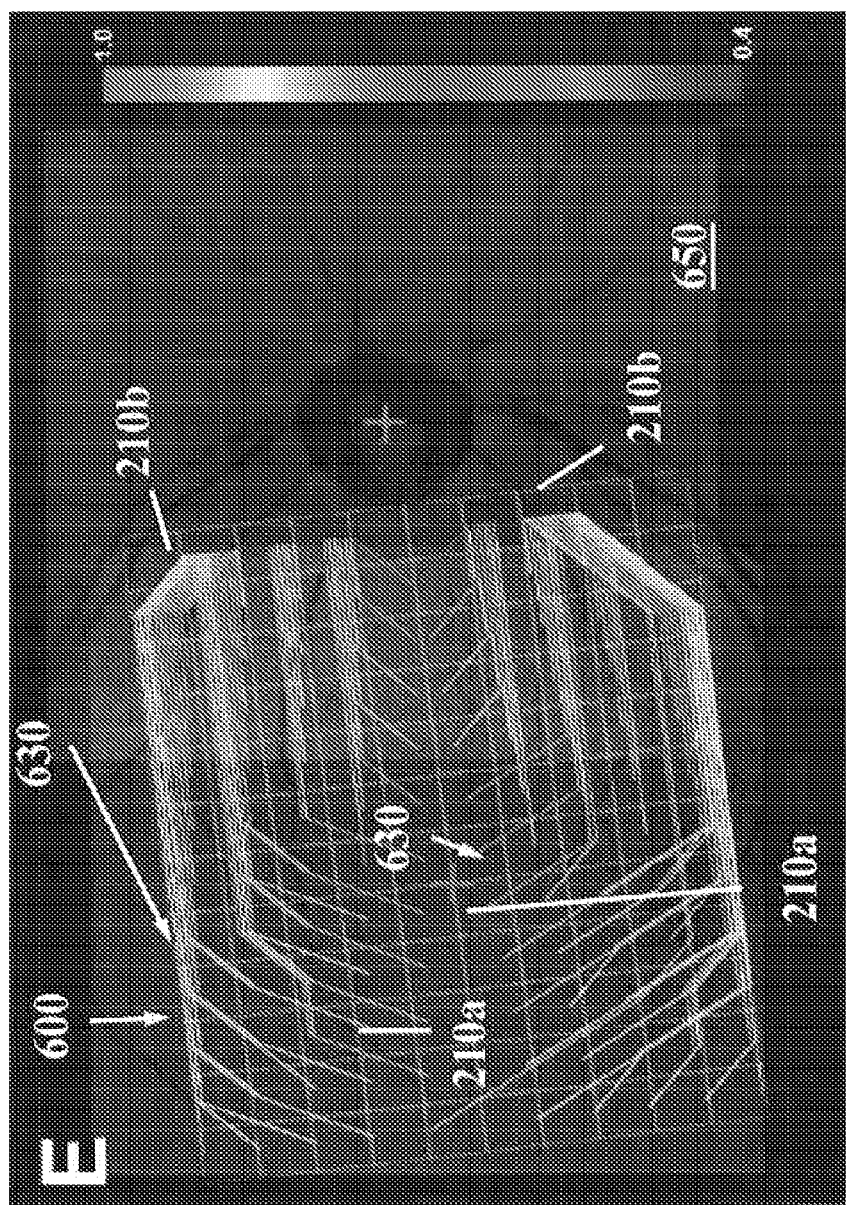
Figure 7:
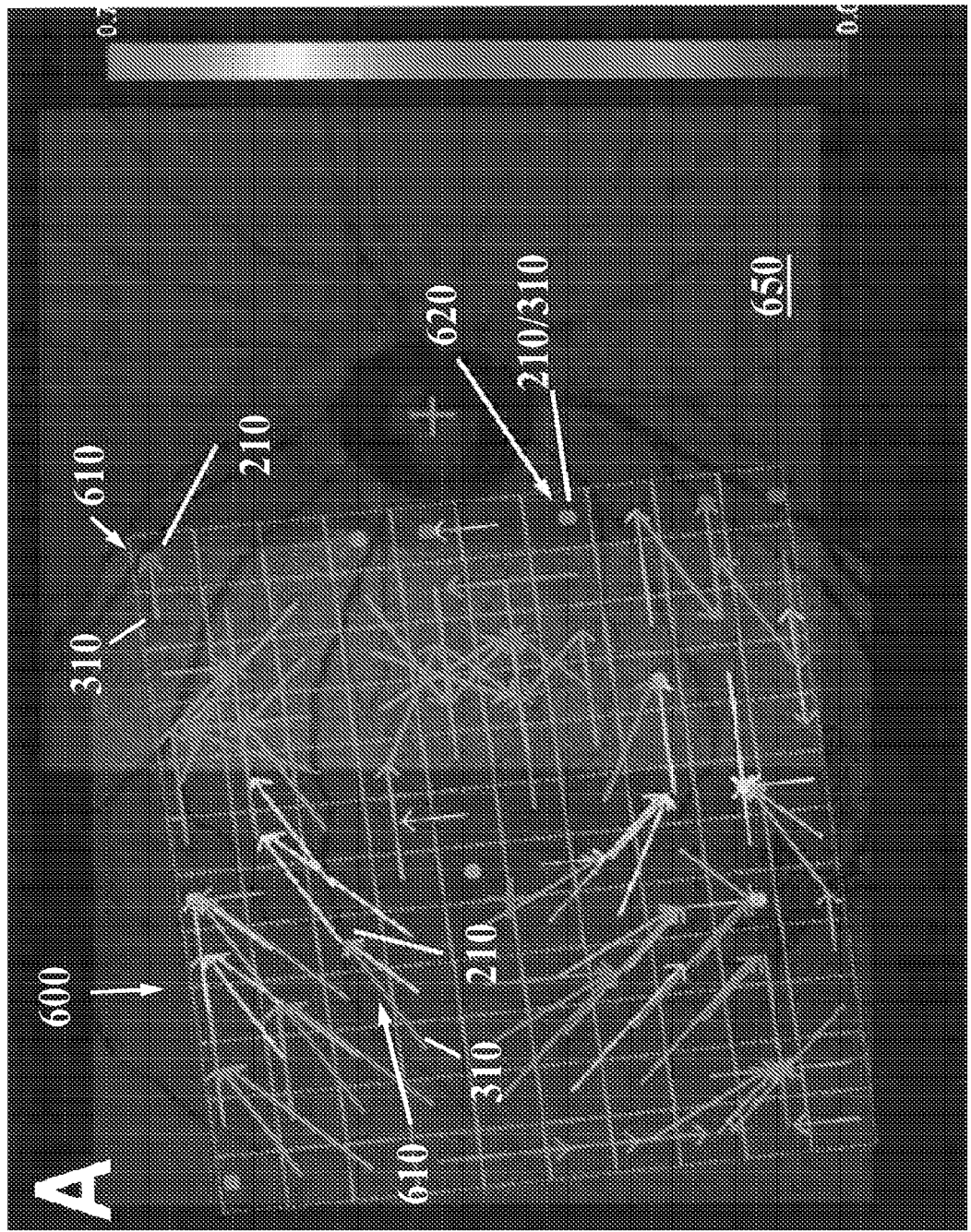
FIG. 7 illustrate exemplary emergent connectivity RGC-AC maps obtained from a set of left eyes only.

FIG. 6D illustrates connections of individual NFB regions 210 (RGC-AC segments in the NFL 502), from initial (anywhere in NFB grid 200) to most nasal NFB grid regions 210. A line 630 starting from each NFB grid region 210a (except the most nasal regions) and ending at one of the most nasal NFB regions 210b is the minimum cost path, or the highest overall correlation among all possible NFB segment NFL thicknesses. The color of the line 630 represents the starting position in the NFB grid 200, showing where the connection of the RGC-AC begins and where it ends. In an aspect, the lines 630 at the top and bottom boundaries of the NFB grid 200 can fall outside of the grid 200 because information is available outside the registered SD-OCT scans. FIG. 6(E) is similar to FIG. 6(D), but with the color of the line 630 displaying the aggregate Pearson's r2 correlation coefficient of the NFB region NFL thicknesses, indicating the amount of damage found along the regions 210.

In an aspect, glaucoma retinal ganglion cell body damage is accompanied by corresponding nerve fiber and optic nerve head axonal loss. In addition, the amount and distribution of glaucomatous damage along the entire retinal ganglion cell body-axonal complex (RGC-AC) can be quantified and mapped using automated analysis of standard commercially available SD-OCT.

As an example, RGC-AC connectivity maps (as shown in FIGS. 6A-E) emerge 'spontaneously' using the disclosed methods with minimal assumptions as discussed above based on rudimentary retinal anatomy. These emergent structural maps display the course (i.e., the arrows 610, dots 620 and lines 630 found in the NFB regions 210, macular (or GCL) region 310, and ONH region 410) of the RGC-ACs from their origin in a region of the retinal ganglion cell layer 504, following a specific course along the NFB in the NFL 502, and ending up in a specific region 410 of the ONH 510 (the limit of the visibility on SD-OCT). They are highly suggestive of the same distribution of nerve fiber bundles as established from histology of stained retina and from patterns of visual field defects (NFB only). The map can be constructed purely from structure to structure thickness correlations along the RGC-AC using only the following assumptions: a) the segment of the RGC-AC that is in the GCL 504 projects to a limited number (25) of close NFL regions; b) the NFB segments of the RGC-AC each connect to at least one neighboring segment c) the most nasal NFB segments of the RGC-AC are connected to the segment of the RGC-AC that is in the ONH.

In an aspect, the structure to structure correlation within the RGC-AC can be larger in the glaucoma subgroup than in the glaucoma suspect subgroup. One explanation is that as glaucoma advances, tissue loss and thinning also progress, leading to increasing structure to structure correlation as additional RGC-ACs are damaged by the disease. The emergence of the connectivity maps from glaucomatous damage support the notion that the RGC-AC manifests damage along its entire retinal pathway, i.e. all segments.

In an aspect, the method described above suggests that if the ganglion cell bodies in a specific RGC-AC are affected, the axonal segments that form the retinal NFB are also affected, as is the segment within the ONH, because otherwise the connectivity would not emerge from our correlation analysis. The method also suggests, according to an exemplary aspect, that the damage appears to be limited to specific RGC-ACs (the RGC-NFB-ONH paths), while others remain intact, at least in our patient cohort with early stage of the disease (MD of −1.90 dB and PSD of 3.29 dB).

In an aspect, when OS or OD images were analyzed independently, the obtained patterns were similar to those in FIG. 6, but exhibited higher level of noise. Comparison of OS (left side eye) vs. OU (left and right eyes) results (FIG. 7), shows that utilizing both eyes instead of either one did not change the general form of the relationships between macular grid regions 310 (representing the GCL layer 504) and the NFB regions (NFL 502), but clearly contributed to less noisy correlations.

In an aspect, in glaucoma suspects and early glaucoma, retinal ganglion cell body damage is accompanied by corresponding nerve fiber and optic nerve head axonal loss. The amount and distribution of glaucomatous damage along the entire retinal ganglion cell body-axonal complex (RGC-AC) can be quantified and mapped using automated analysis of standard, clinical, SD-OCT. The disclosed systems and methods can contribute to a better detection and improved management of glaucoma.

In another aspect, the present systems and methods can provide a highly reproducible automated graph-based simultaneous 11 surface segmentation of individual OCT image fields. As an example, 11-surface segmentation now takes about 2 minutes per OCT field volume on a standard PC. 14-subject repeat imaging-and-segmentation reproducibility was excellent 0.53 µm±0.31 µm (1.89%±0.74%) considering all 10 layers. For the GCL 504 and NFL 502, the reproducibilities were 1.08 µm±0.78 µm (2.75%±1.96%), and 0.42 µm±0.34 µm (1.36%±1.18%), respectively. This reproducibility is better than the achievable 5 µm A-scan resolution of SD-OCT.

Figure 8B:
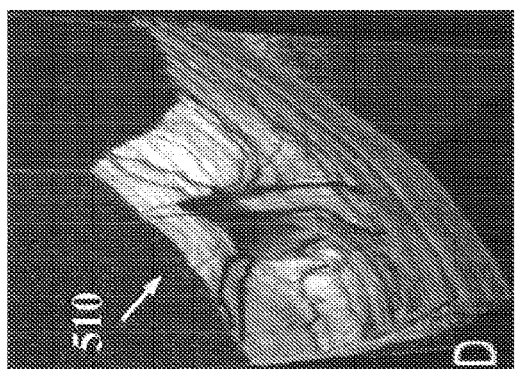
FIGS. 8A-D illustrate Macular and PP OCT multi-layer segmentation according to an aspect.
Figure 8D:
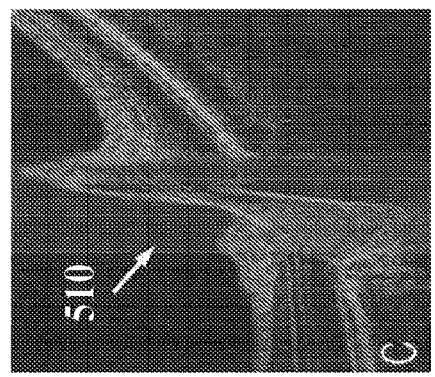
Figure 8A:
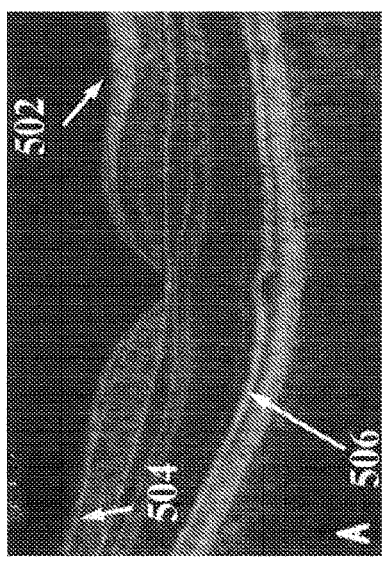
Figure 8C:
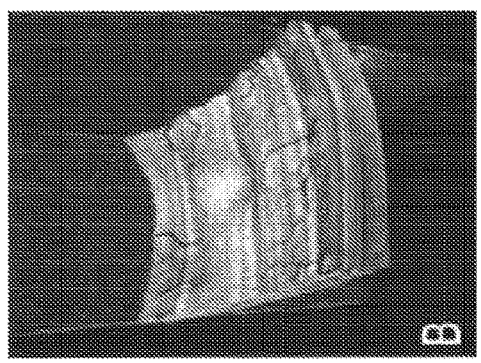

In an aspect, the present systems and methods can provide a highly reproducible automated segmentation of the tissue of the neural rim 512 and cup 514 of the optic nerve 510 in normal and glaucoma patients, using voxel classification/graph based three-dimensional algorithms, as shown in FIGS. 8A-D. In an exemplary aspect of the method and system, repeat-imaging study of 56 glaucoma patients, re-analysis reproducibility was high, namely 0.06 mm2±0.06 mm2 (5.79%±4.94%) for rim area segmentation, 0.10 mm2±0.08 mm2 (5.05%±4.50%) for disc area, 0.13 mm2±0.18 mm2 (6.47%±9.05%) for neural canal opening area, and 0.01±0.01 (2.60%±3.01%) for cup-to-disc ratio. FIGS. 8A-D illustrate macular and PP OCT multi-layer segmentation. FIG. 8A illustrates a SD-OCT macular volume 20 with 10-layer (11-surface) volumetric segmentation and FIG. 8B shows a 3D rendering of the macular volume, showing the NFL 502, the GCL 504, and the Combine layer 506 of the OS and RPE. FIGS. 8C&D illustrate a SD-OCT peripapillary volume 30 with segmentation, detecting the ONH 510. FIG. 8D illustrates a 3D rendering of the peripapillary volume 30.

In an aspect, the present systems and methods can be used to determine local relationships between the thickness of the GCL 504 in the macular area (i.e., the macular grid 300) and the thickness of the NFL 502 in the corresponding peripapillary region based on the known anatomy of the RGC soma/axons and nerve fiber bundle (NFB) trajectories. The relationships are also demonstrated by the trajectories derived from structural data. A spatial pattern consistent with NFB trajectories can be derived from the structure-structure correlations, as shown in FIGS. 9A-D. The NFB map can rely on the presence of relatively early, focal damage (thinning) in a particular PP-NFL region 410 with correspondence in a particular area of thinning in the GCL from in the macular region 310. The ability to form this NFB map strongly suggests that these correspondences exist and can be used for glaucoma diagnosis, staging, and treatment.

FIGS. 9A-D illustrate emergent two-dimensional patterns of nerve fiber bundle distribution in glaucoma. FIG. 9A illustrates a correlation grid of the macular regions 310 and ONH grid regions 410 corresponding to a grid pattern used in 10-2 VF testing. FIG. 9B illustrates a color-coded map resulting from correlating regions 310 within the macular grid 300 and wedge-based regions 410 of the ONH grid based upon the correlation of retinal ganglion cell layer thicknesses and peripapillary retinal nerve fiber layer thicknesses respectively. The regions 310, 410 share the same colors having the largest correlation between GCL and NFL thickness respectively. The map closely resembles the 2-D pattern of the NFB in the macula and the temporal peripapillary retina shown in FIGS. 6A-D. FIG. 9C illustrates nerve fiber bundles 700 of the eye as well known in the art (as described by Fitzgibbon and Taylor). FIG. 9D illustrates an enlarged portion 705 of nerve fiber bundles 700 from FIG. 9C overlaid with the color structure-structure correlation map of FIG. 9C. Note that NFB trajectories follow the single-color macular grid regions 310 that are derived from structural OCT indices in clear correspondence with peripapillary ONH grid wedge regions 410, sharing the same color.

In an aspect, the present systems and methods can be used to predict visual function (i.e., standard 24-2 Humphrey perimetry) using automated analysis of glaucoma damage based on SD-OCT. As an example, structural analysis by SD-OCT is completely objective and more reproducible and patient friendly than perimetry. However, the dynamic range of the commercially available SD-OCT derived parameters, including global thickness of the NFL and GCL, do not correspond sufficiently well with visual thresholds.

Figure 10:
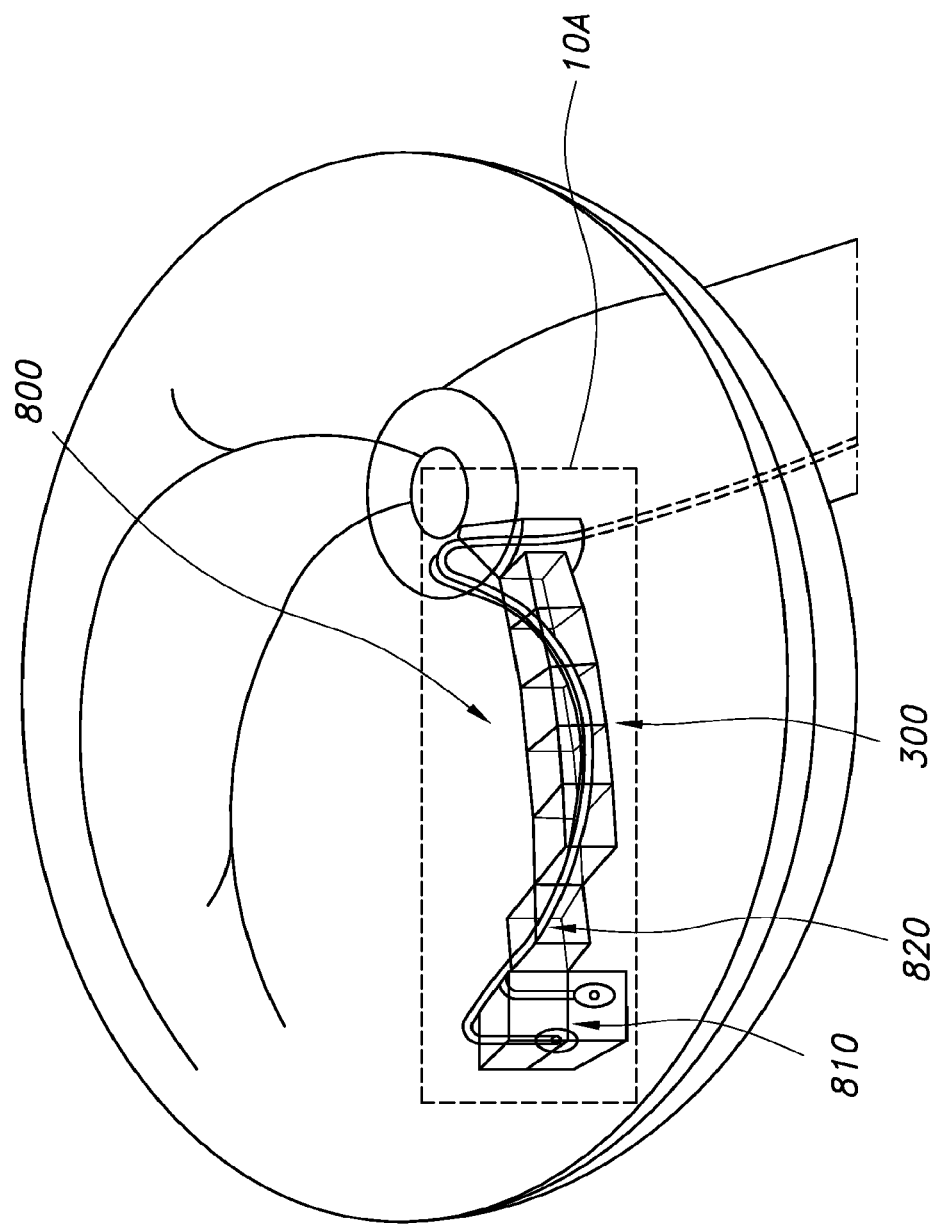

As an example, FIGS. 10 and 10A illustrates a RGC-AC 800 comprising a set of ganglion cells 810 and their axons 820, shown in gray, located in a single 24-2 based retinal region of the macular grid 300. RGC-AC indices, such as regional thickness or rim area, are calculated for its ganglion cell layer region 504, the RGC-AC origin 830 (block outlined in bright green), its patient-specific nerve fiber layer trajectory regions 840 (adjoining blocks in black) and its terminal optic nerve head wedge shaped region 850 (in dark green).

Figure 11A:
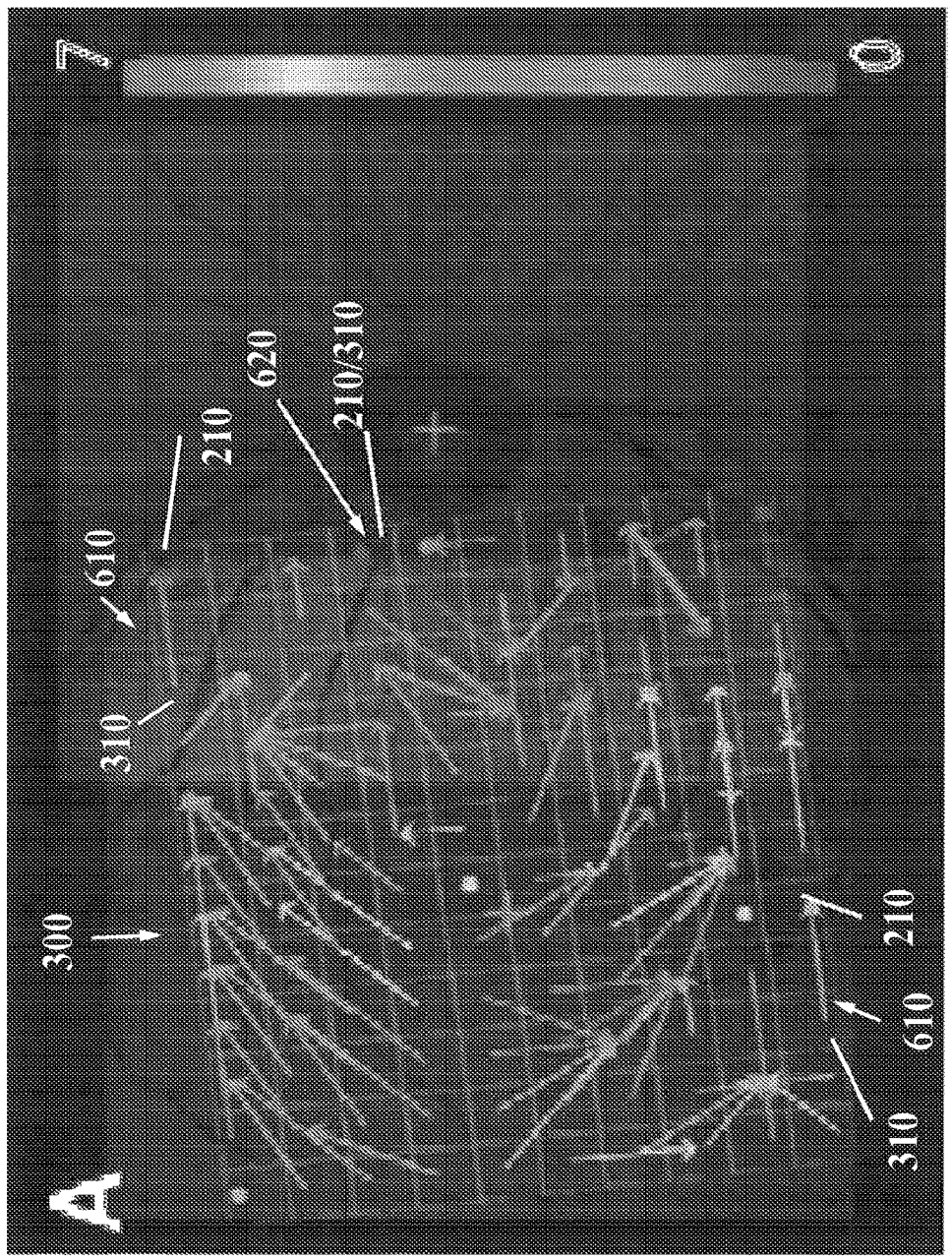
FIGS. 11A-B illustrates an emergent connectivity RGC-AC maps overlaid on a registered projection image from a single subject.
Figure 11B:
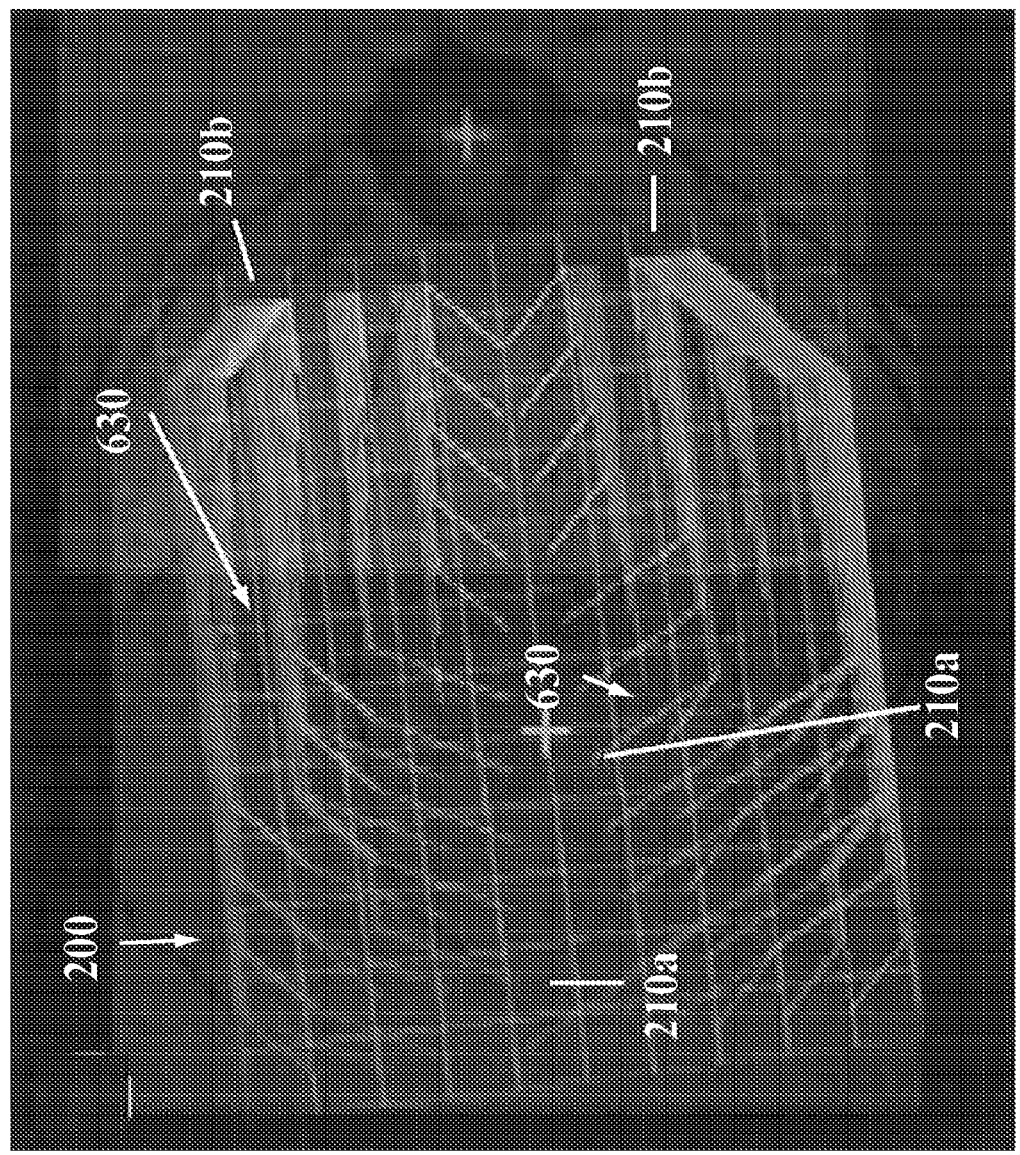

In another aspect, FIGS. 11A-B illustrate emergent connectivity RGC-AC maps 900 similar to those shown in FIGS. 6 (overlaid on a registered projection image 950 from a single subject). FIG. 11A illustrates connectivity from a macular GCL regions 310 to close initial NFB regions 210. An arrow 610 that starts in an macular grid region 310 ends at one of 5×5 neighboring NFB grid regions 210, which exhibits the maximum correlation (R2 value indicated by arrow color). A dot 620 located in a specific grid square 210/310 denotes that the highest correlation was between the macular and NFB region indices in the same location. FIG. 11B illustrates connections of individual NFB regions 210*a* (RGC-AC segments in the NFL 502), from initial (anywhere in NFB grid 200) to most nasal NFB grid regions 210*b*. The line 630 starting from each NFB grid region 210 and ending at one of the most nasal NFB regions 210 is the minimum cost path, depicting the highest overall correlation among all possible NFL 502 thickness indices of the NFB segment 210. The color of the line/path 630 represents the starting position of the path in the region 210*a* of the NFB grid 200, which is carried through until the line arrives at the most nasal NFB region 210*b*. In an aspect, the top and bottom lines 630 follow the top/bottom boundaries of the NFB grid 200 when information was not available outside the registered SD-OCT scans.

In an aspect, the retinal ganglion cell body-axonal complex (RGC-AC) is a new and innovative concept, defined as a set of neighboring ganglion cells in the retinal ganglion cell layer (GCL) 504 together with their axons forming an NFB in the retinal nerve fiber layer (NFL) 502 until their exit from the eye in the ONH 510, as shown in FIG. 10.

The RGC-AC can have multiple segments: A cell body segment localized in the retinal GCL 504; multiple NFB segments localized in the retinal NFL 502 between the cell body and ONH in a patient-specific trajectory; and an ONH segment located in the neural rim 512 of the ONH. The distribution and trajectory of the RGC-AC have been studied by visually examining histology of stained retina and of its NFB part by examining patterns of visual field defects.

As an example, damage that causes glaucoma is distributed over the entire RGC-AC, that retinal ganglion cell body damage is accompanied by corresponding nerve fiber and optic nerve head axonal loss, and that RGC-AC damage can be quantified and mapped using the methods and system of automated analysis of images from commercially available SD-OCT as discussed above. The systems and methods can derive RGC-AC indices, trajectory, and distribution maps entirely from structure to structure thickness correlations along the RGC-AC, assuming only the basic NFB anatomy. The emergent structural maps, as shown in FIGS. 6(A&D), 7(A&B), and 11(A&B), display the course of the RGC-ACs and are suggestive of the same distribution of nerve fiber bundles established from retinal histology and from patterns of visual field defects (NFB only). Accordingly, in glaucoma: a) the magnitude of the correlation of regional damage within a single RGC-AC is a measure of the damage of the entire RGC-AC and therefore it represents the ultimate correlate of visual function within the originating RGC-AC region; and b) the number of RGC-ACs with high damage correlation is a measure of glaucoma damage stage: The more RGC-ACs with high correlation, the larger the number of RGC-ACs that are damaged.

In as aspect, RGC-AC damage appears to be an all or nothing event—when the RGC-AC is damaged, it is damaged along the entire path of the RGC-AC. As glaucoma progresses, additional neighboring RGC-ACs are progressively "dropped out" or damaged. It is thus the lateral extent or drop-out of additional RGC-AC that corresponds to glaucoma progression and corresponds to visual field thresholds. This additional RGC-AC dropout can be measured not only by thinning of certain retinal layers, but also by the lateral extent of the "thinned" RGC-AC in known NFB trajectories. In other words, the "smart" 3-D structural assessment of RGC-AC in anatomically defined NFB trajectories yields excellent S-F correlation.

Structure-Function Correlation in Advanced Glaucoma

FIGS. 12A-D illustrate the structure-function correlation in a patient with advanced glaucoma. FIG. 12A displays an NFB Layer thickness map, as well as a zoomed-in view of the ONH rim and cup segmentation of a subject with advanced glaucoma. The image was segmented after registration of 9-field OCT (discussed below), with the ONH segmentation overlaid for clarity. On the zoomed ONH, the segmented cup is segmented and displayed in red, the rim is green, with a white arrow pointing to a locally thin rim from the cupping. The yellow arrow indicates the fovea, and red arrows delineate severely thinned NFL segments of an RGC-AC bundle.

FIG. 12B illustrates the visual function assessment obtained for the same subject using a 24-2 HVF of same eye/same patient, with the red arrow pointing to an area deep functional loss. Regional sensitivities of all 24-2 regions are shown in FIG. 12C, converted to grayscale and flipped to correspond to retinal orientation (removing the inversion caused by optics of the eye). The red arrow points to deep scotoma. Lastly, FIG. 12D shows an overlay of structure on NFL thickness, where the deep scotoma corresponds to NFL loss along the RGC-AC bundle. All the metrics shown in these figures as well as GCL thickness (not shown) are combined to improve prediction of local structure from function in the whole spectrum of glaucoma including advanced disease.

Pilot Study Example and Results

As shown in FIGS. 13A-E, using the RGC-AC concept progressively leads to improved structure-function correlation even in advanced glaucoma. In a small pilot study, the NFL, ONH and GCL segmentations were used to obtain the following structure to function correlations from 6 patients with advanced glaucoma who had 9-field OCT and 24-2 visual field testing. Scatterplots are shown for one of 54 locations of 24-2 HVF grid—specifically for location 20 linearized sensitivity, which is far temporal. FIG. 13A shows that at location 20, GCL thickness shows poor correlation with location 20 linearized function ($R^2=0.09$). As illustrated in FIG. 13B, NFL thickness correlation with location 20 linearized function is also poor ($R^2=0.09$). FIG. 13C shows that a relationships of ONH wedge 135-180 degree rim area to visual function shows better correlation ($R^2=0.57$). FIG. 13D adds the ONH rim area, GCL and NFL location 20 thickness to NFL thickness for the entire Garway Heath region #2 to which location 20 belongs. The correlation with function improved in our pilot ($R^2=0.72$). Last, FIG. 13E shows using patient-specific RGC-AC trajectories and aggregating the same values improves the correlation with function even more ($R^2=0.97$). This is true even for the peripheral location 20, where the retina is thin and visual function variability is high.

9-Field Registered Composite Example

In an aspect, a 9-field registered composite OCT is used to model a 24-2 visual field. While other composite OCTs can be used (e.g., ones that generate a 10-2 VF), the 9-field registered composite OCT is preferable because it corresponds to the Humphrey 24-2 VF test, which is the clinical standard for glaucoma management. In another aspect, the automated determination of GCL 502, NFL 504, and ONH structural and textural parameters over the entire 9-field OCT montage image, because the extent of standard isotropic SD-OCT (i.e., with sufficient density of A-scans for quantitative image analysis) is limited to approximately 6×6 mm2 (20°). Accordingly, SD-OCT offers fast, objective data acquisition and is much easier for the glaucoma patient than active participation of perimetric testing. The novel structural OCT indices that are highly correlated with visual function will reduce the need for frequent perimetry, which will lead to increased patient happiness and reduced time and cost for glaucoma care.

In an aspect, utilizing local and regional image information about the 3D morphology and 3D tissue characteristics of retinal layers in a 9-field composite OCT scan, at a resolution and retinal coverage not previously available, leads to the collection of multi-tile OCT scans that are registered with each other, with retinal fundus photographs, and with 24-2 Humphrey visual field test data.

Figure 14:
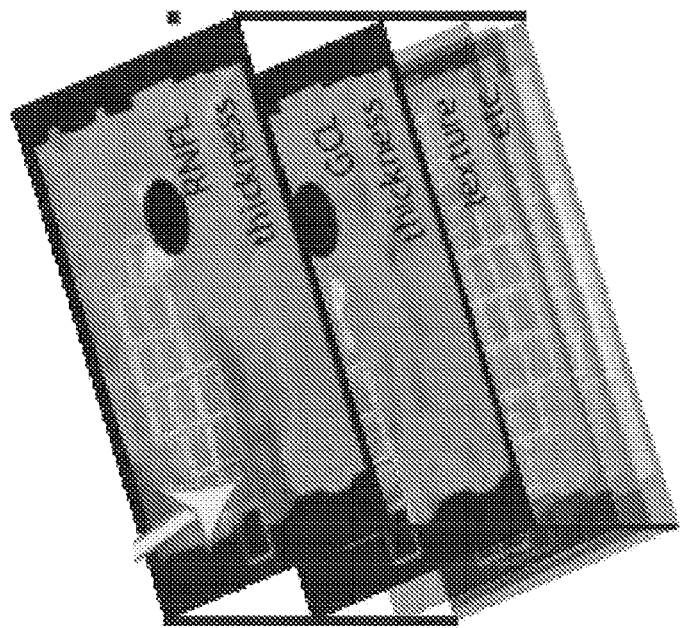
FIG. 14 illustrates an example of registering multiple fields according to an aspect.
Figure 15:
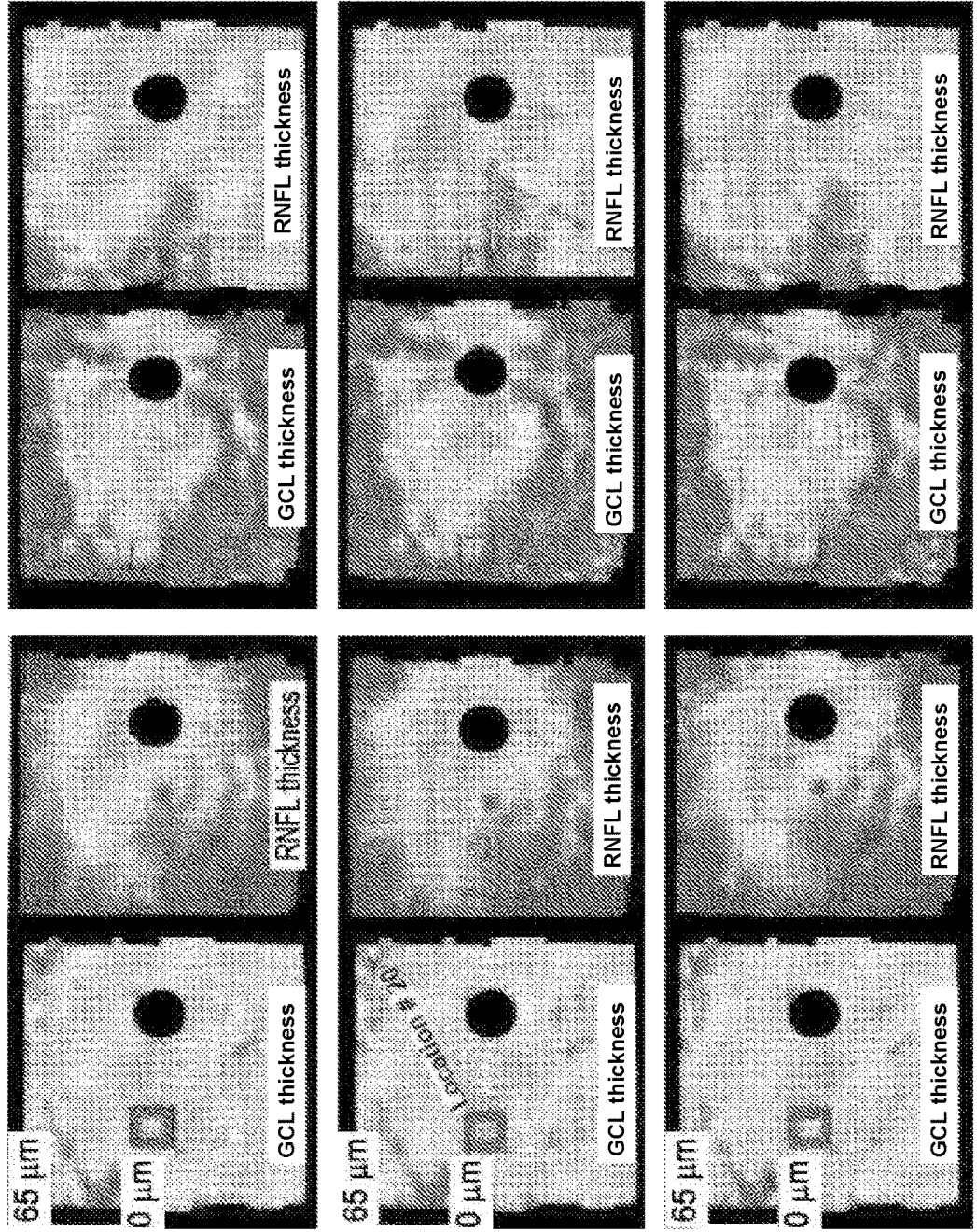
FIG. 15 illustrates an example of multiple registrations according to an aspect.

In an example of such an aspect, 3D spectral OCT datasets for a total of 40 eyes from 40 normal subjects and 100 eyes of 100 glaucoma patients is collected. 20 patients are imaged twice in order to study reproducibility. In all cases, OCT images from one eye per subject were included in the dataset. A total of 9 OCT scans are acquired for each study subject with eye tracking, as shown in FIG. 14. Scanning was performed using the latest generation, commercially available, Spectralis OCT scanner (Heidelberg Engineering, Carlsbad, Calif.) using gazetracking mode. Alternatively, other OCT scanners can be used. The approach used was the standard 9-field protocol available in the Heidelberg control software. The protocol covers approximately 50 degree area, slightly beyond that tested in 24-2 perimetry. A scan quality algorithm equivalent to the Zeiss Cirrus signal strength metric was developed, using only scans with signal strength equivalent to level 5 or better. During scanning, the patient followed the fixation blue light as adjusted automatically by the scanner software in a 9-field pattern. the entire protocol takes approximately 7 minutes per eye.

Figure 16A:
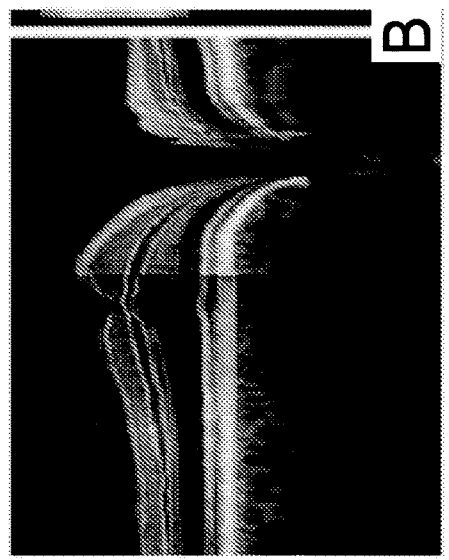
FIGS. 16A-D illustrate 9-Field Spectalis OCT registrations according to an aspect.
Figure 16B:
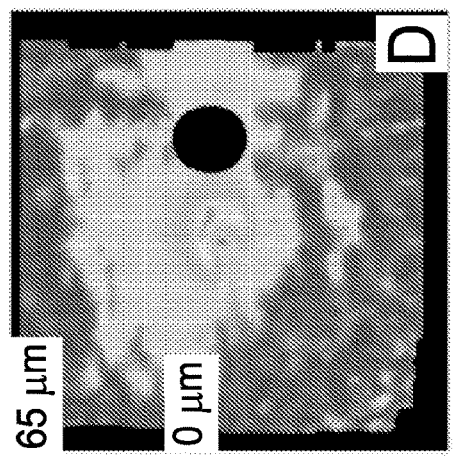
Figure 16C:
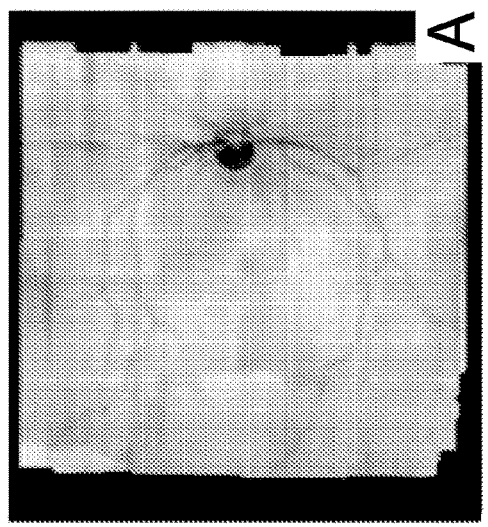
Figure 16D:
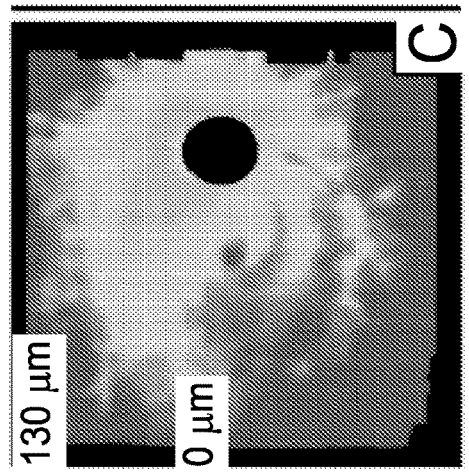

Each of the obtained 9 volume scans per eye is of size 768×61×496 voxels (volumetric pixels) 9.53×8.07×1.92 mm3 (covering ±15.88 degrees in x direction, ±13.45 degrees in y direction in the en-face), with each anisotropic voxel approximately 12.41×132.22×3.87 μm3 in size. Other field sizes are possible. The volumes pairwise overlap by about 25% allowing their registration, other overlaps are possible. Even in advanced glaucoma with limited acuity, the acquisition protocol was well tolerated and in all cases yielded well-positioned OCT scans that were suitable for 3D multi-tile registration. We achieved 3D mosaicking of these 9-field OCT scans (FIG. 16A). and FIG. 16B demonstrate feasibility of 11-surface segmentation of 9-field registered OCT composites and feasibility of computing thickness and texture maps of each of the 10 retinal layers (FIG. 16C-D).

In an aspect, imaging can be performed according to the following protocol.
 1. Perimetry will be performed by experienced perimetrists using (i) Humphrey 24-2 SITA visual field protocol (See FIG. 14). VF data can be routinely exported digitally for functional analyses.
 2. 9-field 3D OCT imaging can be performed using Spectralis SD-OCT with eye tracking as described above. As an example, OCT imaging can be performed by an experienced technologist.
 3. Stereo fundus photographs (at least 30 degrees field of view) of the macula and optic disc regions can be taken using an Ophthalmic Imaging Systems digital photography system. Pupils can be dilated if necessary.
4. OCT volumes can be exported and stored with other subject data. Comprehensive OCT, fundus, and VF data can be stored and de-identified in a dedicated research database together with additional data described below.

In an aspect, the following information can be obtained from the subject or patient records: age; gender; race; ethnicity; clinical ophthalmological diagnoses; laterality (OD or OS); visual acuity; intraocular pressure. Such information can be used in the analysis of any OCT results.

7-Field Registered Composite Example

In an aspect, a 7-field registered composite OCT is used to model a 24-2 visual field. While other composite OCTs can be used (e.g., ones that generate a 10-2 VF), the 7-field registered composite CT is one of preferred protocols because it corresponds to the Humphrey 24-2 VF test, which is the clinical standard for glaucoma management. In another aspect, the automated determination of GCL 502, NFL 504, and ONH structural and textural parameters over the entire 7-field OCT montage image, because the extent of standard isotropic SD-OCT (i.e., with sufficient density of A-scans for quantitative image analysis) is limited to approximately 6×6 mm2 (20°). Accordingly, SD-OCT offers fast, objective data acquisition and is much easier for the glaucoma patient than active participation of perimetric testing. The novel structural OCT indices that are highly correlated with visual function will reduce the need for frequent perimetry, which will lead to increased patient happiness and reduced time and cost for glaucoma care.

In an aspect, utilizing local and regional image information about the 3D morphology and 3D tissue characteristics of retinal layers in a 7-field composite OCT scan, at a resolution and retinal coverage not previously available, leads to the collection of multi-tile OCT scans that are registered with each other, with retinal fundus photographs, and with 24-2 Humphrey visual field test data.

In an aspect, 3D spectral OCT datasets were collected for a total of 40 eyes from 40 normal subjects and 100 eyes of 100 glaucoma patients. In all cases, OCT images from one eye per subject were introduced to the dataset. A total of 7 OCT scans, one for each field, were acquired for each study subject. Scanning was performed by using the Cirrus OCT scanner (Carl Zeiss Meditec, Inc., Dublin, Calif., USA). Other scanners can be employed. The approach followed was a modified 7-field stereo photo protocol as developed for the Early Treatment in Diabetic Retinopathy Study, familiar to ophthalmic photographers. The protocol covered approximately the entire 48 degree area tested in 24-2 perimetry. During scanning, the patient followed a fixation cross as adjusted by the operator in a 7-field pattern and the entire protocol takes approximately 10 minutes. Each of the obtained 7 volume scans per eye was of size 200×200×1024 voxels (volumetric pixels) 6×6×2 mm3 (covering ±20.94 degrees in the enface, or x and y directions), with each anisotropic voxel approximately 30×30×2 μm in size. The volumes pairwise overlap by about 20% allowing their registration. Other field sizes and other overlap ratios can be employed. To demonstrate feasibility of both the acquisition and registration, a plurality (e.g., three) 7-field OCT scans can be acquired from normal subjects. The acquisition protocol was well tolerated and in all cases yielded well-positioned OCT scans that were suitable for 3D multi-tile registration. Preliminary 3D mosaicking of 7-field OCT scans in pilot subjects demonstrated feasibility of 11-surface segmentation of 7-field registered OCT composites. The results also demonstrated the feasibility of computing thickness and texture maps of each of the 10 retinal layers. The image data acquisition can follow the same protocol as discussed above.

Structural Indices

In an aspect, utilizing local and regional image information about the 3D morphology and 3D tissue characteristics of retinal layers in a 7-field or 9-field composite OCT scan, at a resolution and retinal coverage not previously available, leads to the collection of multi-tile OCT scans that are registered with each other, with retinal fundus photographs, and with 24-2 Humphrey visual field test data.

In an aspect, structural and textural indices can be computed for each of the segmented retinal layers (e.g., NFL 502, GCL 504) as global and regional indices. Structural indices are separately calculated for each layer and any desired region and include layer thickness, thickness variability, difference between regional and global thicknesses, difference between regional and normative thicknesses (determined in the set of normal subjects), and 21 three-dimensional statistical texture features. As an example, the regional indices can be determined in 54 regions corresponding to the 54 functional fields of the Humphrey 24-2 visual field test as well as in equally sized regions outside of the 24-2 VF for which OCT coverage is available. As a routine step for increasing regional accuracy, layer thickness indices are adjusted based on vessel positioning (since vessel presence typically causes locally increased thickness of the innermost layers). At the ONH, the following indices are routinely determined by us in an automated fashion: projected area of the neural-canal-opening, area of the optic disc, linear cup-to-disc ratio, rim area/volume, and cup area/volume.

In an aspect, to register the multi-field retinal OCT images in 3D, a two-step, 3D, registration approach (i.e., creating a single volume from the fields collected) can be extended. First, the registration can be performed in the XY-plane by registering all OCT projection images in the multi-field set in a pairwise manner using an Iterative Closest Point (ICP) based algorithm, as discussed in M. Niemeijer, K. Lee, M. K. Garvin, M. D. Abr'amoff, and M. Sonka's *Registration of 3D spectral OCT volumes combining ICP with a graph-based approach*. In Proceedings of SPIE Medical Imaging 2012: Image Processing, volume 8314, page 831445, the entirety of which is incorporated by reference. An advanced cost function can be used for the ICP algorithm that not only takes into account the distance of the vessel centerlines to each other but also the local vessel orientation and the local vessel diameter. After all projection images are pairwise registered, a second-step global ICP optimization can be employed for the depth direction. A graph based approach can be used to perform registration in the depth direction. Each individual A-scan that belongs in the 2D-registered OCT scans to any of the sub-areas of OCT field overlap can be translated along the depth axis and the mean squared error (MSE) calculated. By minimizing the overall volumetric MSE, the optimal translation surface is determined passing through the volume using a graph-search based algorithm. For those A-scans that are not in an overlapping area, interpolation can provide proper local translations along the depth axis. FIG. 16A illustrates a pilot implementation of the described technique and demonstrates feasibility of the proposed approach.

In an aspect, once the individual OCT fields are registered to form a single data volume for a subject, the graph-based multi-layer segmentation can be performed. The graph-based multi-layer segmentation can be extended from the single-OCT volume to work in the multi-field composite OCT image data after the OCT fields are registered to a single data volume. The locations of the fovea and the ONH can be derived in a standard fashion and can be used as a priori information for the 10-layer/11 surface segmentation in the entire composite image. For the purposes of the multi-layer segmentation, the ONH region can be defined in the same way as currently routinely defined on ONH scan fields, as the area specified by the neural canal opening (NCO). In other words, the multi-layer segmentation can produce continuous definitions of 11 surfaces (10 layers) for the entire composite OCT image with the exception of the ONH region in which no layers can be determined since they are not present. It is possible that in some areas far away from the fovea and ONH, retinal layers can not be reliably segmentable. Using an established approach for detection of non-reliable layer segmentations, these areas can be identified and excluded from further analysis.

The disclosed segmentation approach can be an extension of the current optimal graph-based multi-layer segmentation. The segmentation can take advantage of all to-date developed methodological advancements, including mutual multi-layer context, shape priors, combined edge-based and regional cost functions, multi-scale fast processing, and image-derived knowledge of the foveal and ONH locations. FIG. 16B gives an example of the expected multi-layer segmentation output on the composite OCT images.

The composite image segmentation performance can be assessed in a subset of the data (20 glaucoma patients) by determining surface positioning segmentation errors for all 11 detected surfaces in comparison with an expert-defined independent standard. The validation can be performed in the same way as previous generations of multi-layer segmentation methods have been validated, where the obtained segmentation errors can be compared with the errors achieved by the so-far best-performing segmentation method. In an aspect, some tools provide multi-surface segmentation accuracy of 5.7±1.4 μm which is comparable to the typical inter-observer variability of manual surface tracing of 5.7±2.0 μm.

In an aspect, a large number of quantitative indices of retinal layer thickness and texture can be determined from the multi-field composite image data. The same local and regional quantitative indices can be calculated for the multi-field composite image data as were calculated for the individual macular OCT scans. Once segmented as described herein, the calculation of the indices can be extended to cover the entire area of the composite scan.

Figure 17:
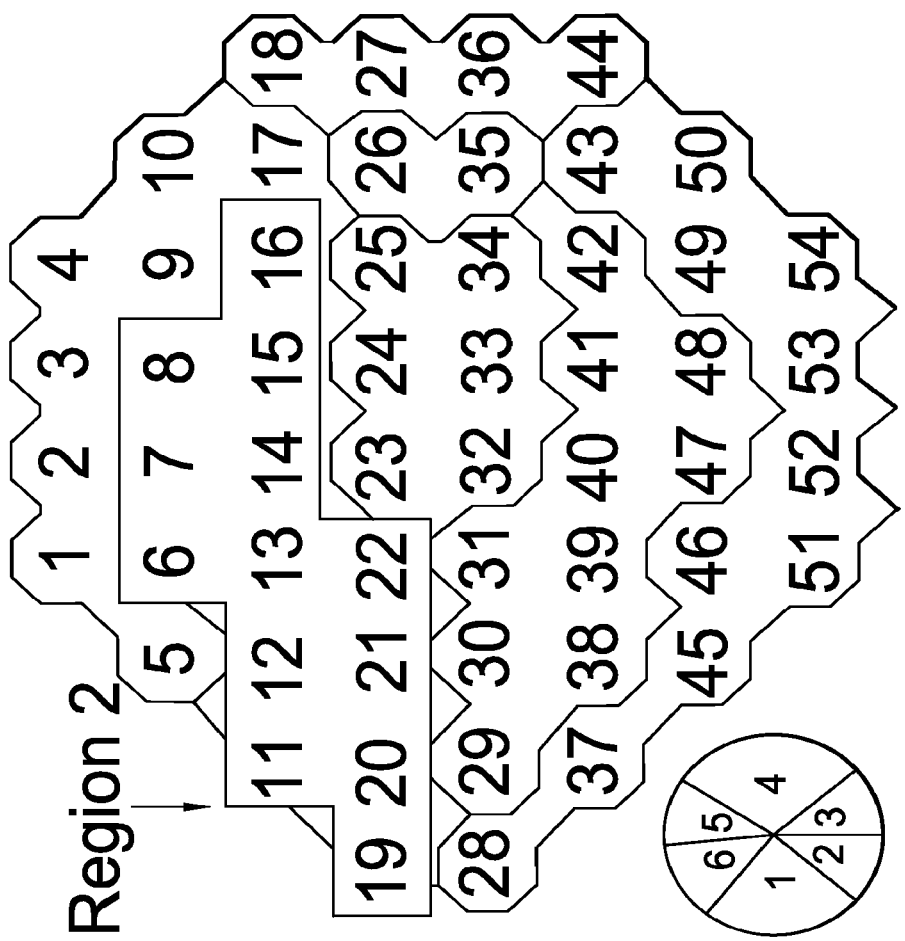
FIG. 17 illustrates a 24-2 HVF grid according to an aspect.

As described herein, the 24-2 visual field sensitivity map can be assessed in 54 locations corresponding to the 54 regions from the 9-field composite OCT, as shown in FIG. 17. The locations of the Humphrey 24-2 VF sensitivity assessment values can be carefully registered with the 9-field OCT data and the relationships between the VF sensitivity loss values and intraretinal layer properties can be assessed in these 54 locations.

To identify associations between the visual field sensitivity and the quantitative indices derived from intraretinal layer thickness and texture properties in the composite 9-field OCT data, statistical and classification methods can be employed, including, but not limited to, those methods discussed above. The initial descriptive analysis can investigate the associations between the 54 VF sensitivity measures and each of the regional indices of OCT morphology and texture from the image analysis of each individual eye, i.e., 40 normal and 100 glaucoma eyes. Both graphical and statistical modeling approaches can be used. Having two study groups (normal, glaucoma), strong associations can exist with at least some of the morphology and tissue texture indices for the glaucoma group. Patterns of association can be characterized and the percentage of times a significant association is identified can be tabulated for each morphology and tissue texture index by study group. Similar approaches can be used to analyze the combined data for each group of eyes, i.e., all normal and all glaucoma eyes. Both linear and non-linear models can be investigated to identify the best functional relationships (based on previous reports) including (anti)logarithmic transformations, and the coefficient of determination (R2) can be estimated. The associations among the OCT morphology and texture indices can also be investigated. For example, Raza et al. argued for utilizing an offset between retinal locations in which structural indices should be measured and VF locations when using 10-2 VF tests Multivariable general linear models can then be developed for each study group to identify the combination of all the regional morphology and tissue texture indices that provide the best prediction of VF sensitivity. If a non-linear relationship is identified from the initial descriptive analysis, the results from that analysis can be utilized in fitting the multivariable models. The non-independence of the data (n=54 observations for each eye) can be accommodated by including a random 'eye' effect in the model. In an aspect, the random eye effect can be used to remove associations between a left and right eye from the data. Both forward and backward stepwise approaches can be used and influence diagnostics can be examined to identify data points with an undue influence on the fitted model. Poorly predicted VF sensitivity values can also be identified (outside 3 dB, 5 dB, 7 dB of the observed VF sensitivity measure) for further evaluation of the predictive model. The final models for the two study groups can be compared with regard to the indices selected.

Sample Size and Power Analysis

A study by Vass et al. reported correlation coefficients between VF sensitivities and retinal layer volumes that ranged from 0.20 to 0. Recently, Leite et al. and Lopez-Pena et al. reported very similar values. For the individual analysis of each eye (n=54 data points), 80% power (90% power) can be used to detect a correlation coefficient of 0.38 (0.43) using a two-sided test with a significance level of 0.05. For the multivariable modeling, if a regional morphology or tissue texture index is added to a model that already includes four of the indices that explain 10 to 20% of the variability in VF sensitivity, with a sample of 2,160 (5,400) observations (40 normal subjects and 100 glaucoma patients), greater than 90% power can be used to detect as significant an additional 0.44% (0.17%) of the variance explained by the index that is added.

The ability to use the multiple indices of regional intraretinal layer structure and texture for objective determination of the visual field sensitivity in the corresponding location can be evaluated using classifiers, including, but not limited to, k-nearest neighbor or support vector machine classifiers. These types of classifiers can be used due to their ability to associate multi-feature inputs with continuous-valued outputs. Here, the indices of regional layer thickness, layer texture, and volumetric indices can serve as inputs in the form of feature vectors, possibly in added context from neighboring macular column descriptors (i.e., properties of the regions). Feature selection can be performed using a sequential forward-floating search. In another aspect, other searches and methods known in the art can be used. Once most discriminative features are selected, the reduced set of features can be used in developing the final classifier.

Figure 18:
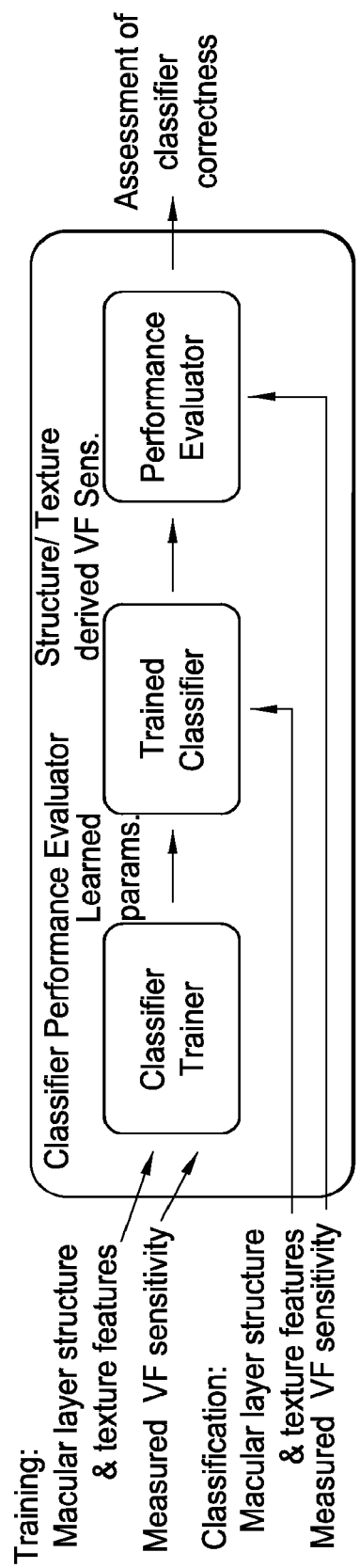
FIG. 18 is a flow chart of a method of developing classifiers according to an aspect.

The measured visual field sensitivity values can serve for classifier training as well as testing. In an aspect, given training and testing sets, and a classification approach, the general scheme for measuring the classifier's performance is shown in FIG. 18. As shown, data related to structures (thickness, texture features), as well as VF sensitivity measurements are captured. Once the parameters for the classifiers are learned, they are classified. Once trained using a training set, the classifier is run on the test set and the performance is measured by comparison with the known outcome. A leave-x %-out fashion training and testing approach can be used to evaluate performance. For purposes of evaluating the classifier performance, 20% of the data from each subject group (normal, glaucoma) can be removed. The results can be compiled in a "confusion matrix" reporting the classification correctness. Because the visual field sensitivity is a continuous variable, the confusion matrices can be constructed for several values of VF prediction accuracy, ±3 dB, ±5 dB, ±7 dB, etc.

In the identification of structural and textural indices that best predict VF sensitivity, it was found that the indices most closely associated with the ganglion cell layer and/or peripapillary NFL can be most important. This is, in part, due to the "local" nature of such indices in combination with the importance of the ganglion cells in glaucoma. However, in other aspects, the "accumulating" nature of the macular (not peripapillary) retinal nerve fiber bundles and the corresponding optic-nerve-head indices can be taken into consideration.

In an aspect, visual function can be assessed or predicted from structural parameters. As an example, this is done by directly pairing a set of regional structural indices (e.g., thickness, area, etc.) with each regional 24-2 visual field sensitivity value. Note that only regional information is used, and no consideration is given to the rest of the RGC-AC trajectory. In other aspects, other information can be used to add additional properties along the RGC-AC trajectory. Damage to the RGC-AC typically occurs along its entire trajectory. Therefore, including such information can be expected to improve the predictive model, and the potential improvement from more sophisticated approaches using indices from the entire RGC-AC trajectory can be tested here.

In an aspect, the set of SD-OCT structural indices can be enhanced for predicting visual function using the RGC-AC concept by: 1) considering structural indices of wedge shaped regions of the ONH, such as rim area, and 2) including regional structural indices along the RGC-AC trajectory through the NFL. Because NFB trajectories are patient specific, determining indices for the grid regions through which the RGC-AC passes requires knowledge of these trajectories. For this aim, a statistical atlas based approach can be employed to determine the average NFB trajectories for each 24-2 region.

Figure 19A:
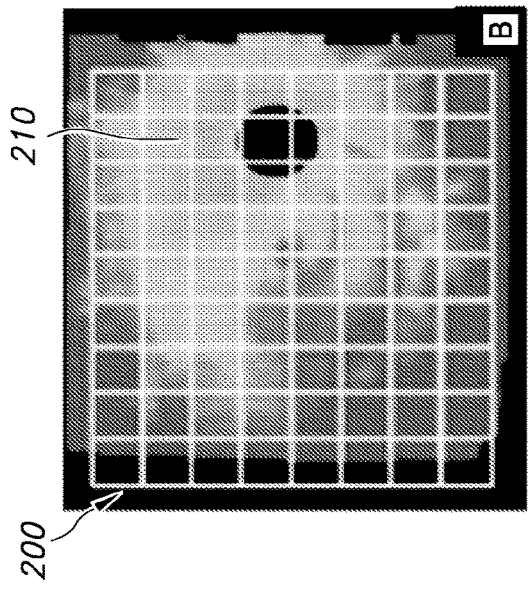
FIGS. 19A-D illustrate a representation of regional grid and ONH wedge regions according to an aspect.
Figure 19C:
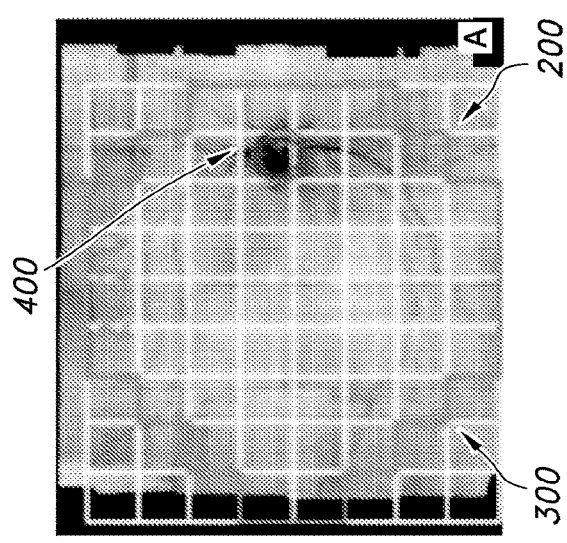
Figure 19B:
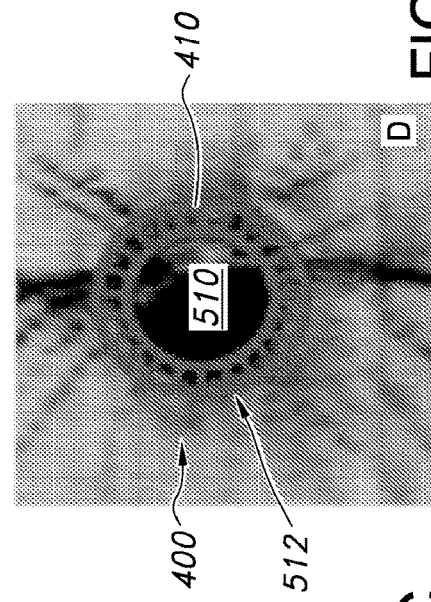
Figure 19D:
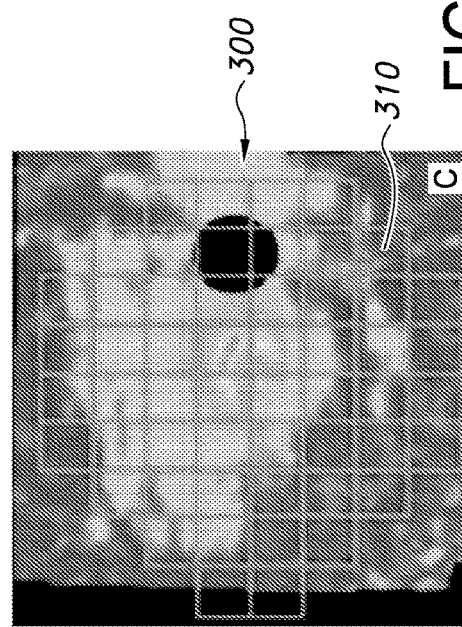

The NFB grid 200, the Macular grid 300, and the ONH grid 400, including their respective regions 210, 310, and 410, are illustrated in FIGS. 19A-D. The grids are 10-2 based grids, extended to coincide with 24-2 VF geometry. The NFB grid 200 consists of 92 square regions 210, the combined area of the regions 210 being the same as the area covered by a single 24-2 testing location. The NFB grid 200 is shown as the white overlay on FIG. 19A-B. Note that three-dimensionally, the NFB grid 200 is positioned within the NFL layer 502 (meaning that grid properties are associated with NFL parameters). The RGC grid, or Macular grid, 300 locationally coincides with the NFB grid 200 and is three-dimensionally positioned within the GCL layer 504. The RGC grid 300 consists of 54 regions 310 corresponding in "en-face" size and location with the 24-2 testing locations (FIG. 19C). Each square region 310 of the RGC grid 300 also represents the ganglion-cell origin of each RGC-AC trajectory for which structural indices can be computed. The ONH grid 400, centered on the NCO center 510, is composed of 24 wedge-like volumetric regions 410 positioned on the ONH rim 512, each covering a 15° rim subregion (FIG. 19D). FIG. 10 shows the 3-D character of the RGC-AC trajectory.

The incorporation of regional indices for 24-2 regions 210, 310, 410 [Correct?] along each expected RGC-AC is a novel contribution. To define the atlas of RGC-AC trajectories, three approaches can be used Use of existing structure-structure correlation approach extended to the 9-field OCT mosaic. RGC-AC trajectories can be solely defined using structure-structure correlations of regional GCL and peripapillary NFL thicknesses to obtain expected RGC-AC trajectory groupings.

Use of the Garway-Heath model coupled with trajectory estimation, which is a popular grouping scheme.

Use of RGC-AC trajectory mapping approach as explained in to determine trajectories using damage correlations across subjects. Additional constraints such as non-overlapping properties can be added to guarantee RGC-AC trajectory feasibility and increase robustness.

In an aspect, extending the preliminary graph-search-based approach to simultaneously deal with multiple trajectories, one is able to determine RGC-AC trajectories for the entire group-based composite OCT image in a single optimization process. In this approach, mutual context of individual "population-based" trajectories can be considered, thus forming the RGC-AC trajectory atlas, as described in more detail below. The developed method can be a non-trivial extension from a single-path search to a simultaneous (or parallel) multiple-path search method. For determining the RGC-AC atlas, the developed method can consider multiple origins for the individual RGC-AC trajectories (all 54 VF locations) and a single common end-point (the center of the ONH 510) (step 2000). Each region 210 of the NFB grid 200 represents a "node" in the graph. The method can yield an atlas set of trajectories by maximizing the overall population-based structural-functional correlation between the VF function at the RGC-AC origin and the structure/texture parameters for all RGC-AC trajectories simultaneously and considering all datasets from the group of glaucoma patients. A number of contextual constraints can be incorporated in the atlas-building process, for example that the individual trajectories cannot cross, no loops can be formed, minimum requirements for grid-building block distances can be considered, etc. Otherwise, no assumptions can be made about the location, shape, or length of the RGC-AC trajectories. To maintain full separation of datasets used for building the atlas and analyzing patient data, a "leave x % out" approach can be used.

When identifying the three-dimensional course of the RGC-AC trajectories in the 3-D OCT composite image for a particular subject, the composite image data can be matched with one of the atlases identified using simple registration approaches. For example, the RGC-AC atlas can be mapped using only the locations of the fovea and the ONH. As a result of a RGC-AC mapping, each RGC-AC trajectory can be associated with an ordered set of NFB grid regions 210 connecting the ganglion cell region 310 (RGC-AC region within the GCL layer 504) over multiple NFB regions 210 (within the NFL layer), to the ending region 410 of the ONH 510 (15° rim subregion). This atlas based RGC-AC trajectory set allows computation of the RGC-AC indices as described in the following sections. Compare this 3-D trajectory-associated set of indices with the simpler set of local indices (corresponding to only to the origin of the RGC-AC trajectories). Note however, that the derived trajectories are atlas-based and thus not fully patient-specific. Therefore, the trajectories and associated structural indices can be determined in "wider" regions along the atlas-defined RGC-AC trajectories to better deal with the expected cross-subject variability.

The atlas-based RGC-AC trajectory set allows definition of a new set of indices for each RGC-AC. In particular, the original set of indices associated with a particular 24-2 grid location can be extended with the inclusion of trajectory-specific indices such as the set of regional indices along the trajectory (possibly in a cumulative manner) and the differences/variability of regional indices along a trajectory (possibly determined as a cumulative difference). It is expected that NFL thickness differences/variability along the trajectory may emerge as an important glaucoma staging index. For example, if the gradual increase of NFL thickness is lower than normal, it indicates that the NFB contributions from the underlying ganglion cells to the above NFL thickness is low. In other words, the RGC-AC bundles are less dense or more sparse in that region, due to disease.

In an aspect, the standard set of global and regional ONH indices can be calculated. Regional ONH-metrics can be defined in ONH wedges considering the respective RGC-AC trajectories. In other words, the ONH rim subregion that on average best corresponds to the ending location of each particular RGC-AC can be used for calculation of the ONH indices. In an aspect, the combined incorporation of the RGC-AC based approach, including an atlas derived RGC-AC trajectory and NFL and ONH derived regional structural parameters can provide the necessary redundancy to enable stronger structure-function correlations and functional predictions.

As an example, damaged RGC-ACs are characterized by consistent GCL/NFL/rim area loss across the entire RGC-AC. Therefore, the more the indices are abnormal along the RGC-AC, the more confidence exists that the RGC-AC trajectory is correct. To illustrate this, in the limit, with a single RGC-AC completely obliterated by glaucoma, its GCL thickness, NFL thickness and rim area indices can all be zero (or very low), and maximally consistent. If glaucoma progression causes even more RGC-ACs to be obliterated, the RGC-AC bundle volume can be zero (or very low) everywhere. RGC-ACs are damaged in a sparse fashion at least in early glaucoma, so this is not likely to be a problem except in advanced cases. Even if the predictive S-F model is not improved by a patient-specific approach, the number of damaged RGC-ACs (as defined by the aggregate indices), can serve as a baseline structural damage assessment for future follow-up for the given patient and thus, provide more precise measure of change than the one computed from population-based (i.e., atlas-based) measures.

As a further example, once a potential RGC-AC is identified, the following aggregate RGC-AC indices can be calculated: (1) average of the correlation of all regional indices in the set, (2) median of each of the indices across the set, and (3) maximum of each of the indices across the set. The following three approaches to RGC-AC patient-specific trajectory detection can be performed:

A) RGC-AC trajectory derivation by warping: The atlas-based RGC-AC trajectories can be used as the starting point and can be made patient specific by adjusting the trajectory based on the individual locations of the vessel arcade, the fovea, the ONH, and ONH size. Our previously developed method for alignment of retinal images to OCT images can be used so that the ONH, fovea, and vessel arcades are aligned. The derived transformation matrix can be used to map the RGC-AC atlas to the underlying image data.

B) RGC-AC trajectory detection using replacement of likely damaged RGC-AC trajectories: The aggregate RGC-AC indices defined above represent damage indices. Therefore, the higher the aggregate RGC-AC index value, the higher the likelihood that the RGC-AC is damaged and the higher the confidence in correctness of the determined trajectory. In this approach, the simultaneous graph search can follow the atlas-based detection of RGC-AC trajectory sets in the single patient image data (not across a group of subjects) to derive a subset of highly probably "damaged" RGC-AC trajectories. These graph-based-identified (and thus patient-specific) sufficiently damaged RGC-AC trajectories can individually replace the atlas-based trajectories.

C) Direct RGC-AC trajectory detection: In this approach, the atlas is not used. Instead, likely damaged trajectories are first derived using the simultaneous graph search in single-subject data. The trajectories with high cost (too low correlation) are pruned from the set of resulting trajectories, resulting with a subset of most likely RGC-AC trajectories for each patient. In regions where there is little or no damage, the graph-search-defined trajectories can be sparse due to low confidence and thus high pruning rates. The subset of likely trajectories can be used as constraints for identifying the remaining trajectories, e.g., using interpolation approaches.

In an aspect, a 9-field OCT imaging that requires volumetric registration to form the composite OCT image can be used. The automated registration and/or segmentation can not be perfect under all circumstances and may even fail in some cases. For example, insufficient overlap between or motion artifacts of adjacent OCT fields may contribute to errors of OCT field registration thus affecting the computed parameters. We can have user-friendly tools in place to manually correct for any registration and/or multi-layer segmentation failures before computing properties of each of the intraretinal layers.

It may also be better to image the large retinal field using a single large-field OCT imaging device and such devices may become available in the future, though current pre-production versions offer a much lower A-scan density. Similarly, future adaptive optics OCT (AO-OCT) may provide higher image resolution and thus facilitate more accurate measurements of retinal structure. A current study imaging retinal nerve fiber bundles with AO-OCT is ongoing and may help identify RGC-AC trajectories in individual patients. If AO-OCT becomes widely available and can be derived directly from AO-OCT images, our work can receive yet another level of relevance for patient-specific treatment of glaucoma.

While the methods and systems have been described in connection with preferred embodiments and specific examples, it is not intended that the scope be limited to the particular embodiments set forth, as the embodiments herein are intended in all respects to be illustrative rather than restrictive. For example, while some of the exemplary systems and methods have used 7-field per eye 3D SD OCT images accompanied by 24-2 visual field test data, different numbers (e.g., 10-2) and combinations of OCT fields, different types of OCT imagers, and different testing types (e.g., Octopus visual perimetry) to test the visual field can be used to find the structural-functional relationships herein described.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification. Further, many of the methods, process, and steps discussed above can be carried out by a single computer application, including the detection software 106 of the computer of FIG. 1, or by multiple applications on a single or multiple modules.

Throughout this application, various publications are referenced. The disclosures of these publications in their entireties are hereby incorporated by reference into this application in order to more fully describe the state of the art to which the methods and systems pertain.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention. To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, those skilled in the art will appreciate that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A method comprising:
    receiving an image;
    determining a thickness of a cell layer within at least one of one or more regions of interest of the image;
    determining, for at least one of the one or more regions of interest, a set of correlations of the cell layer thickness to each of a plurality of nerve regions; and
    selecting from the plurality of nerve regions, based on a highest correlation from among the set of correlations, a nerve region indicative of macular damage.

2. The method of claim 1, further comprising:
    generating, based on one or more image grids and the image, the one or more regions of interest of the image.

3. The method of claim 2, wherein the one or more image grids comprise a nerve fiber bundle (NFB) grid, a macular grid, or an optic nerve head (ONH) grid.

4. The method of claim 3, wherein the macular grid comprises a subset of one or more regions of the NFB grid.

5. The method of claim 3, wherein each region of the one or more regions of interest comprises a size based on a scaling factor and the NFB grid, and wherein the macular grid comprises a subset of one or more regions of the NFB grid.

6. The method of claim 5, wherein the scaling factor comprises a distance between a first portion of the image and a second portion of the image.

7. The method of claim 6, wherein the first portion of the image is indicative of a fovea, and wherein the second portion of the image is indicative of a center of a neural canal opening.

8. The method of claim 7, wherein the NFB grid comprises a width and a height.

9. The method of claim 1, further comprising:
    determining a connectivity path of the cell layer to one or more nerve fiber bundle (NFB) segments within at least one of a plurality of NFB regions; and
    determining a path of a retinal segment with a highest cumulative correlation among all possible retinal segment paths.

10. The method of claim 1, further comprising:
    mapping a connectivity of the cell layer to a neural rim of an optic nerve head (ONH) within at least one of the one or more regions of interest;
    mapping a connectivity of the cell layer to an initial nerve fiber bundle (NFB) segment and a final NFB segment to an ONH within at least one of the one or more regions of interest; and
    mapping a connectivity of at least two NFBs within a NFB region of at least one of the one or more regions of interest.

11. A system comprising:
    a memory having computer-executable instructions encoded thereon; and
    at least one processor functionally coupled to the memory and configured, by the computer-executable instructions, to:
        receive an image;
        determine a thickness of a cell layer within at least one of one or more regions of interest of the image;
        determine, for at least one of the one or more regions of interest, a set of correlations of the cell layer thickness to each of a plurality of nerve regions; and
        select from the plurality of nerve regions, based on a highest correlation from among the set of correlations, a nerve region indicative of macular damage.

12. The system of claim 11, wherein the at least one processor is further configured, by the computer-executable instructions, to:
    generate, based on one or more image grids and the image, the one or more regions of interest of the image.

13. The system of claim 12, wherein the one or more image grids comprise a nerve fiber bundle (NFB) grid, a macular grid, or an optic nerve head (ONH) grid.

14. The system of claim 13, wherein the macular grid comprises a subset of one or more regions of the NFB grid.

15. The system of claim 13, wherein each region of the one or more regions of interest comprises a size based on a scaling factor and the NFB grid, and wherein the macular grid comprises a subset of one or more regions of the NFB grid.

16. The system of claim 15, wherein the scaling factor comprises a distance between a first portion of the image and a second portion of the image.

17. The system of claim 16, wherein the first portion of the image is indicative of a fovea, and wherein the second portion of the image is indicative of a center of a neural canal opening.

18. The system of claim 13, wherein the NFB grid comprises a width and a height.

19. The system of claim 18, wherein the at least one processor is further configured, by the computer-executable instructions, to:
   determine a connectivity path of the cell layer to one or more NFB segments within at least one of a plurality of NFB regions; and
   determine a path of a retinal segment with a highest cumulative correlation among all possible retinal segment paths.

20. A computer-readable storage medium comprising processor-executable instructions that, when executed by at least one processor of a computing device, cause the computing device to:
   receive a spectral-domain optical coherence tomography (SD-OCT) image;
   determine a thickness of a macular ganglion cell layer (GCL) within at least one of one or more regions of interest of the SD-OCT image;
   determine, for at least one of the one or more regions of interest, a set of correlations of the GCL thickness to each of a plurality of optic nerve head (ONH) regions;
   select from the plurality of ONH regions, based on a highest correlation from among the set of correlations, an ONH region indicative of macular damage;
   determine, for each of a plurality of nerve fiber bundle (NFB) regions within at least one of the one or more regions of interest, a connectivity path of the GCL to at least two nerve fiber bundle (NFB) segments within the NFB region; and
   determine, for each NFB region, a path of a retinal ganglion cell-axonal complex (RGC-AC) segment with a highest cumulative correlation among all possible RGC-AC segment paths.

* * * * *